(12) United States Patent
Xue et al.

(10) Patent No.: US 11,655,295 B2
(45) Date of Patent: May 23, 2023

(54) ANTI-LAG-3 ANTIBODY AND USE THEREOF

(71) Applicant: SICHUAN KELUN-BIOTECH BIOPHARMACEUTICAL CO., LTD., Sichuan (CN)

(72) Inventors: Tongtong Xue, Sichuan (CN); Qiang Li, Shanghai (CN); Liang Xiao, Sichuan (CN); Yuncheng Zheng, Shanghai (CN); Dengnian Liu, Sichuan (CN); Si Chen, Shanghai (CN); Yan Hu, Sichuan (CN); Lichun Wang, Sichuan (CN); Jingyi Wang, Sichuan (CN)

(73) Assignee: SICHUAN KELUN-BIOTECH BIOPHARMACEUTICAL CO., LTD., Sichuan (CN)

( * ) Notice: Subject to any disclaimer, the term of this patent is extended or adjusted under 35 U.S.C. 154(b) by 423 days.

(21) Appl. No.: 16/963,067

(22) PCT Filed: Jan. 3, 2019

(86) PCT No.: PCT/CN2019/070303
§ 371 (c)(1),
(2) Date: Jul. 17, 2020

(87) PCT Pub. No.: WO2019/141092
PCT Pub. Date: Jul. 25, 2019

(65) Prior Publication Data
US 2020/0347131 A1 Nov. 5, 2020

(30) Foreign Application Priority Data
Jan. 18, 2018 (CN) .......................... 201810050759.9

(51) Int. Cl.
*C07K 16/28* (2006.01)
*A61K 39/395* (2006.01)
*A61P 35/00* (2006.01)

(52) U.S. Cl.
CPC .... *C07K 16/2803* (2013.01); *A61K 39/39558* (2013.01); *A61P 35/00* (2018.01)

(58) Field of Classification Search
CPC .............. A61P 35/00; A61K 39/39558; C07K 16/2803
See application file for complete search history.

(56) References Cited

U.S. PATENT DOCUMENTS

2009/0280128 A1\* 11/2009 Kamogawa .......... A61K 39/395
424/141.1

FOREIGN PATENT DOCUMENTS

| CN | 102176921 A | 9/2011 |
| CN | 105793287 A | 7/2016 |
| WO | 2010/019570 A2 | 2/2010 |
| WO | 2014/008218 A1 | 1/2014 |
| WO | 2015/042246 A1 | 3/2015 |
| WO | 2016/028672 A1 | 2/2016 |
| WO | 2016/061142 A1 | 4/2016 |
| WO | 2017/087589 A2 | 5/2017 |
| WO | WO2017085035 A1 \* | 5/2017 ............. C07K 16/28 |

OTHER PUBLICATIONS

Teufl 2022, ACS Synthetic Biology, 11, 1030 (Year: 2022).\*
Chiu 2019, Antibodies 8 55, 1-80 (Year: 2019).\*
Rabia 2018, Biochemical Engineering Journal 137, 365-374 (Year: 2018).\*
PCT/CN2019/070303 International Search Report dated Apr. 1, 2019.

\* cited by examiner

*Primary Examiner* — Joanne Hama
*Assistant Examiner* — Fozia M Hamud
(74) *Attorney, Agent, or Firm* — Honigman LLP; Thomas A. Wootton, Esq.; Jonathan P. O'Brien

(57) ABSTRACT

The present invention relates to the field of treatment of diseases and immunology. Specifically, the present invention relates to an anti-LAG-3 antibody or an antigen-binding fragment thereof, nucleic acid molecules for encoding said antibody and fragment, and method for preparing said antibody and fragment. The anti-LAG-3 antibody or the antigen-binding fragment thereof according to the present invention has high specificity and high affinity to LAG-3, can effectively block the binding of LAG-3 to MHC II and/or FGL1, and can inhibit and/or block intracellular signaling mediated by LAG-3 binding to MHC II and/or FGL1. Therefore, the present invention further relates to a pharmaceutical composition comprising the antibody or the antigen-binding fragment thereof, and use of the pharmaceutical composition in the preparation of drugs. The drugs are used for improving the activity of immune cells and enhancing the immune response, or are used for preventing and/or treating tumors, infections or autoimmune diseases.

28 Claims, 4 Drawing Sheets
Specification includes a Sequence Listing.

ANTI-LAG-3 ANTIBODY AND USE THEREOF

CROSS-REFERENCE TO RELATED APPLICATIONS

This application is a National Stage Application and claims priority under 35 U.S.C. § 371 to Patent Cooperation Treaty application PCT/CN2019/070303, filed Jan. 3, 2019, which claims the benefit of Chinese Patent Application No. 201810050759.9, filed Jan. 18, 2018, priority is claimed to both of these applications and the disclosures of these prior applications are considered part of the disclosure of this application and to the extent allowed the entire contents of the aforementioned applications are incorporated herein.

SEQUENCE LISTING

This application incorporates by reference in its entirety and includes the Sequence Listing entitled "235427-462157_Seq_Listing_ST25.txt", is 87.5 KB bytes in size and was created on Jul. 17, 2020, and filed electronically herewith.

TECHNICAL FIELD

The present disclosure relates to the field of disease treatment and immunology, and in particular, to an antibody against LAG-3 or an antigen-binding fragment thereof, a nucleic acid molecule encoding the same, a method for preparing the same, and a pharmaceutical composition comprising the same. The invention further relates to the use of said antibody, in particular a humanized antibody, or antigen-binding fragment thereof, for the preparation of a medicament for increasing immune cell activity, enhancing an immune response, or for preventing and/or treating a tumor, infection or autoimmune disease.

BACKGROUND ART

Activation of T lymphocytes is primarily dependent on activation of dual signals, where the first signal is called an antigen-specific signal, and refers to activation of T lymphocytes cell receptor (TCR) by the major histocompatibility complex (MHC); the second signal is called a co-stimulatory signal, including the interaction between multiple molecules and activation of downstream signals. The second signal plays an important role in regulating the function of T lymphocytes, which is achieved by positive or negative co-stimulatory molecules with different functions. Inhibitory signals can be transmitted after the activation of negative co-stimulatory molecules, which can negatively regulate target cell function and play an important role in the occurrence and development of various diseases.

Lymphocyte activation gene 3 (LAG-3) is a member of the immunoglobulin superfamily and consists of three parts: the extracellular domain, the trans-membrane region and the cytoplasmic region. It is mainly expressed in activated T lymphocytes, B lymphocytes, NK cells, plasmacytoid dendritic cells and the like. LAG-3 is a negative costimulatory molecule whose activation negatively regulates lymphocyte function. The LAG-3 gene is located on chromosome 12, and is close to the CD4 molecule on chromosome. And the two molecules share a common exon and intron, and contain some identical amino acids. LAG-3 is structurally closely related to CD4, while its function is opposite to that of CD4. LAG-3 has a high similarity to CD4, and can bind to MHC class II molecules but with higher affinity than CD4, thereby interfering with TCR activation of $CD4^+$ T lymphocytes and inhibiting T lymphocyte activation. In vitro studies have shown that LAG-3 inhibits antigen-induced T lymphocyte proliferative responses, and when LAG-3 is blocked, the activation and proliferation of T lymphocyte and secretion of cytokines by type I helper T cells (Th1) are improved; and the level of LAG-3 on the surface of activated $CD4^+$ regulatory T (Treg) cells is significantly increased, and LAG-3 is a necessary condition for $CD4^+$ Treg to exert maximum immunosuppressive effects. In addition, anti-LAG-3 antibodies also maintain $CD4^+$ and $CD8^+$ T lymphocyte homeostasis, and the ability of $CD8^+$ T lymphocytes to kill tumor cells is significantly enhanced when LAG-3 is blocked. Some disease-related studies have also found that LAG-3 plays an important role in regulating the occurrence and development of disease. The immune regulation of LAG-3 not only includes interfering the binding of CD4/MHC II molecules, but also includes activating the downstream signaling pathways through the binding of LAG-3 to MHC class II molecules. LAG-3 can negatively regulate $CD4^+$ T cells, and inhibit the proliferation of $CD4^+$ Th1 cells and secretion of cytokines such as IFN-$\gamma$, IL-2 and TNF-$\alpha$ thereby through the interaction between LAG-3 and MHC II. However, anti-LAG-3 antibodies can restore their functions and promote cell proliferation and secretion of related cytokines. The LAG-3 molecule also negatively regulates cell activity. In mouse experiments, inhibition of LAG-3 molecules can increase the proliferation and cytotoxicity of $CD8^+$ T cell with a significantly increased secretion of IFN-$\gamma$, and it has a direct regulatory effect on $CD8^+$ T cells. This specific immunosuppression has a better therapeutic effect than a classical immunosuppressant or a therapeutic antibody (e.g., Humira, Remicade) or a soluble receptor (e.g., Enbrel) that blocks TNFa.

Depletion of LAG-$3^+$ T cells can be used to treat or prevent T cell-driven immuno-inflammatory disorders. In autoimmune diseases in which most auto-reactive cells are chronically activated by auto-antigens at the disease site and/or recirculated peripherally, the short-term depletion of antigen-binding protein can selectively deplete the autoimmune T cell pool, thereby providing long-term relief. The superiority of this kind of method has been demonstrated by the pan-lymphocyte depleting antibody Anti-CD52 Campath, in which an antibody treatment with a single dose of 12 mg reduced the relapse rate by 74% compared to the standard method in the multiple sclerosis trial (The CAMMS223 Trial Investigators, New Engl J Med., 2008, 359:1786-801). Because LAG-3 is more selectively expressed compared with CD52, it has less effect on naive and resting memory T cell and natural regulatory T cell pools. This is expected to result in improved therapeutic index and maintenance of efficacy, but the risk of infection, malignancy and the autoimmune associated with Campath is reduced. In addition, in a tuberculin skin challenge model in baboon, the LAG-3 targeting chimeric antibody IMP731 mediates the depletion of LAG-$3^+$ T-cells at both the peripheral and skin attack sites, resulting in a reduced response against tuberculin skin challenge (Poirier N et al., Clin Exp Immunol, 2011, 164:265-74). In further studies, heart-transplanted rats had a high mRNA expression of endogenous LAG-3 after a new donor heart transplantation; and after administration of anti-LAG-3 antibody, LAG-$3^+$ infiltrating T cells was depleted, migration of the effector mononuclear cells into the graft was inhibited and the survival of the graft was prolonged (Haudebourg T et al., Transplantation, 2007, 84:1500-1506).

At present, several LAG-3 antibody drugs have entered clinical trials, mostly at clinical stage I, including anti-tumor drugs BMS 986016 (Bristol-Myers Squibb) and LAG 525 (Novartis), as well as IMP 731 (GlaxoSmithKline) for treatment of psoriasis. However, there are no anti-LAG-3 antibody drugs listed on the market.

Therefore, it is urgent and necessary to develop anti-LAG-3 antibodies with higher specificity, lower toxic side effects and better clinical efficacy, which will provide more drug options for patients with cancer, infection or autoimmune diseases.

SUMMARY OF THE DISCLOSURE

In the present disclosure, the inventors first developed a murine antibody having excellent properties, which is capable of specifically recognizing/binding LAG-3, blocking the binding of LAG-3 to MHC II or FGL1, enhancing immune cell activity in vitro and in vivo, and stimulating immune response. Thus, the murine antibody has the potential to prevent and/or treat tumors, infections or autoimmune diseases.

On this basis, the inventor did a lot of creative work, and carried out in-depth research and modification of the murine antibody, thereby developed a humanized antibody of the murine antibody. The humanized antibody of the present disclosure not only has an extremely high degree of humanization, but also has substantially the same (or even better) biological function as the murine antibody and the human-mouse chimeric antibody (which has the same heavy and light chain variable regions as the murine antibody).

Therefore, the antibody of the present disclosure (especially a humanized antibody) is extremely advantageous, which not only retains the function and properties of the parental murine antibody, but has potential for preventing and treating tumor, infection or autoimmune diseases. Moreover, it has an extremely high degree of humanization so that it can be safely administered to a human subject without eliciting an immunogenic reaction. The antibodies of the invention have significant clinical value.

Antibody of the Present Disclosure

Thus, in one aspect, the present disclosure provides an antibody or antigen-binding fragment thereof, which is capable of specifically binding to LAG-3, the antibody or antigen-binding fragment thereof comprises:

(a) the following three heavy chain variable region (VH) complementarity determining regions (CDRs):

(i) VH CDR1, said VH CDR1 has a sequence as set forth in the CDR1 sequence of the VH as shown in SEQ ID NO: 1, or has a sequence having a substitution, deletion or addition of one or several amino acids (for example, a substitution, deletion or addition of 1, 2 or 3 amino acids) compared to the CDR1 sequence of the VH as shown in SEQ ID NO: 1;

(ii) VH CDR2, said VH CDR2 has a sequence as set forth in the CDR2 sequence of the VH as shown in SEQ ID NO: 1, or has a sequence having a substitution, deletion or addition of one or several amino acids (for example, a substitution, deletion or addition of 1, 2 or 3 amino acids) compared to the CDR2 sequence of the VH as shown in SEQ ID NO: 1; and (iii) VH CDR3, said VH CDR3 has a sequence as set forth in the CDR3 sequence of the VH as shown in SEQ ID NO: 1, or has a sequence having a substitution, deletion or addition of one or several amino acids (for example, a substitution, deletion or addition of 1, 2 or 3 amino acids) compared to the CDR3 sequence of the VH as shown in SEQ ID NO: 1; and/or (b) the following three light chain variable region (VL) complementarity determining regions (CDRs):

(vi) VL CDR1, said VL CDR1 has a sequence as set forth in the CDR1 sequence of the VL as shown in SEQ ID NO: 2, or has a sequence having a substitution, deletion or addition of one or several amino acids (for example, a substitution, deletion or addition of 1, 2 or 3 amino acids) compared to the CDR1 sequence of the VL as shown in SEQ ID NO: 2;

(v) VL CDR2, said VL CDR2 has a sequence as set forth in the CDR2 sequence of the VL as shown in SEQ ID NO: 2, or has a sequence having a substitution, deletion or addition of one or several amino acids (for example, a substitution, deletion or addition of 1, 2 or 3 amino acids) compared to the CDR2 sequence of the VL as shown in SEQ ID NO: 2; and (vi) VL CDR3, said VL CDR3 has a sequence as set forth in the CDR3 sequence of the VL as shown in SEQ ID NO: 2, or has a sequence having a substitution, deletion or addition of one or several amino acids (for example, a substitution, deletion or addition of 1, 2 or 3 amino acids) compared to the CDR3 sequence of the VL as shown in SEQ ID NO: 2.

In certain preferred embodiments, the substitutions described in any of (i)-(vi) are conservative substitutions.

In certain preferred embodiments, the CDR1, CDR2 and CDR3 of the heavy chain variable region (VH), and/or the CDR1, CDR2 and CDR3 of the light chain variable region (VL) are defined by Kabat, Chothia or IMGT numbering system.

In certain preferred embodiments, an antibody or antigen-binding fragment thereof of the invention comprises:

(a) three CDRs of the heavy chain variable region (VH) which is selected from the following:

VH as shown in any one of SEQ ID NO: 1, SEQ ID NO: 16, SEQ ID NO: 18, SEQ ID NO: 20, SEQ ID NO: 22, SEQ ID NO: 24, SEQ ID NO: 26;

and/or (b) three CDRs of the light chain variable region (VL) which is selected from the following:

VL as set forth in any one of SEQ ID NO: 2, SEQ ID NO: 17, SEQ ID NO: 19, SEQ ID NO: 21, SEQ ID NO: 23, SEQ ID NO: 25, SEQ ID NO: 27.

In certain preferred embodiments, the three CDRs of the heavy chain variable region (VH) and/or the three CDRs of the light chain variable region (VL) are defined by Kabat, Chothia or IMGT Numbering system.

In certain preferred embodiments, the antibody or antigen-binding fragment thereof of the invention comprises: the three CDRs of the heavy chain variable region (VH) of SEQ ID NO: 1; and/or, the three CDRs of the light chain variable region (VL) of SEQ ID NO: 2;

Wherein said three CDRs of the heavy chain variable region (VH) and said three CDRs of the light chain variable region (VL) are determined by the IMGT numbering system.

In certain preferred embodiments, the antibody or antigen-binding fragment thereof comprises:

(a) the following three heavy chain variable region (VH) complementarity determining regions (CDRs):

(i) VH CDR1, which consists of one of the following sequences: SEQ ID NO: 3, or a sequence which has a substitution, deletion or addition of one or several amino acids (for example, a substitution, deletion or addition of 1, 2 or 3 amino acids) compared to SEQ ID NO: 3, (ii) VH CDR2, which consists of one of the following sequences: SEQ ID NO: 4, or a sequence which has a substitution, deletion or addition of one or several amino acids (for example, a substitution, deletion or addition of 1, 2 or 3 amino acids) compared to SEQ ID NO: 4, and (iii) VH CDR3, which consists of one of the following sequences: SEQ ID NO: 5, or a sequence which has a substitution, deletion or addition of one or several amino acids (for example, a substitution, deletion or addition of 1, 2 or 3 amino acids) compared to SEQ ID NO: 5;

and/or (b) the following three light chain variable region (VL) complementarity determining regions (CDRs):

(iv) VL CDR1, which consists of one of the following sequences: SEQ ID NO: 6, or a sequence which has a substitution, deletion or addition of one or several amino acids (for example, a substitution, deletion or addition of 1, 2 or 3 amino acids) compared to SEQ ID NO: 6, (v) VL CDR2, which consists of one of the following sequences: SEQ ID NO: 7, (SEQ ID NO: 7, has the following amino acids: Trp, Ala, Ser), or a sequence which has a substitution, deletion or addition of one or several amino acids (for example, a substitution, deletion or addition of 1, 2 or 3 amino acids) compared to SEQ ID NO: 7, and (vi) VL CDR3, which consists of one of the following sequences: SEQ ID NO: 8, or a sequence which has a substitution, deletion or addition of one or several amino acids (for example, a substitution, deletion or addition of 1, 2 or 3 amino acids) compared to SEQ ID NO: 8;

wherein the three CDRs of the heavy chain variable region (VH) and the three CDRs of the light chain variable region (VL) are determined by the IMGT numbering system.

In certain preferred embodiments, the substitutions described in any of (i)-(vi) are conservative substitutions.

In certain preferred embodiments, the VH of an antibody or antigen-binding fragment thereof of the invention comprises: VH CDR1 as set forth in SEQ ID NO: 3; VH CDR2 as set forth in SEQ ID NO: 4; and VH CDR3 as set forth in SEQ ID NO: 5; and the VL of the antibody or antigen-binding fragment thereof comprises: VL CDR1 as shown in SEQ ID NO: 6; VL CDR2 as shown in SEQ ID NO: 7; and VL CDR3 as shown in SEQ ID NO: 8.

In certain preferred embodiments, an antibody or antigen-binding fragment thereof of the invention comprises:

(a) the three CDRs of the heavy chain variable region (VH) as shown in SEQ ID NO: 1; and/or the three CDRs of the light chain variable region (VL) as shown in SEQ ID NO: 2; or (b) the three CDRs of the heavy chain variable region (VH) as shown in SEQ ID NO: 24; and/or the three CDRs of the light chain variable region (VL) as shown in SEQ ID NO: 25;

wherein the three CDRs of the heavy chain variable region (VH) and the three CDRs of the light chain variable region (VL) are defined by the Chothia numbering system.

In certain preferred embodiments, the antibody or antigen-binding fragment thereof comprises:

(a) the following three heavy chain variable region (VH) complementarity determining regions (CDRs):

(i) VH CDR1, which consists of one of the following sequences: SEQ ID NO: 9, or a sequence which has a substitution, deletion or addition of one or several amino acids (for example, a substitution, deletion or addition of 1, 2 or 3 amino acids) compared to SEQ ID NO: 9, (ii) VH CDR2, which consists of one of the following sequences: SEQ ID NO: 10, or a sequence which has a substitution, deletion or addition of one or several amino acids (for example, a substitution, deletion or addition of 1, 2 or 3 amino acids) compared to SEQ ID NO: 10, and (iii) VH CDR3, which consists of one of the following sequences: SEQ ID NO: 11, or a sequence which has a substitution, deletion or addition of one or several amino acids (for example, a substitution, deletion or addition of 1, 2 or 3 amino acids) compared to SEQ ID NO: 11;

and/or (b) the following three light chain variable region (VL) complementarity determining regions (CDRs):

(iv) VL CDR1, which consists of one of the following sequences: SEQ ID NO: 12, or a sequence which has a substitution, deletion or addition of one or several amino acids (for example, a substitution, deletion or addition of 1, 2 or 3 amino acids) compared to SEQ ID NO: 12, (v) VL CDR2, which consists of one of the following sequences: SEQ ID NO: 13, or a sequence which has a substitution, deletion or addition of one or several amino acids (for example, a substitution, deletion or addition of 1, 2 or 3 amino acids) compared to SEQ ID NO: 13, and (vi) VL CDR3, which consists of one of the following sequences: SEQ ID NO: 8, or a sequence which has a substitution, deletion or addition of one or several amino acids (for example, a substitution, deletion or addition of 1, 2 or 3 amino acids) compared to SEQ ID NO: 8;

wherein the three CDRs of the heavy chain variable region (VH) and the three CDRs of the light chain variable region (VL) are determined by the Chothia numbering system.

In certain preferred embodiments, the substitutions described in any of (i)-(vi) are conservative substitutions.

In certain preferred embodiments, the VH of an antibody or antigen-binding fragment thereof of the invention comprises: a VH CDR1 as set forth in SEQ ID NO: 9; a VH CDR2 as set forth in SEQ ID NO: 10; a VH CDR3 as set forth in SEQ ID NO: 11; and the VL of the antibody or antigen-binding fragment thereof comprises: VL CDR1 as shown in SEQ ID NO: 12; VL CDR2 as shown in SEQ ID NO: 13; VL CDR3 as shown in SEQ ID NO: 8.

In certain preferred embodiments, the VH of an antibody or antigen-binding fragment thereof of the invention comprises: a VH CDR1 as set forth in SEQ ID NO: 9; a VH CDR2 as set forth in SEQ ID NO: 10; a VH CDR3 as set forth in SEQ ID NO: 11; and the VL of the antibody or antigen-binding fragment thereof comprises: VL CDR1 as shown in SEQ ID NO: 12; VL CDR2 as shown in SEQ ID NO: 54; VL CDR3 as shown in SEQ ID NO: 8.

In certain preferred embodiments, an antibody or antigen-binding fragment thereof of the invention comprises:

(a) The 3 CDRs of the heavy chain variable region (VH) as shown in SEQ ID NO: 1; and/or the 3 CDRs of the light chain variable region (VL) as shown in SEQ ID NO: 2;

(b) The 3 CDRs of the heavy chain variable region (VH) as shown in SEQ ID NO: 22; and/or the 3 CDRs of light chain variable region (VL) as shown in SEQ ID NO: 23;

(c) The 3 CDRs of the heavy chain variable region (VH) as shown in SEQ ID NO: 24; and/or the 3 CDRs of the light chain variable region (VL) as shown in SEQ ID NO: 25; or (d) The 3 CDRs of the heavy chain variable region (VH) as shown in SEQ ID NO: 26; and/or the 3 CDRs of the light chain variable region (VL) as shown in SEQ ID NO: 27;

wherein the three CDRs of the heavy chain variable region (VH) and the three CDRs of the light chain variable region (VL) are defined by the Kabat numbering system.

In certain preferred embodiments, the antibody or antigen-binding fragment thereof comprises:

(a) the following three heavy chain variable region (VH) CDRs:

(i) VH CDR1, which consists of one of the following sequences: SEQ ID NO: 14, or a sequence which has a substitution, deletion or addition of one or several amino acids (for example, a substitution, deletion or addition of 1, 2 or 3 amino acids) compared to SEQ ID NO: 14, (ii) VH CDR2, which consists of one of the following sequences: SEQ ID NO: 15, or a sequence which has a substitution, deletion or addition of one or several amino acids (for example, a substitution, deletion or addition of 1, 2 or 3 amino acids) compared to SEQ ID NO: 15, and (iii) VH CDR3, which consists of one of the following sequences: SEQ ID NO: 11, or a sequence which has a substitution, deletion or addition of one or several amino acids (for example, a substitution, deletion or addition of 1, 2 or 3 amino acids) compared to SEQ ID NO: 11;

and/or (b) the following three light chain variable region (VL) CDRs:

(iv) VL CDR1, which consists of one of the following sequences: SEQ ID NO: 12, or a sequence which has a substitution, deletion or addition of one or several amino acids (for example, a substitution, deletion or addition of 1, 2 or 3 amino acids) compared to SEQ ID NO: 12, (v) VL CDR2, which consists of one of the following sequences: SEQ ID NO: 13, or a sequence which has a substitution, deletion or addition of one or several amino acids (for example, a substitution, deletion or addition of 1, 2 or 3 amino acids) compared to SEQ ID NO: 13, and (vi) VL CDR3, which consists of one of the following sequences: SEQ ID NO: 8, or a sequence which has a substitution, deletion or addition of one or several amino acids (for example, a substitution, deletion or addition of 1, 2 or 3 amino acids) compared to SEQ ID NO: 8;

wherein the three CDRs of the heavy chain variable region (VH) and the three CDRs of the light chain variable region (VL) are determined by a Kabat numbering system.

In certain preferred embodiments, the substitutions described in any of (i)-(vi) are conservative substitutions.

In certain preferred embodiments, the VH of an antibody or antigen-binding fragment thereof of the invention comprises: a VH CDR1 as set forth in SEQ ID NO: 14; a VH CDR2 as set forth in SEQ ID NO: 15; a VH CDR3 as set forth in SEQ ID NO: 11; and the VL of the antibody or antigen-binding fragment thereof comprises: VL CDR1 as shown in SEQ ID NO: 12; VL CDR2 as shown in SEQ ID NO: 13; VL CDR3 as shown in SEQ ID NO: 8.

In certain preferred embodiments, the VH of an antibody or antigen-binding fragment thereof of the invention comprises: a VH CDR1 as set forth in SEQ ID NO: 14; a VH CDR2 as set forth in SEQ ID NO: 55; a VH CDR3 as set forth in SEQ ID NO: 11; and the VL of the antibody or antigen-binding fragment thereof comprises: VL CDR1 as shown in SEQ ID NO: 12; VL CDR2 as shown in SEQ ID NO: 13; VL CDR3 as shown in SEQ ID NO: 8.

In certain preferred embodiments, the VH of an antibody or antigen-binding fragment thereof of the invention comprises: a VH CDR1 as set forth in SEQ ID NO: 56; a VH CDR2 as set forth in SEQ ID NO: 57; a VH CDR3 as set forth in SEQ ID NO: 11; and the VL of the antibody or antigen-binding fragment thereof comprises: VL CDR1 as shown in SEQ ID NO: 12; VL CDR2 as shown in SEQ ID NO: 54; VL CDR3 as shown in SEQ ID NO: 8.

In certain preferred embodiments, the VH of an antibody or antigen-binding fragment thereof of the invention comprises: a VH CDR1 as set forth in SEQ ID NO: 14; a VH CDR2 as set forth in SEQ ID NO: 58; a VH CDR3 as set forth in SEQ ID NO: 11; and the VL of the antibody or antigen-binding fragment thereof comprises: VL CDR1 as shown in SEQ ID NO: 12; VL CDR2 as shown in SEQ ID NO: 13; VL CDR3 as shown in SEQ ID NO: 8.

In certain preferred embodiments, an antibody or antigen-binding fragment thereof of the invention comprises a heavy chain variable region (VH) CDR and/or a light chain variable region (VL) CDR as mentioned above, and further comprises a framework region (FR) of immunoglobulin derived from mammalian (e.g., mouse or human).

In certain preferred embodiments, the VH of an antibody or antigen-binding fragment thereof of the invention comprises a heavy chain variable region (VH) framework region (FR) derived from a murine immunoglobulin, and/or the VL of the antibody or antigen-binding fragment thereof comprises a light chain variable region (VL) framework region (FR) derived from a murine immunoglobulin.

In certain preferred embodiments, the VH of an antibody or antigen-binding fragment thereof of the invention comprises a heavy chain variable region (VH) framework region (FR) derived from a human immunoglobulin, and/or the VL of the antibody or antigen-binding fragment thereof comprises a light chain variable region (VL) framework region (FR) derived from a human immunoglobulin. In such embodiments, the heavy chain variable region FR and/or the light chain variable region FR of an antibody or antigen-binding fragment thereof of the invention may comprise one or more non-human (e.g., murine) amino acid residues. For example, the heavy chain framework region FR and/or the light chain framework region FR may comprise one or more amino acid back mutations, and the corresponding murine amino acid residues are present in these back mutations.

In certain preferred embodiments, an antibody or antigen-binding fragment thereof of the invention comprises:

(a) A heavy chain framework region of a human immunoglobulin or a variant thereof, said variant has a conservative substitution of up to 20 amino acids (e.g., a conservative substitution of up to 15, up to 10, or up to 5 amino acids; for example, a conservative substitution of 1, 2, 3, 4 or 5 amino acids) compared to the germline antibody gene sequence from which it is derived; and/or (b) A light chain framework region of a human immunoglobulin or a variant thereof, said variant has a conservative substitution of up to 20 amino acids (e.g., a conservative substitution of up to 15, up to 10, or up to 5 amino acids; for example, a conservative substitution of 1, 2, 3, 4 or 5 amino acids) compared to the germline antibody gene sequence from which it is derived.

Thus, in certain preferred embodiments, the antibody or antigen-binding fragment thereof of the invention is humanized. In certain preferred embodiments, the antibody or antigen-binding fragment thereof of the invention has a humanization degree of at least 75%, at least 80%, at least 85%, at least 90%, at least 91%, at least 92%, at least 93%, at least 94%, at least 95%, at least 96%, at least 97%, at least 98%, at least 99% or 100%.

In certain preferred embodiments, an antibody or antigen-binding fragment thereof of the invention comprises:

(a) A heavy chain variable region (VH) comprising an amino acid sequence selected from the group consisting of:

(i) a sequence as shown in any one of SEQ ID NOs: 1, 16, 18, 20, 22, 24, or 26;

(ii) a sequence having a substitution, deletion or addition of one or several amino acids (for example, a substitution, deletion or addition of 1, 2, 3, 4 or 5 amino acids) compared to the sequence set forth in any one of SEQ ID NOs: 1, 16, 18, 20, 22, 24, or 26; or (iii) a sequence having at least 80%, at least 85%, at least 90%, at least 91%, at least 92%, at least 93%, at least 94%, at least 95%, at least 96%, at least 97%, at least 98%, at least 99%, or 100% identity to any one of SEQ ID NOs: 1, 16, 18, 20, 22, 24, or 26;

and/or (b) A light chain variable region (VL) comprising an amino acid sequence selected from the group consisting of:

(iv) a sequence as shown in any one of SEQ ID NOs: 2, 17, 19, 21, 23, 25, 27;

(v) a sequence having a substitution, deletion or addition of one or several amino acids (for example, a substitution, deletion or addition of 1, 2, 3, 4 or 5 amino acids) compared to the sequence set forth in any one of SEQ ID NOs: 2, 17, 19, 21, 23, 25, 27; or (vi) a sequence having at least 80%, at least 85%, at least 90%, at least 91%, at least 92%, at least 93%, at least 94%, at least 95%, at least 96%, at least 97%, at least 98%, at least 99%, or 100% identity to any one of SEQ ID NOs: 2, 17, 19, 21, 23, 25, 27.

In certain preferred embodiments, the substitutions described in (ii) or (v) are conservative substitutions.

In certain preferred embodiments, an antibody or antigen-binding fragment thereof of the invention comprises:

(a) A heavy chain variable region (VH) comprising an amino acid sequence selected from the group consisting of:

(i) a sequence shown in SEQ ID NO: 1;

(ii) a sequence having a substitution, deletion or addition of one or several amino acids (for example, a substitution, deletion or addition of 1, 2, 3, 4 or 5 amino acids) compared to the sequence set forth in SEQ ID NO: 1; or (iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 1;

and (b) A light chain variable region (VL) comprising an amino acid sequence selected from the group consisting of:

(vi) a sequence shown in SEQ ID NO: 2;

(v) a sequence having a substitution, deletion or addition of one or several amino acids (for example, a substitution, deletion or addition of 1, 2, 3, 4 or 5 amino acids) compared to the sequence set forth in SEQ ID NO: 2; or (vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 2.

In certain preferred embodiments, the substitutions described in (ii) or (v) are conservative substitutions.

In certain preferred embodiments, an antibody or antigen-binding fragment thereof of the invention comprises:

(a) A heavy chain variable region (VH) comprising an amino acid sequence selected from the group consisting of:

(i) the sequence shown in SEQ ID NO: 16;

(ii) a sequence having a substitution, deletion or addition of one or several amino acids (for example, a substitution, deletion or addition of 1, 2, 3, 4 or 5 amino acids) compared to the sequence set forth in SEQ ID NO: 16;

(iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 16;

and (b) a light chain variable region (VL) comprising an amino acid sequence selected from the group consisting of:

(iv) the sequence shown in SEQ ID NO: 17;

(v) a sequence having a substitution, deletion or addition of one or several amino acids (for example, a substitution, deletion or addition of 1, 2, 3, 4 or 5 amino acids) compared to the sequence set forth in SEQ ID NO: 17;

(vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 17.

In certain preferred embodiments, the substitutions described in (ii) or (v) are conservative substitutions.

In certain preferred embodiments, an antibody or antigen-binding fragment thereof of the invention comprises:

(a) A heavy chain variable region (VH) comprising an amino acid sequence selected from the group consisting of:

(i) the sequence shown in SEQ ID NO: 18;

(ii) a sequence having a substitution, deletion or addition of one or several amino acids (for example, a substitution, deletion or addition of 1, 2, 3, 4 or 5 amino acids) compared to the sequence set forth in SEQ ID NO: 18;

(iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 18;

and (b) A light chain variable region (VL) comprising an amino acid sequence selected from the group consisting of:

(iv) the sequence shown in SEQ ID NO: 19;

(v) a sequence having a substitution, deletion or addition of one or several amino acids (for example, a substitution, deletion or addition of 1, 2, 3, 4 or 5 amino acids) compared to the sequence set forth in SEQ ID NO: 19;

(vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 19.

In certain preferred embodiments, the substitutions described in (ii) or (v) are conservative substitutions.

In certain preferred embodiments, an antibody or antigen-binding fragment thereof of the invention comprises:

(a) A heavy chain variable region (VH) comprising an amino acid sequence selected from the group consisting of:

(i) the sequence shown in SEQ ID NO: 20;

(ii) a sequence having a substitution, deletion or addition of one or several amino acids (for example, a substitution, deletion or addition of 1, 2, 3, 4 or 5 amino acids) compared to the sequence set forth in SEQ ID NO: 20;

(iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 20;

and (b) A light chain variable region (VL) comprising an amino acid sequence selected from the group consisting of:

(iv) the sequence shown in SEQ ID NO: 21;

(v) a sequence having a substitution, deletion or addition of one or several amino acids (for example, a substitution, deletion or addition of 1, 2, 3, 4 or 5 amino acids) compared to the sequence set forth in SEQ ID NO: 21;

(vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 21.

In certain preferred embodiments, the substitutions described in (ii) or (v) are conservative substitutions.

In certain preferred embodiments, an antibody or antigen-binding fragment thereof of the invention comprises:

(a) A heavy chain variable region (VH) comprising an amino acid sequence selected from the group consisting of:
  (i) the sequence shown in SEQ ID NO: 22;
  (ii) a sequence having a substitution, deletion or addition of one or several amino acids (for example, a substitution, deletion or addition of 1, 2, 3, 4 or 5 amino acids) compared to the sequence set forth in SEQ ID NO: 22;
  (iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 22;
and
(b) A light chain variable region (VL) comprising an amino acid sequence selected from the group consisting of:
  (iv) the sequence shown in SEQ ID NO: 23;
  (v) a sequence having a substitution, deletion or addition of one or several amino acids (for example, a substitution, deletion or addition of 1, 2, 3, 4 or 5 amino acids) compared to the sequence set forth in SEQ ID NO: 23;
  (vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 23.

In certain preferred embodiments, the substitutions described in (ii) or (v) are conservative substitutions.

In certain preferred embodiments, an antibody or antigen-binding fragment thereof of the invention comprises:

(a) A heavy chain variable region (VH) comprising an amino acid sequence selected from the group consisting of:
  (i) the sequence shown in SEQ ID NO: 24;
  (ii) a sequence having a substitution, deletion or addition of one or several amino acids (for example, a substitution, deletion or addition of 1, 2, 3, 4 or 5 amino acids) compared to the sequence set forth in SEQ ID NO: 24;
  (iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 24;
and
(b) A light chain variable region (VL) comprising an amino acid sequence selected from the group consisting of:
  (iv) The sequence shown in SEQ ID NO: 25;
  (v) a sequence having a substitution, deletion or addition of one or several amino acids (for example, a substitution, deletion or addition of 1, 2, 3, 4 or 5 amino acids) compared to the sequence set forth in SEQ ID NO: 25;
  (vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 25.

In certain preferred embodiments, the substitutions described in (ii) or (v) are conservative substitutions.

In certain preferred embodiments, an antibody or antigen-binding fragment thereof of the invention comprises:

(a) A heavy chain variable region (VH) comprising an amino acid sequence selected from the group consisting of:
  (i) the sequence shown in SEQ ID NO: 26;
  (ii) a sequence having a substitution, deletion or addition of one or several amino acids (for example, a substitution, deletion or addition of 1, 2, 3, 4 or 5 amino acids) compared to the sequence set forth in SEQ ID NO: 26;
  (iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 26;
and
(b) A light chain variable region (VL) comprising an amino acid sequence selected from the group consisting of:
  (iv) the sequence shown in SEQ ID NO: 27;
  (v) a sequence having a substitution, deletion or addition of one or several amino acids (for example, a substitution, deletion or addition of 1, 2, 3, 4 or 5 amino acids) compared to the sequence set forth in SEQ ID NO: 27;
  (vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 27.

In certain preferred embodiments, the substitutions described in (ii) or (v) are conservative substitutions.

In certain preferred embodiments, the antibody or antigen-binding fragment thereof of the invention comprises:

(1) a VH having the sequence set forth in SEQ ID NO: 1 and a VL having the sequence set forth in SEQ ID NO: 2;
(2) a VH having the sequence set forth in SEQ ID NO: 16 and a VL having the sequence set forth in SEQ ID NO: 17;
(3) a VH having the sequence set forth in SEQ ID NO: 18 and a VL having the sequence set forth in SEQ ID NO: 19;
(4) a VH having the sequence set forth in SEQ ID NO: 20 and a VL having the sequence set forth in SEQ ID NO: 21;
(5) a VH having the sequence set forth in SEQ ID NO: 22 and a VL having the sequence set forth in SEQ ID NO: 23;
(6) a VH having the sequence set forth in SEQ ID NO: 24 and a VL having the sequence set forth in SEQ ID NO: 25; or
(7) a VH having the sequence set forth in SEQ ID NO: 26 and a VL having the sequence set forth in SEQ ID NO: 27.

In certain preferred embodiments, the antibodies or antigen-binding fragments thereof of the invention further comprise a constant region sequence derived from mammalian (e.g., murine or human) immunoglobulins or variants thereof, and the variants have substitutions, deletions or additions of one or more amino acids compared to the wild type sequences from which they are derived. In certain preferred embodiments, the variants have conservative substitutions of one or more amino acids compared to the wild type sequences from which they are derived.

In certain preferred embodiments, the heavy chain of the antibodies or antigen-binding fragments thereof of the invention comprises a heavy chain constant region (CH) of a human immunoglobulin or a variant thereof, and the variant has a substitution, deletion or addition of one or more amino acids (e.g., a substitution, deletion or addition of up to 20, up to 15, up to 10, or up to 5 amino acids; e.g., a substitution, deletion or addition of 1, 2, 3, 4 or 5 amino acids) compared to the wild type sequence from which it is derived; and/or the light chain of antibodies or antigen-binding fragments thereof of the invention comprises a light chain constant region (CL) of a human immunoglobulin or a variant thereof, and the variant has a substitution, deletion or addition of one or more amino acids (e.g., a substitution, deletion or addition of up to 20, up to 15, up to 10, or up to 5 amino acids; e.g., a substitution, deletion or addition of 1, 2, 3, 4 or 5 amino acids) compared to the wild type sequence from which it is derived.

In certain preferred embodiments, the heavy chain of the antibodies or antigen-binding fragments thereof of the invention comprises a heavy chain constant region (CH) of a human immunoglobulin or a variant thereof, and the variant has a substitution, deletion or addition of one or more amino acids (e.g., a substitution, deletion or addition of up to 20, up to 15, up to 10, or up to 5 amino acids; e.g., a substitution, deletion or addition of 1, 2, 3, 4 or 5 amino acids) compared to the wild type sequence from which it is derived; and/or the light chain of antibodies or antigen-binding fragments thereof of the invention comprises a light chain constant region (CL) of a human immunoglobulin or a variant thereof, and the variant has a substitution, deletion or addition of up to 20 amino acids (e.g., a substitution, deletion or addition of up to 15, up to 10, or up to 5 amino acids; e.g., a substitution, deletion or addition of 1, 2, 3, 4 or 5 amino acids) compared to the wild type sequence from which it is derived.

In certain preferred embodiments, the heavy chain of the antibodies or antigen-binding fragments thereof of the invention comprises a heavy chain constant region (CH) of a human immunoglobulin or a variant thereof, and the variant has a substitution, deletion or addition of up to 20 amino acids (e.g., a substitution, deletion or addition of up to 15, up to 10, or up to 5 amino acids; e.g., a substitution, deletion or addition of 1, 2, 3, 4 or 5 amino acids) compared to the wild type sequence from which it is derived; and/or the light chain of antibodies or antigen-binding fragments thereof of the invention comprises a light chain constant region (CL) of a human immunoglobulin or a variant thereof, and the variant has a substitution, deletion or addition of up to 20 amino acids (e.g., a substitution, deletion or addition of up to 15, up to 10, or up to 5 amino acids; e.g., a substitution, deletion or addition of 1, 2, 3, 4 or 5 amino acids) compared to the wild type sequence from which it is derived.

In certain preferred embodiments, the antibodies or antigen-binding fragments thereof of the invention comprises a variant of the heavy chain constant region (CH) of a human immunoglobulin, and the variant has altered (e.g., enhanced, decreased, or eliminated) effector function compared to the wild type sequence from which it is derived. In such embodiments, the variant typically has at least one amino acid substitution compared to the wild type sequence from which it is derived. The Fc region of an antibody mediates several important effector functions, such as ADCC, phagocytosis, CDC and so on. In some situations, these effector functions are required for therapeutic antibodies; but in other situations, these effector functions may be unnecessary or even harmful depending on the intended purpose. Thus, in certain embodiments, the antibodies or antigen-binding fragments thereof of the invention have reduced or even eliminated effector functions (e.g., ADCC and/or CDC activity). In such embodiments, the antibodies or antigen-binding fragments thereof of the invention comprise a variant of a human IgG heavy chain constant region, and the variant has at least one of the following substitutions compared to the wild type sequence from which it is derived: Ser228Pro, Leu234Ala, Leu235Ala, Gly237Ala, Asn297Ala, Asp356Glu and Leu358Met (the amino acid positions mentioned above are based on the EU numbering system, Edelman, G M et al., Proc. Natl. Acad. USA, 63, 78-85 (1969) PMID: 5257969).

In certain exemplary embodiments, the antibodies or antigen-binding fragments thereof of the invention comprise a variant of a human IgG4 heavy chain constant region, and the variant has the following substitution compared to the wild type sequence from which it is derived: Ser228Pro (according to the position of the EU numbering system). In such embodiments, the antibodies or antigen-binding fragments thereof of the invention have reduced ADCC and CDC activities.

In certain exemplary embodiments, the antibodies or antigen-binding fragments thereof of the invention comprise a variant of a human IgG1 heavy chain constant region, and the variant has the following substitutions compared to the wild type sequence from which it is derived: Leu234Ala, Leu235Ala and Gly237Ala (according to the position of the EU numbering system). In such embodiments, the antibodies or antigen-binding fragments thereof of the invention have reduced ADCC and CDC activities.

In certain exemplary embodiments, the antibodies or antigen-binding fragments thereof of the invention comprise a variant of a human IgG1 heavy chain constant region, and the variant has the following substitutions compared to the wild type sequence from which it is derived: Asn297Ala, Asp356Glu and Leu358Met (according to the position of the EU numbering system). In such embodiments, the antibodies or antigen-binding fragments thereof of the invention have eliminated ADCC activity.

In certain preferred embodiments, the antibodies or antigen-binding fragments thereof of the invention comprise a variant of the heavy chain constant region (CH) of a human immunoglobulin, and the variant has substantially unchanged effector functions compared to the wild type sequence from which it is derived. In such embodiments, the variant may have a conservative substitution of up to 20 amino acids (e.g., a conservative substitution of up to 15, up to 10, or up to 5 amino acids; e.g., a conservative substitution of 1, 2, 4, or 5 amino acids) compared to the wild type sequence from which it is derived.

In certain preferred embodiments, the heavy chains of the antibodies or antigen-binding fragments thereof of the invention comprise a heavy chain constant region (CH) of a murine immunoglobulin or a variant thereof, and the variant has a substitution, deletion or addition of one or more amino acids (e.g., a substitution, deletion or addition of up to 20, up to 15, up to 10, or up to 5 amino acids; e.g., a substitution, deletion or addition of 1, 2, 3, 4 or 5 amino acids) compared to the wild type sequence from which it is derived; and/or the light chains of an antibodies or antigen-binding fragments thereof of the invention comprise a light chain constant region (CL) of a murine immunoglobulin or a variant thereof, and the variant has a substitution, deletion or addition of one or more amino acids (e.g., a substitution, deletion or addition of up to 20, up to 15, up to 10, or up to 5 amino acids; e.g., a substitution, deletion or addition of 1, 2, 3, 4 or 5 amino acids) compared to the wild type sequence from which it is derived.

In certain preferred embodiments, the heavy chains of the antibodies or antigen-binding fragments thereof of the invention comprise a heavy chain constant region (CH) of a murine immunoglobulin or a variant thereof, and the variant has a substitution, deletion or addition of one or more amino acids (e.g., a substitution, deletion or addition of up to 20, up to 15, up to 10, or up to 5 amino acids; e.g., a substitution, deletion or addition of 1, 2, 3, 4 or 5 amino acids) compared to the wild type sequence from which it is derived; and/or, a light chain of an antibodies or antigen-binding fragments thereof of the invention comprises a light chain constant region (CL) of a murine immunoglobulin or a variant thereof, and the variant has a substitution, deletion or addition of up to 20 amino acids (e.g., a substitution, deletion or addition of up to 15, up to 10, or up to 5 amino acids; e.g., a substitution, deletion or addition of 1, 2, 3, 4 or 5 amino acids) compared to the wild type sequence from which it is derived.

In certain preferred embodiments, the heavy chains of the antibodies or antigen-binding fragments thereof of the invention comprise a heavy chain constant region (CH) of a murine immunoglobulin or a variant thereof, and the variant has a substitution, deletion or addition of up to 20 amino acids (e.g., a substitution, deletion or addition of up to 15, up to 10, or up to 5 amino acids; e.g., a substitution, deletion or addition of 1, 2, 3, 4 or 5 amino acids) compared to the wild type sequence from which it is derived; and/or a light chains of an antibodies or antigen-binding fragments thereof of the invention comprises a light chain constant region (CL) of a murine immunoglobulin or a variant thereof, and the variant has a substitution, deletion or addition of up to 20 amino acids (e.g., a substitution, deletion or addition of up to 15, up to 10, or up to 5 amino acids; e.g., a substitution, deletion or addition of 1, 2, 3, 4 or 5 amino acids) compared to the wild type sequence from which it is derived.

In certain preferred embodiments, the heavy chain constant region is an IgG heavy chain constant region, such as an IgG1, IgG2, IgG3 or IgG4 heavy chain constant region. In certain preferred embodiments, the heavy chain constant region is a murine IgG1, IgG2, IgG3 or IgG4 heavy chain constant region. In certain preferred embodiments, the heavy chain constant region is a human IgG1, IgG2, IgG3 or IgG4 heavy chain constant region. In certain embodiments, preferably the heavy chain constant region is a human IgG1 or IgG4 heavy chain constant region. In certain preferred embodiments, the heavy chain constant region is the IgG1 heavy chain constant region having a sequence set forth in SEQ ID NO: 30, or the IgG4 heavy chain constant region having a sequence set forth in SEQ ID NO: 28.

In certain preferred embodiments, the light chain constant region is a kappa light chain constant region. In certain preferred embodiments, the light chain constant region is a murine kappa light chain constant region. In certain preferred embodiments, the light chain constant region is a human kappa light chain constant region.

In certain preferred embodiments, the antibodies or antigen-binding fragments thereof of the invention comprise:

(a) a heavy chain constant region (CH) comprising an amino acid sequence selected from the group consisting of:
(i) the sequence of SEQ ID NO: 28 or the sequence of SEQ ID NO: 30;
(ii) a sequence having a substitution, deletion or addition of one or several amino acids (for example, a substitution, deletion or addition of 1, 2, 3, 4 or 5 amino acids) compared to the sequence set forth in SEQ ID NO: 28 or SEQ ID NO: 30; or
(iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 28 or SEQ ID NO: 30;
and/or (b) a light chain constant region (CL) comprising an amino acid sequence selected from the group consisting of:
(iv) the sequence shown as SEQ ID NO: 33;
(v) a sequence having a substitution, deletion or addition of one or several amino acids (for example, a substitution, deletion or addition of 1, 2, 3, 4 or 5 amino acids) compared to the sequence set forth in SEQ ID NO:33; or
(vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 33.

In certain preferred embodiments, the substitutions described in (ii) or (v) are conservative substitutions.

In certain preferred embodiments, the sequence described in (ii) are selected from the group consisting of the amino acid sequences set forth in SEQ ID NO: 29, 31 and 32.

In certain preferred embodiments, the antibodies or antigen-binding fragments thereof of the invention comprise:
(a) a heavy chain constant region (CH) as set forth in any one of SEQ ID NOs: 28-32; and/or
(b) a light chain constant region (CL) as set forth in SEQ ID NO:33.

In certain preferred embodiments, the antibodies or antigen-binding fragments thereof of the invention comprise:
(a) a heavy chain comprising an amino acid sequence selected from the group consisting of:
(i) the sequence set forth in SEQ ID NO:38;
(ii) a sequence having a substitution, deletion or addition of one or several amino acids (for example, a substitution, deletion or addition of 1, 2, 3, 4 or 5 amino acids) compared to the sequence set forth in SEQ ID NO: 38; or
(iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 38;
and (b) a light chain comprising an amino acid sequence selected from the group consisting of:
(iv) the sequence shown as SEQ ID NO:39;
(v) a sequence having a substitution, deletion or addition of one or several amino acids (for example, a substitution, deletion or addition of 1, 2, 3, 4 or 5 amino acids) compared to the sequence set forth in SEQ ID NO: 39; or
(vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 39.

In certain preferred embodiments, the substitutions described in (ii) or (v) are conservative substitutions.

In certain preferred embodiments, the antibodies or antigen-binding fragments thereof of the invention comprise:
(a) a heavy chain comprising an amino acid sequence selected from the group consisting of:
(i) the sequence set forth in SEQ ID NO:40;
(ii) a sequence having a substitution, deletion or addition of one or several amino acids (for example, a substitution, deletion or addition of 1, 2, 3, 4 or 5 amino acids) compared to the sequence set forth in SEQ ID NO: 40; or
(iii) a sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence set forth in SEQ ID NO: 40;
and (b) a light chain comprising an amino acid sequence selected from the group consisting of:

(iv) the sequence shown as SEQ ID NO:41;

(v) a sequence having a substitution, deletion or addition of one or several amino acids (for example, a substitution, deletion or addition of 1, 2, 3, 4 or 5 amino acids) compared to the sequence set forth in SEQ ID NO: 41; or (vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 41.

In certain preferred embodiments, the substitutions described in (ii) or (v) are conservative substitutions.

In certain preferred embodiments, the antibodies or antigen-binding fragments thereof of the invention comprise:

(a) a heavy chain comprising an amino acid sequence selected from the group consisting of:

(i) the sequence set forth in SEQ ID NO:42;

(ii) a sequence having a substitution, deletion or addition of one or several amino acids (for example, a substitution, deletion or addition of 1, 2, 3, 4 or 5 amino acids) compared to the sequence set forth in SEQ ID NO: 42; or (iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 42;

and (b) a light chain comprising an amino acid sequence selected from the group consisting of:

(iv) the sequence shown as SEQ ID NO:43;

(v) a sequence having a substitution, deletion or addition of one or several amino acids (for example, a substitution, deletion or addition of 1, 2, 3, 4 or 5 amino acids) compared to the sequence set forth in SEQ ID NO: 43; or (vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 43.

In certain preferred embodiments, the substitutions described in (ii) or (v) are conservative substitutions.

In certain preferred embodiments, the antibodies or antigen-binding fragments thereof of the invention comprise:

(a) a heavy chain comprising an amino acid sequence selected from the group consisting of:

(i) the sequence set forth in SEQ ID NO:44;

(ii) a sequence having a substitution, deletion or addition of one or several amino acids (for example, a substitution, deletion or addition of 1, 2, 3, 4 or 5 amino acids) compared to the sequence set forth in SEQ ID NO: 44; or (iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 44;

and (b) a light chain comprising an amino acid sequence selected from the group consisting of:

(iv) the sequence shown as SEQ ID NO:45;

(v) a sequence having a substitution, deletion or addition of one or several amino acids (for example, a substitution, deletion or addition of 1, 2, 3, 4 or 5 amino acids) compared to the sequence set forth in SEQ ID NO: 45; or (vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 45.

In certain preferred embodiments, the substitutions described in (ii) or (v) are conservative substitutions.

In certain preferred embodiments, the antibodies or antigen-binding fragments thereof of the invention comprise:

(a) a heavy chain comprising an amino acid sequence selected from the group consisting of:

(i) the sequence set forth in SEQ ID NO:46;

(ii) a sequence having a substitution, deletion or addition of one or several amino acids (for example, a substitution, deletion or addition of 1, 2, 3, 4 or 5 amino acids) compared to the sequence set forth in SEQ ID NO: 46; or (iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 46;

and (b) a light chain comprising an amino acid sequence selected from the group consisting of:

(iv) the sequence shown as SEQ ID NO:47;

(v) a sequence having a substitution, deletion or addition of one or several amino acids (for example, a substitution, deletion or addition of 1, 2, 3, 4 or 5 amino acids) compared to the sequence set forth in SEQ ID NO: 47; or (vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 47.

In certain preferred embodiments, the substitutions described in (ii) or (v) are conservative substitutions.

In certain preferred embodiments, the antibodies or antigen-binding fragments thereof of the invention comprise:

(a) a heavy chain comprising an amino acid sequence selected from the group consisting of:

(i) the sequence set forth in SEQ ID NO:48;

(ii) a sequence having a substitution, deletion or addition of one or several amino acids (for example, a substitution, deletion or addition of 1, 2, 3, 4 or 5 amino acids) compared to the sequence set forth in SEQ ID NO: 48; or (iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 48;

and (b) a light chain comprising an amino acid sequence selected from the group consisting of:

(iv) the sequence set forth in SEQ ID NO:49;

(v) a sequence having a substitution, deletion or addition of one or several amino acids (for example, a substitution, deletion or addition of 1, 2, 3, 4 or 5 amino acids) compared to the sequence set forth in SEQ ID NO: 49; or (vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 49.

In certain preferred embodiments, the substitutions described in (ii) or (v) are conservative substitutions.

In certain preferred embodiments, the antibodies or antigen-binding fragments thereof of the invention comprise:

(a) a heavy chain comprising an amino acid sequence selected from the group consisting of:

(i) the sequence set forth in SEQ ID NO:50;

(ii) a sequence having a substitution, deletion or addition of one or several amino acids (for example, a substitution, deletion or addition of 1, 2, 3, 4 or 5 amino acids) compared to the sequence set forth in SEQ ID NO: 50; or (iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 50;

and (b) a light chain comprising an amino acid sequence selected from the group consisting of:

(iv) the sequence shown as SEQ ID NO:51;

(v) a sequence having a substitution, deletion or addition of one or several amino acids (for example, a substitution, deletion or addition of 1, 2, 3, 4 or 5 amino acids) compared to the sequence set forth in SEQ ID NO: 51; or (vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 51.

In certain preferred embodiments, the substitutions described in (ii) or (v) are conservative substitutions.

In certain preferred embodiments, the antibodies or antigen-binding fragments thereof of the invention comprise:

(a) a heavy chain comprising an amino acid sequence selected from the group consisting of:

(i) the sequence set forth in SEQ ID NO:52;

(ii) a sequence having a substitution, deletion or addition of one or several amino acids (for example, a substitution, deletion or addition of 1, 2, 3, 4 or 5 amino acids) compared to the sequence set forth in SEQ ID NO: 52; or (iii) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 52;

and (b) a light chain comprising an amino acid sequence selected from the group consisting of:

(iv) the sequence set forth in SEQ ID NO:53;

(v) a sequence having a substitution, deletion or addition of one or several amino acids (for example, a substitution, deletion or addition of 1, 2, 3, 4 or 5 amino acids) compared to the sequence set forth in SEQ ID NO: 53; or (vi) a sequence having at least 80%, at least 85%, at least 90%, at least 91%, at least 92%, at least 93%, at least 94%, at least 95%, at least 96%, at least 97%, at least 98%, at least 99%, or 100% identity to the sequence set forth in SEQ ID NO: 53.

In certain preferred embodiments, the substitutions described in (ii) or (v) are conservative substitutions.

In certain exemplary embodiments, the antibodies or antigen-binding fragments thereof of the invention comprise:

(1) a heavy chain having the sequence set forth in SEQ ID NO: 38 and a light chain having the sequence set forth in SEQ ID NO: 39;

(2) a heavy chain having the sequence set forth in SEQ ID NO: 40 and a light chain having the sequence set forth in SEQ ID NO: 41;

(3) a heavy chain having the sequence set forth in SEQ ID NO: 42 and a light chain having the sequence set forth in SEQ ID NO: 43;

(4) a heavy chain having the sequence set forth in SEQ ID NO: 44 and a light chain having the sequence set forth in SEQ ID NO: 45;

(5) a heavy chain having the sequence set forth in SEQ ID NO: 46 and a light chain having the sequence set forth in SEQ ID NO: 47;

(6) a heavy chain having the sequence set forth in SEQ ID NO: 48 and a light chain having the sequence set forth in SEQ ID NO: 49;

(7) a heavy chain having the sequence set forth in SEQ ID NO: 50 and a light chain having the sequence set forth in SEQ ID NO: 51; or (8) A heavy chain having the sequence set forth in SEQ ID NO: 52 and a light chain having the sequence set forth in SEQ ID NO: 53.

In certain preferred embodiments, the antibodies or antigen-binding fragments thereof of the invention are chimeric or humanized antibodies. In certain preferred embodiments, the antibodies or antigen-binding fragments thereof of the invention are selected from the group consisting of scFv, Fab, Fab', (Fab')$_2$, Fv fragment, disulfide-linked Fv (dsFv), diabody, bispecific antibodies, and multispecific antibodies.

The antibodies or antigen-binding fragments thereof of the invention have high specificity and high affinity to LAG-3, especially human LAG-3. In certain preferred embodiments, the antibodies or antigen-binding fragments thereof of the invention are capable of binding to LAG-3 (especially human LAG-3) with a $K_D$ of about $1 \times 10^{-9}$ M or less, such as detecting by biofilm interference technique (BLI) (such as ForteBio Octet®); preferably, the antibodies or antigen-binding fragments thereof of the invention are capable of binding to LAG-3 (especially human LAG-3) with a $K_D$ of about $5 \times 10^{-10}$ M or less.

In certain preferred embodiments, the antibodies or antigen-binding fragments thereof of the invention have at least one of the following biological functions:

(1) specifically recognizing/binding to LAG-3 (especially human LAG-3);

(2) inhibiting and/or blocking the binding of LAG-3 to MHC II, or inhibiting and/or blocking intracellular signaling mediated by LAG-3 binding to MHC II;

(3) inhibiting and/or blocking the binding of LAG-3 to Fibrinogen-like protein 1 (FGL1), or inhibiting and/or blocking intracellular signaling mediated by LAG-3 binding to FGL1;

(4) increasing the activity of immune cells (especially T cells, such as antigen-specific T cells) in vitro and in subjects;

(5) increasing the secretion level of effector cytokines (e.g., IL-2, IFN-γ, etc.), proliferative activity, the expression level of activation markers (e.g., CD25, CD69, etc.), and/or cell killing activity of immune cells (especially T cells, such as antigen-specific T cells) in vitro and in subjects;

(6) enhancing immune response (especially antigen-specific T cell response) in vitro and in subjects;

(7) preventing and/or treating tumors or infections in subjects;

(8) having reduced or eliminated antibody-dependent cell-mediated cytotoxicity (ADCC) and/or complement-dependent cytotoxicity (CDC) in subjects having a tumor;

(9) removing LAG-3 positive immune cells (e.g., LAG-3 positive activated T cells) in subjects with an autoimmune disease;

(10) preventing and/or treating autoimmune diseases in subjects;

(11) inducing antibody-dependent cell-mediated cytotoxicity (ADCC) and/or complement-dependent cytotoxicity (CDC) in subjects having an autoimmune disease.

In certain preferred embodiments, the antibodies or antigen-binding fragments thereof of the invention possess any combination of the above biological functions.

In certain preferred embodiments, the antibodies or antigen-binding fragments thereof of the invention have the biological functions of any one of (1) to (11).

In certain preferred embodiments, the antibodies or antigen-binding fragments thereof of the invention have the biological functions of any one of (1)-(7), (9)-(10).

In certain preferred embodiments, the antibodies or antigen-binding fragments thereof of the invention have the biological functions described in any one of (1) to (7). In certain preferred embodiments, the antibodies or antigen-binding fragments thereof of the invention have the biological functions described in any one of (1) to (8).

In certain preferred embodiments, the antibodies or antigen-binding fragments thereof of the invention have the biological functions of any one of (1), (9)-(10). In certain preferred embodiments, the antibodies or antigen-binding fragments thereof of the invention have the biological functions of any one of (1), (9)-(11).

In certain preferred embodiments, the antibodies or antigen-binding fragments thereof of the invention are derived from the following monoclonal antibody, or are the following monoclonal antibody:

The monoclonal antibody produced by the hybridoma cell line #27, wherein the hybridoma cell line #27 is deposited with the China Center for Type Culture Collection (CCTCC) and has the accession number CCTCC No. C2017183.

In the present disclosure, the antibodies or antigen-binding fragments thereof of the present disclosure may include variants which differ only in one or more amino acid conservative substitutions (for example, up to 20, up to 15, up to 10, up to 5 conservative substitutions) from the antibodies or antigen-binding fragments from which they are derived, or have at least 85%, at least 90%, at least 95%, at least 96%, at least 97%, at least 98%, at least 99%, or 100% sequence identity to the antibodies or antigen-binding fragments from which they are derived, and substantially retain the aforementioned biological functions of the antibodies or antigen-binding fragments from which they are derived.

Derived Antibody

The antibodies or antigen-binding fragments thereof of the invention can be derivatized, for example, linked to another molecule (e.g., another polypeptide or protein). In general, derivatization (e.g., labeling) of the antibodies or antigen-binding fragments thereof do not adversely affect their binding to LAG-3, especially human LAG-3. Thus, the antibodies or antigen-binding fragments thereof of the invention are also intended to include such derivative forms. For example, the antibodies or antigen-binding fragments thereof of the invention can be functionally linked (by chemical coupling, gene fusion, non-covalent attachment or otherwise) to one or more other molecular groups, such as another antibody (e.g., to form a bispecific antibody), a detection reagent, a pharmaceutical agent, and/or a protein or polypeptide (e.g., an avidin or a poly-histidine tag) capable of mediating binding of the antibodies or antigen-binding fragments to another molecule.

One type of derivative antibody (e.g., a bispecific antibody) is produced by cross-linking two or more antibodies (of the same type or different types). Methods for obtaining bispecific antibodies are well known in the art, and examples thereof include, but are not limited to, chemical cross-linking, cell engineering (hybrid hybridoma) or genetic engineering.

Another type of derivative antibody is an antibody that is linked to a therapeutic moiety. The therapeutic moiety of the invention may be a bacterial toxin, a cytotoxic drug or a radioactive toxin, examples of which include, but are not limited to, taxol, cytochalasin B, mitomycin, Etoposide, vincristine or other antimetabolites, alkylating agents, antibiotics or anti-mitotic drugs.

Another type of derivative antibody is labeled antibodies. For example, the antibodies or antigen-binding fragments thereof of the invention can be ligated to a detectable label. The detectable label of the present disclosure can be any substance detectable by fluorescence, spectroscopic, photochemical, biochemical, immunological, electrical, optical or chemical means. Such labels are well known in the art, examples of which include, but are not limited to, enzymes (e.g., horseradish peroxidase, alkaline phosphatase, beta-galactosidase, urease, glucose oxidase, etc.), radionuclides (e.g., $^{3}H$, $^{125}I$, 35S, $^{14}C$ or $^{32}P$), fluorescent dyes (e.g., fluorescein isothiocyanate (FITC), fluorescein, tetramethylrhodamine isothiocyanate (TRITC), phycoerythrin (PE), Texas Red, Rhodamine, quantum dot or cyanine dye derivatives (e.g. Cy7, Alexa 750)), acridinium esters, magnetic beads (e.g. Dynabeads®), calorimetric labels such as colloids gold or tinted glass or plastic (e.g., polystyrene, polypropylene, latex, etc.) beads, and biotin for binding to the above-described marker modified avidin (e.g., streptavidin). Patents that teach the use of such labels include, but are not limited to, U.S. Pat. Nos. 3,817,837, 3,850,752, 3,939,350, 3,996,345, 4,277,437, 4,275,149, and 4,366,241 (all of which are incorporated herein as references). Detectable labels as described above can be detected by methods known in the art. For example, the radioactive label can be detected using a photographic film or a scintillation counter, and the fluorescent label can be detected using a photodetector to detect the emitted light. Enzyme labels are typically detected by providing a substrate for the enzyme and detecting the reaction product produced by the action of the enzyme on the substrate, and the calorimetric label is detected by simply visualizing the stained label. In certain embodiments, such labels can be adapted for immunological detection (e.g., enzyme-linked immunoassay, radioimmunoassay, fluorescent immunoassay, chemiluminescent immunoassay, etc.). In certain embodiments, a detectable label as described above can be linked to the antibodies or antigen-binding fragments thereof of the invention by a linker of varying length to reduce potential steric hindrance.

Furthermore, the antibodies or antigen-binding fragments thereof of the invention may also be derivatized with a chemical group, such as polyethylene glycol (PEG), methyl or ethyl, or a glycosyl group. These groups can be used to improve the biological properties of the antibodies, such as increasing serum half-life.

Hybridoma Cell Line

In another aspect, the invention provides a hybridoma cell line which is:

Hybridoma cell line #27, deposited on Oct. 25, 2017 at the China Center for Type Culture Collection (CCTCC), and having the accession number CCTCC NO. C2017183.

Antibody Preparation

Antibodies of the invention can be prepared by a variety of methods known in the art, such as by genetic engineering recombination techniques. For example, a DNA molecule encoding a heavy chain and a light chain gene of an antibody of the present disclosure is obtained by chemical synthesis or PCR amplification. The resulting DNA molecule is inserted into an expression vector and then transfected into a host cell. The transfected host cells are then cultured under specific conditions and the antibodies of the invention are expressed.

The antigen-binding fragment of the present disclosure can be obtained by hydrolyzing intact antibody molecules (see Morimoto et al., J. Biochem. Biophys. Methods 24: 107-117 (1992) and Brennan et al., Science 229: 81 (1985)). In addition, these antigen-binding fragments can also be produced directly by recombinant host cells (reviewed in Hudson, Curr. Opin. Immunol. 11: 548-557 (1999); Little et al., Immunol. Today, 21: 364-370 (2000)). For example, Fab' fragments can be obtained directly from host cells; Fab' fragments can be chemically coupled to form F(ab')$_2$ fragments (Carter et al., Bio/Technology, 10: 163-167 (1992)). Alternatively, the Fv, Fab or F(ab')$_2$ fragment can be directly isolated from the recombinant host cell culture medium. Other techniques for preparing these antigen-binding fragments are well known to those of ordinary skill in the art.

Accordingly, in another aspect, the invention provides an isolated nucleic acid molecule comprising a nucleotide sequence encoding an antibody or antigen-binding fragment thereof of the invention, or a heavy chain variable region thereof and/or a light chain variable region thereof. In certain preferred embodiments, the isolated nucleic acid molecule encodes an antibody or antigen-binding fragment thereof of the invention, or a heavy chain variable region thereof and/or a light chain variable region thereof.

In certain preferred embodiments, the isolated nucleic acid molecule comprises a first nucleic acid and a second nucleic acid encoding a heavy chain variable region and a light chain variable region of an antibody or antigen-binding fragment thereof of the invention respectively, or comprises a first nucleic acid encoding the variable region and constant region of a heavy chain of an antibody or antigen-binding fragment thereof of the present disclosure and a second nucleic acid encoding the variable region and constant region of a light chain of the antibody or antigen-binding fragment thereof of the present disclosure, or comprises a first nucleic acid and a second nucleic acid encoding the heavy and light chain of the antibody or antigen-binding fragment thereof the present disclosure respectively, or comprises a sequence substantially identical to the aforementioned first nucleic acid and the second nucleic acid; wherein the antibody is selected from any one of the group consisting of: AB12T2, AB12T3, AB12T4, AB12T5, AB12T6, AB12T7, AB12T8. For example, the isolated nucleic acid molecule may comprise the nucleotide sequence set forth in SEQ ID NO: 34, SEQ ID NO: 35 of the Sequence Listing or a sequence substantially identical thereto.

In certain preferred embodiments, the invention provides an isolated nucleic acid molecule comprising a nucleic acid molecule encoding an antibody heavy chain variable region, and/or a nucleic acid molecule encoding an antibody light chain variable region, wherein, the nucleic acid molecule encoding the heavy chain variable region of the antibody has a sequence selected from the group consisting of: (a) a nucleotide sequence as set forth in SEQ ID NO: 34; (b) a sequence substantially identical to the nucleotide sequence of (a) (e.g., a sequence having at least about 85%, 90%, 95%, 99% or more identity to the nucleotide sequence of (a), or a sequence having one or more nucleotide substitutions), (c) a sequence which differs from the nucleotide sequence of (a) by no more than 3, 6, 15, 30 or 45 nucleotides; the nucleic acid molecule encoding the light chain variable region of the antibody has a sequence selected from the group consisting of: (d) a nucleotide sequence as set forth in SEQ ID NO: 35; (e) a sequence substantially identical to the nucleotide sequence of (d) (e.g., a sequence having at least about 85%, 90%, 95%, 99% or more identity to the nucleotide sequence of (d), or a sequence having one or more nucleotide substitutions), (f) a sequence which differs from the nucleotide sequence of (d) by no more than 3, 6, 15, 30 or 45 nucleotides.

In certain preferred embodiments, the nucleic acid molecule encoding an antibody heavy chain variable region comprises a nucleotide sequence as set forth in SEQ ID NO: 34, and the nucleic acid molecule encoding the antibody light chain variable region comprises a nucleotide sequence as shown in SEQ ID NO:35. In certain preferred embodiments, an isolated nucleic acid molecule of the invention comprises a nucleic acid molecule as set forth in SEQ ID NO: 34 which encodes an antibody heavy chain variable region, and/or a nucleic acid molecule as set forth in SEQ ID NO: 35 which encodes the variable region of an antibody light chain.

In another aspect, the invention provides a vector (e.g., a cloning vector or an expression vector) comprising an isolated nucleic acid molecule of the invention. In certain preferred embodiments, the vectors of the invention are, for example, plasmids, cosmids, phages, and the like. In certain preferred embodiments, the vector is capable of expressing an antibody or antigen-binding fragment thereof of the invention in a subject, such as a mammal, such as a human.

In another aspect, the invention provides a host cell comprising an isolated nucleic acid molecule of the invention or a vector of the invention. Such host cells include, but are not limited to, prokaryotic cells such as E. coli cells, and eukaryotic cells such as yeast cells, insect cells, plant cells, and animal cells (e.g., mammalian cells, such as mouse cells, human cells, etc.). In certain preferred embodiments, the host cell of the invention is a mammalian cell, such as CHO (e.g., CHO-K1, CHO-S, CHO DG44).

In another aspect, the invention provides a method of producing an antibody or antigen-binding fragment thereof of the invention, comprising culturing a host cell of the invention under conditions which permit expression of the antibody or antigen-binding fragment thereof, and recovering the antibody or antigen-binding fragment thereof from the cultured host cell culture.

Therapeutic Methods and Drug Combinations

The antibody or antigen-binding fragment thereof of the present disclosure can be used in vitro or in a subject to inhibit and/or block intracellular signaling mediated by LAG-3 binding to MHC II and/or FGL1, enhance immune cell activity, and enhance immunity response, as well as for preventing and/or treating a disease associated with an immune abnormality (e.g., a tumor, an infection, or an autoimmune disease), or as an immunological adjuvant.

Accordingly, in another aspect, the present disclosure provides a pharmaceutical composition comprising an antibody of the present disclosure, or an antigen-binding fragment thereof, or a prodrug thereof (e.g., probody), and a pharmaceutically acceptable carrier and/or excipient.

In certain preferred embodiments, the pharmaceutical composition may also comprise an additional pharmaceutically active agent. In certain preferred embodiments, the additional pharmaceutically active agent is a drug having anti-tumor activity. In certain preferred embodiments, the additional pharmaceutically active agent is a drug for treating infection. In certain preferred embodiments, the additional pharmaceutically active agent is a medicament for the treatment of an autoimmune disease.

In certain preferred embodiments, the antibody or antigen-binding fragment thereof of the invention and the additional pharmaceutically active agent are provided as separate components or as components of a single composition, in the pharmaceutical composition. Thus, an antibody or antigen-binding fragment thereof of the invention and the additional pharmaceutically active agent can be administered simultaneously, separately or sequentially.

In another aspect, the pharmaceutical composition of the present disclosure further comprises a second antibody or a nucleic acid encoding the second antibody that specifically binds to a receptor or ligand selected from the group consisting of: PD-1, PD-L1, PD-L2, TIM-3, TIGIT, VISTA, CTLA-4, OX40, BTLA, 4-1BB, CD96, CD27, CD28, CD40, LAIR1, CD160, 2B4, TGF-R, KIR, ICOS, GITR, CD3, CD30, BAFFR, HVEM, CD7, LIGHT, SLAMF7, NKp80, B7-H3, and any combination thereof.

In certain specific embodiments, the second antibody is an antibody or antigen-binding fragment thereof that binds to human PD-1. In certain preferred embodiments, the pharmaceutical compositions of the invention comprise an antibody or antigen-binding fragment thereof that binds to human PD-1.

In certain preferred embodiments, the antibody or antigen-binding fragment thereof that binds to human PD-1 comprised in the pharmaceutical composition of the invention is selected from the group consisting of: AB12M4 or an antigen-binding fragment thereof, Nivolumab (Opdivo®) or an antigen-binding fragment thereof, and Pembrolizumab (Keytruda®) or an antigen-binding fragment thereof. AB12M4 can be found in Chinese patent application CN106519034A.

In certain preferred embodiments, the antibody or a binding antigen fragment thereof that binds to human PD-1 comprised in the pharmaceutical composition of the invention is AB12M4.

In certain specific embodiments, the second antibody is an antibody or antigen-binding fragment thereof that binds to human PD-L1. In certain preferred embodiments, the pharmaceutical compositions of the invention comprise an antibody or antigen-binding fragment thereof that binds to human PD-L1.

In another aspect, the invention provides an immunogenic composition comprising an antibody or antigen-binding fragment thereof of the invention, and an immunogen.

In certain preferred embodiments, an antibody of the invention or antigen-binding fragment thereof is used as an adjuvant.

In certain preferred embodiments, the immunogen is selected from a tumor-associated antigen (e.g., a protein, polypeptide or carbohydrate molecule), a tumor cell, a dendritic cell sensitized by the antigen, and any combination thereof.

In certain preferred embodiments, the immunogen is selected from a pathogen- (e.g., a virus-) associated antigen (e.g., a protein, polypeptide or carbohydrate molecule), an inactivated or attenuated pathogen, a dendritic cell sensitized by the antigen, and any combination thereof.

In some preferred embodiments, the immunogenic composition also includes a pharmaceutically acceptable carrier and/or excipient. In some preferred embodiments, the immunogenic composition includes a stabilizer.

In some preferred embodiments, in the immunogenic composition, the antibody or antigen binding fragment of the present disclosure and the immunogen are provided as separated components or as components of a single composition. Therefore, the antibody or its antigen binding fragment of the invention and the immunogen may be administered simultaneously, separately or successively.

In another aspect, the invention relates to the use of antibodies or their antigen binding fragments, pharmaceutical compositions or immunogenic compositions of the present disclosure in the preparation of drugs for:

(1) improving the activity of immune cells in vitro or in a subject (e.g. a human);

(2) enhancing the immune response in a subject (e.g. a human);

(3) preventing and/or treating a tumor in a subject (e.g. a human;

(4) preventing and/or treating an infection in a subject (e.g. a human);

(5) preventing and/or treating an autoimmune disease in a subject (e.g. a human).

In another aspect, the invention relates to the use of an antibody or antigen binding fragment of the present disclosure as an adjuvant, or in the preparation of an immunogenic composition for enhancing immune response in a subject; wherein, the immunogenic composition comprises an antibody or an antigen binding fragment thereof of the present disclosure and an immunogen.

In certain preferred embodiments, the immunogen is selected from a tumor-associated antigen (e.g., a protein, polypeptide or carbohydrate molecule), a tumor cell, a dendritic cell sensitized by the antigen, and any combination thereof. In such embodiments, the immunogenic composition is for use in preventing and/or treating a tumor in a subject.

In certain preferred embodiments, the immunogen is selected from a pathogen- (e.g., a virus-) associated antigen (e.g., a protein, polypeptide or carbohydrate molecule), an inactivated or attenuated pathogen, a dendritic cell sensitized by the antigen, and any combination thereof. In such embodiments, the immunogenic composition is for use in preventing and/or treating an infection in a subject.

In certain preferred embodiments, the immunogenic composition further comprises a pharmaceutically acceptable carrier and/or excipient. In certain preferred embodiments, the immunogenic composition comprises a stabilizer.

In another aspect, the invention provides a method of increasing immune cell activity in vitro, the method comprises the step of contacting the immune cell with an antibody or antigen-binding fragment thereof of the invention. In such embodiments, an antibody or antigen-binding fragment thereof of the invention may have reduced or even eliminated ADCC and/or CDC activities.

In certain preferred embodiments, any suitable indicator can be used to measure the activity of the immune cells. Non-limiting examples of such suitable indicators include increased secretion level of cytokines (e.g., IL-2, IFN-γ, etc.), increased proliferative activity, and/or increased expression level of activation marker (e.g., CD25, CD69, etc.) of immune cells (e.g., T cells) in the presence of an antibody or antigen-binding fragment thereof of the present disclosure.

In certain preferred embodiments, the method is for treating a tumor. In such embodiments, the immune cells obtained by the above methods can be adoptively transferred to ta subject in to treat a tumor. In vitro activation by an antibody of the invention or an antigen-binding fragment thereof is expected to increase the activity of adoptively transferred immune cells, thereby facilitating tumor killing of these adoptively transferred immune cells in a subject. In certain preferred embodiments, the immune cell is a tumor infiltrating lymphocyte.

In certain preferred embodiments, the method further comprises the step of contacting the immune cell with an additional pharmaceutically active agent, which may be selected from an immune response stimulator, such as an immunostimulatory cytokine or an additional immunostimulatory antibody. In certain exemplary embodiments, the immunostimulatory cytokine is selected from, for example, IL-2, IL-3, IL-12, IL-15, IL-18, IFN-γ, IL-10, TGF-β, GM-CSF, and any combination thereof. In certain exemplary embodiments, the immunostimulatory antibody is selected from an antibody or antigen-binding fragment thereof that binds to human PD-1, or an antibody or antigen-binding fragment thereof that binds to human PD-L1.

In another aspect, the invention provides a method of increasing immune cell activity and/or enhancing an immune response in a subject, the method comprising administering to a subject in need an effective amount of an antibody of the invention (or an antigen binding fragment thereof), a pharmaceutical composition of the invention or an immunogenic composition of the invention. In such embodiments, an antibody or antigen-binding fragment thereof of the invention may have reduced or even eliminated ADCC and/or CDC activities.

In certain preferred embodiments, the immune response is a specific immune response (e.g., an antigen-specific T cell response).

In certain preferred embodiments, the methods are for preventing and/or treating a tumor. In such embodiments, the subject has a tumor.

In certain preferred embodiments, the methods are for preventing and/or treating an infection. In such embodiments, the subject has an infection. In certain preferred embodiments, the infection is a viral infection, such as a chronic viral infection.

In certain preferred embodiments, the immune cell is a T cell, such as a cytotoxic T cell (CTL) or antigen-specific T cell. In certain preferred embodiments, the immune cell is a tumor infiltrating lymphocyte.

In certain preferred embodiments, an antibody of the invention (or antigen-binding fragment thereof) is administered in combination with an additional pharmaceutically active agent. Such additional pharmaceutically active agents can be administered prior to, concurrently with, or subsequent to administration of an antibody (or antigen-binding fragment thereof) of the present disclosure. In certain preferred embodiments, the additional pharmaceutically active agent is a drug having immunostimulatory activity, such as an immunostimulatory antibody.

In certain preferred embodiments, an antibody of the invention (or antigen-binding fragment thereof) is administered in combination with a second antibody that specifically binds to a receptor or ligand selected from the group consisting of PD-1, PD-L1, PD-L2, TIM-3, TIGIT, VISTA, CTLA-4, OX40, BTLA, 4-1BB, CD96, CD27, CD28, CD40, LAIR1, CD160, 2B4, TGF-R, KIR, ICOS, GITR, CD3, CD30, BAFFR, HVEM, CD7, LIGHT, SLAMF7, NKp80, B7-H3, and any combination thereof. The second antibody can be administered prior to, concurrently with, or subsequent to administration of an antibody (or antigen-binding fragment thereof) of the invention.

In certain exemplary embodiments, an antibody of the invention (or antigen-binding fragment thereof) is administered in combination with an antibody or an antigen-binding fragment thereof that binds to human PD-1. In certain preferred embodiments, the antibody or antigen-binding fragment thereof that binds human PD-1 is selected from the group consisting of AB12M4 or an antigen-binding fragment thereof, Nivolumab (Opdivo®) or antigen-binding fragment thereof, and Pembrolizumab (Keytruda®) or antigen-binding fragments thereof. In certain preferred embodiments, the antibody or a binding antigen fragment thereof that binds to human PD-1 is AB12M4.

In certain exemplary embodiments, an antibody (or antigen-binding fragment thereof) of the present disclosure is administered in combination with an antibody or antigen-binding fragment thereof that binds to human PD-L1.

In another aspect, the invention provides a method for preventing and/or treating a tumor in a subject (e.g., a human). The methods comprise administering to a subject in need thereof an effective amount of an antibody (or antigen-binding fragment thereof) of the present disclosure, a pharmaceutical composition of the invention, or an immunogenic composition of the invention. In such embodiments, an antibody or antigen-binding fragment thereof of the invention may have reduced or even eliminated ADCC and/or CDC activities.

In certain preferred embodiments, an antibody of the invention (or antigen-binding fragment thereof) is administered in combination with an additional pharmaceutically active agent, such as in combination with an additional agent having anti-tumor activity.

In certain preferred embodiments, the additional pharmaceutically active agent is a toxin, a cytotoxic agent, a radioisotope, an immunosuppressant, or a vaccine. The anti-LAG-3 antibody or antigen-binding fragment thereof of the invention can be linked to the additional pharmaceutically active agent (as an immune complex) or administered separately from the additional pharmaceutically active agent. In the latter case, the anti-LAG-3 antibody or antigen-binding fragment thereof of the invention may be administered before, after, or simultaneously with the administering of an additional pharmaceutically active agent, or can be combined with other known therapies (e.g., anti-cancer therapies, such as radiation).

In certain preferred embodiments, additional pharmaceutically active agent therapeutics include, but are not limited to, antineoplastic agents such as doxorubicin (doxorubicin), cisplatin, bleomycin sulfate, nitrosourea nitrogen Mustard, chlorambucil and cyclophosphamide hydroxyurea, these therapeutic agents themselves are effective only when they have toxic or subtoxic levels to the patient. A target-specific effector cell, such as an effector cell linked to an anti-LAG-3 antibody or antigen-binding fragment thereof of the present disclosure, can also be used as a therapeutic agent. The target-specific effector cells can be human leukocytes, such as macrophages, neutrophils or monocytes. Other cells include eosinophils, NK cells, and other cells bearing IgG or IgA receptors. If desired, effector cells can be obtained from the subject to be treated. The target-specific effector cells can be administered as a suspension of cells in a physiologically acceptable solution. The amount of cells administered can range in the order of $10^8$-$10^9$, but can vary depending on the purpose of the treatment. In general, this amount is sufficient to achieve localization of the targeted cells (such as cells expressing tumors of LAG-3), and cell killing by, for example, phagocytosis. The route of administration can also be different, including oral, rectal, transmucosal, enteral, parenteral; intramuscular, subcutaneous, intradermal, intramedullary, intrathecal, direct ventricular, intravenous, intraperitoneal, intranasal, intraocular, inhalation, insufflation, topical, skin, percutaneous or intra-arterial.

Where complements are present, a composition of the invention having a complement binding site, such as a portion from IgG1, IgG2 or IgG4 or IgM bound to complement, can also be used. Compositions of the invention may also be administered with complement, for example in combination with C1q.

Therapy of target-specific effector cells can be performed in conjunction with other techniques for clearing targeted cells. For example, anti-tumor therapies using the compositions of the invention and/or effector cells equipped with such compositions are used in combination with chemotherapy. Non-limiting examples of therapies in combination with the antibodies of the invention include surgery, chemotherapy, radiation therapy, immunotherapy, gene therapy, DNA therapy, RNA therapy, nanotherapy, viral therapy, adjuvant therapy, and any combination thereof.

The determination of the appropriate dose is by a clinician, for example using parameters or factors known or suspected to affect treatment in the art. Typically, the dose begins with an amount that is slightly less than the optimal dose, and then is increased in smaller increments until the desired or optimal effect is achieved relative to any negative side effects. Important diagnostic measures include, for example, a measure of the symptoms of inflammation or the level of inflammatory cytokine produced.

In certain preferred embodiments, an antibody of the invention (or antigen-binding fragment thereof) is administered in combination with a second antibody that specifically binds to a receptor or ligand selected from the group consisting of PD-1, PD-L1, PD-L2, TIM-3, TIGIT, VISTA, CTLA-4, OX40, BTLA, 4-1BB, CD96, CD27, CD28, CD40, LAIR1, CD160, 2B4, TGF-R, KIR, ICOS, GITR, CD3, CD30, BAFFR, HVEM, CD7, LIGHT, SLAMF7, NKp80, B7-H3, and any combination thereof. The second antibody can be administered prior to, concurrently with, or subsequent to administration of an antibody (or antigen-binding fragment thereof) of the invention.

In certain exemplary embodiments, an antibody of the invention (or antigen-binding fragment thereof) is administered in combination with an antibody or an antigen-binding fragment thereof that binds to human PD-1. In certain preferred embodiments, the antibody or antigen-binding fragment thereof that binds human PD-1 is selected from the group consisting of AB12M4 or an antigen-binding fragment thereof, Nivolumab (Opdivo®) or antigen-binding fragment thereof, and Pembrolizumab (Keytruda®) or antigen-binding fragment thereof. In certain preferred embodiments, the antibody or a binding antigen fragment thereof that binds to human PD-1 is AB12M4.

In certain exemplary embodiments, an antibody (or antigen-binding fragment thereof) of the invention is administered in combination with an antibody or antigen-binding fragment thereof that binds to human PD-L1.

In certain preferred embodiments, an antibody (or antigen-binding fragment thereof), pharmaceutical composition or immunogenic composition of the invention is administered in combination with additional anti-tumor therapy. Such additional anti-tumor therapy can be any therapy known for use in tumors, such as surgery, chemotherapy, radiation therapy, targeted therapy, immunotherapy, hormone therapy, gene therapy, or palliative care. Such additional anti-tumor therapy can be administered prior to, concurrently with, or subsequent to administration of the antibody (or antigen-binding fragment thereof), pharmaceutical composition or immunogenic composition of the present disclosure.

In another aspect, the invention provides a method for preventing and/or treating an infection in a subject (e.g., a human). The methods comprise administering to a subject in need thereof an effective amount of an antibody (or antigen-binding fragment thereof) of the invention, a pharmaceutical composition of the invention, or an immunogenic composition of the invention. In such embodiments, an antibody or antigen-binding fragment thereof of the invention may have reduced or even eliminated ADCC and/or CDC activities.

In certain preferred embodiments, an antibody of the invention (or antigen-binding fragment thereof) is administered in combination with an additional agent for treating an infection. Such additional drugs for treating infection can be administered prior to, concurrently with, or subsequent to administration of the antibody (or antigen-binding fragment thereof).

In certain preferred embodiments, an antibody of the invention (or antigen-binding fragment thereof) is administered in combination with a second antibody that specifically binds to a receptor or ligand selected from the group consisting of PD-1, PD-L1, PD-L2, TIM-3, TIGIT, VISTA, CTLA-4, OX40, BTLA, 4-1BB, CD96, CD27, CD28, CD40, LAIR1, CD160, 2B4, TGF-R, KIR, ICOS, GITR, CD3, CD30, BAFFR, HVEM, CD7, LIGHT, SLAMF7, NKp80, B7-H3, and any combination thereof. The second antibody can be administered prior to, concurrently with, or subsequent to administration of an antibody (or antigen-binding fragment thereof) of the present disclosure.

In certain exemplary embodiments, an antibody of the invention (or antigen-binding fragment thereof) is administered in combination with an antibody or an antigen-binding fragment thereof that binds to human PD-1. In certain preferred embodiments, the antibody or antigen-binding fragment thereof that binds human PD-1 is selected from the group consisting of AB12M4 or an antigen-binding fragment thereof, Nivolumab (Opdivo®) or antigen-binding fragment thereof, and Pembrolizumab (Keytruda®) or antigen-binding fragment thereof. In certain preferred embodiments, the antibody or a binding antigen fragment thereof that binds to human PD-1 is AB12M4.

In certain exemplary embodiments, an antibody (or antigen-binding fragment thereof) of the invention is administered in combination with an antibody or antigen-binding fragment thereof that binds to human PD-L1.

In certain preferred embodiments, an antibody (or antigen-binding fragment thereof) of the invention is administered in combination with a vaccine. In certain preferred embodiments, the vaccine may be a pathogen-associated antigen (e.g., a protein, polypeptide or carbohydrate molecule), an inactivated or attenuated pathogen, an antigen-sensitized dendritic cell, or any combination thereof. In certain preferred embodiments, the pathogen can be a virus (e.g., hepatitis A, B, C virus, human immunodeficiency virus, human papilloma virus, or herpes virus), fungus, bacteria, or parasite.

In another aspect, the invention provides a method for preventing and/or treating an autoimmune disease in a subject (e.g., a human). The methods comprise administering to a subject in need thereof an effective amount of an antibody (or antigen-binding fragment thereof) of the present disclosure, a pharmaceutical composition of the invention, or an immunogenic composition of the invention. In such embodiments, an antibody or antigen-binding fragment thereof of the invention can have ADCC and/or CDC activities.

In certain preferred embodiments, the antibodies (or antigen-binding fragments thereof) of the invention are used in combination with additional agents having activity to treat autoimmune diseases. Such additional agents having activity in the treatment of autoimmune diseases can be administered prior to, concurrently with, or subsequent to administration of the antibody (or antigen-binding fragment thereof).

In the present disclosure, non-limiting examples of the tumors include ovarian cancer, melanoma (for example, metastatic malignant melanoma), prostate cancer, intestinal cancer (for example, colorectal cancer and cancer of small intestine), gastric cancer, esophageal cancer, breast cancer, lung cancer, kidney cancer (e.g., clear cell carcinoma), pancreatic cancer, uterine cancer, liver cancer, bladder cancer, cervical cancer, oral cancer, brain cancer, testicular cancer, skin cancer, thyroid cancer, and hematology malignant tumors including myeloma and chronic and acute leukemia.

In the present disclosure, the infection refers to any infection caused by any pathogenic microorganism such as a virus, a bacterium, a fungus, a parasite or the like. Non-limiting examples of the virus include hepatitis A, B, C virus, human immunodeficiency virus, human papilloma virus or herpes virus, etc.; non-limiting examples of such bacteria include *Chlamydia, Mycobacterium, Staphylococcus, Streptococcus*, pneumococcus, meningococcus, etc.; non-limiting examples of the fungus include *Trichophyton, Epidermophyton, Microsporum, Candida albicans, Cryptococcus neoformans*, etc.; non-limiting examples of parasites include *Plasmodium, Schistosoma, Leishmania donovani, Filaria*, hookworm, and the like.

In the present disclosure, non-limiting examples of the autoimmune diseases include rheumatoid arthritis, psoriasis, systemic lupus erythematosus, primary biliary cirrhosis, autoimmune hemolytic anemia, autoimmune thrombocytopenic purpura, insulin-dependent diabetes mellitus, Graves' disease, myasthenia gravis, autoimmune hepatitis, and multiple sclerosis.

Antibodies or antigen binding fragments of the present disclosure, pharmaceutical compositions of the present disclosure or immunogenic compositions of the present disclosure may be formulated into any dosage form known in the medical field, for example, tablets, pills, suspensions, emulsions, solutions, gels, capsules, powders, granules, elixirs, lozenges, suppositories, injections (including injection, sterile powder for injection and concentrated solution for injection), inhalation, spray, etc. The preferred dosage form depends on the expected mode of administration and therapeutic use. The pharmaceutical composition of the invention should be sterile and stable under production and storage conditions. One preferred dosage form is injection. Such injections can be aseptic injection solutions. For example, an aseptic injection solution may be prepared by mixing an appropriate solvent with a necessary dose of recombinant protein of the present disclosure, and optionally, with other desired components (including, but not limited to, pH regulators, surfactants, adjuvants, ionic strength enhancers, isotonic agents, preservatives, diluents, or any combination thereof), followed by filtration and sterilization. In addition, aseptic injection solutions can be prepared as aseptic freeze-dried powders (for example, by vacuum drying or freeze-drying) for easy storage and use. Such aseptic freeze-dried powders can be dispersed in suitable carriers before use, such as aseptic and pyrogen-free water.

In addition, the antibody or antigen binding fragment of the invention may be present in the pharmaceutical composition or immunogenic composition in the form of a unit dose to facilitate administration.

Antibodies or their antigen binding fragments, pharmaceutical compositions or immunogenic compositions of the present disclosure may be administered by any suitable method known in the art, including, but not limited to, oral, buccal, sublingual, eyeball, local, parenteral, rectal, intrathecal, intra-cytoplasmic, groin, intravesical, local (e.g., powder, ointment or drop), or nasal route. However, for many therapeutic uses, the preferred route/mode of administration is parenteral administration (e.g. intravenous injection, subcutaneous injection, intraperitoneal injection, intramuscular injection). Technicians should understand that the route and/or manner of administration will change according to the intended purpose. In a preferred embodiment, antibodies or their antigen binding fragments, pharmaceutical compositions or immunogenic compositions of the present disclosure are given by intravenous infusion or injection.

The pharmaceutical composition or immunogenic composition of the present disclosure may include an antibody or an antigen binding fragment of the present disclosure with a "therapeutically effective amount" or a "prophylactically effective amount". "Prophylactically effective amount" means the amount sufficient to prevent, arrest, or delay the occurrence of disease. "Therapeutically effective amount" means the amount sufficient to cure or at least in part prevent the disease and complications of the patient who already has the disease. The therapeutically effective amount of the antibody or its antigen binding fragment of the present disclosure may vary according to the severity of the disease to be treated, the overall state of the patient's own immune system, and the general conditions of the patient, such as age, body weight and sex, the manner in which the drug is administered, as well as other treatments used simultaneously, and so on.

In the present disclosure, the administration scheme can be adjusted to obtain an optimal intended response (e.g., therapeutic or preventive response). For example, it may be administered in a single administration, or be administered multiple times over a period of time, or be proportionally reduced or increased depending on the urgency of the treatment.

A typical non-limiting range of therapeutically or prophylactically effective amounts of the recombinant protein of the invention is from 0.02 to 100 mg/kg, such as from 0.1 to 100 mg/kg, from 0.1 to 50 mg/kg, or from 1 to 50 mg/kg. It should be noted that the dosage may vary depending on the type and severity of the condition to be treated. Moreover, those skilled in the art understand that for any particular patient, the particular dosage regimen should be adjusted over time according to the needs of the patient and the professional evaluation of the physician; the dosage ranges given herein are for illustrative purposes only and don't limit usage or range of a pharmaceutical or immunogenic composition of the invention.

In the present disclosure, the subject may be a mammal, such as a human.

The present disclosure provides a container (e.g., a plastic or glass vial, such as a cap or chromatography column, a hollow well needle or a syringe barrel), that contains any of the antibodies or antigen-binding fragments of the invention, or a pharmaceutical composition. The invention also provides an injection device containing any of the antibodies or antigen-binding fragments of the invention, or a pharmaceutical composition.

Detection Method and Kit

The antibodies or antigen-binding fragments thereof of the invention are capable of specifically binding to LAG-3 and thus can be used to detect the presence or level of LAG-3 in a sample.

Thus, in another aspect, the invention provides a kit containing an antibody or an antigen binding fragment thereof of the invention. In certain preferred embodiments, an antibody or antigen-binding fragment thereof of the invention carries a detectable label. In a preferred embodiment, the kit further contains a second antibody that specifically recognizes an antibody or antigen-binding fragment thereof of the invention. Preferably, the second antibody further has a detectable label.

In the present disclosure, the detectable label may be any substance detectable by fluorescence, spectroscopic, photochemical, biochemical, immunological, electrical, optical or chemical means. It is particularly preferred that such labels are suitable for use in immunological assays (e.g., enzyme-linked immunoassays, radioimmunoassays, fluorescent immunoassays, chemiluminescent immunoassays, etc.). Such labels are well known in the art and include, but are not limited to, enzymes (e.g., horseradish peroxidase, alkaline phosphatase, beta-galactosidase, urease, glucose oxidase, etc.), radionuclides (for example, $^3H$, $^{125}I$, $^{35}S$, $^{14}C$ or $^{32}P$), fluorescent dyes (e.g., fluorescein isothiocyanate (FITC), fluorescein, tetramethylrhodamine isothiocyanate (TRITC), phycoerythrin (PE), Texas Red, Rhodamine, quantum dot or cyanine dye derivatives (e.g. Cy7, Alexa 750)), acridine esters, magnetic beads (e.g., Dynabeads®), calorimetric labels such as colloidal gold or Colored glass or plastic (e.g., polystyrene, polypropylene, latex, etc.) beads, and biotin for binding to the above-described label modified avidin (e.g., streptavidin). Patents that teach the use of such labels include, but are not limited to, U.S. Pat. Nos. 3,817,837, 3,850,752, 3,939,350, 3,996,345, 4,277,437, 4,275,149, and 4,366,241, each of which is incorporated herein by reference. The labels encompassed in the present disclosure can be detected by methods known in the art. For example, the radioactive label can be detected using a photographic film or a scintillation counter, and the fluorescent label can be detected using a photo-detector to detect the emitted light. Enzyme labels are typically detected by providing a substrate for the enzyme and detecting the reaction product produced by the action of the enzyme on the substrate, and the calorimetric label is detected by simply visualizing the stained label. In certain embodiments, a detectable label as described above can be linked to a recombinant protein of the invention by a linker of varying length to reduce potential steric hindrance.

In another aspect, the invention provides a method of detecting the presence or level of LAG-3 in a sample comprising the step of using an antibody or antigen-binding fragment thereof of the invention. In a preferred embodiment, the antibodies or antigen-binding fragments thereof of the invention also carry a detectable label. In another preferred embodiment, the method further comprises detecting the antibody or antigen-binding fragment thereof of the invention using a reagent with a detectable label. The method can be used for diagnostic purposes, or for non-diagnostic purposes (e.g., the sample is a cell sample, not a sample from a patient).

In another aspect, there is provided the use of an antibody or antigen-binding fragment thereof of the invention in the preparation of a kit for detecting the presence or level of LAG-3 in a sample.

Abbreviations and Definitions of Terms

The following abbreviations are used in this context:
CDR Complementarity determining region in immunoglobulin variable region
FR Antibody framework region: amino acid residues other than CDR residues in the variable region of an antibody
VH Antibody heavy chain variable region
VL Antibody light chain variable region
IgG Immunoglobulin G
Kabat Immunoglobulin alignment and numbering system proposed by Elvin A. Kabat (see, for example, Kabat et al., Sequences of Proteins of Immunological Interest, 5th Ed. Public Health Service, National Institutes of Health, Bethesda, Md., 1991).
Chothia An immunoglobulin numbering system proposed by Chothia et al., which is a classical rule for identifying the boundaries of CDR regions based on the position of the structural loop region (see, for example, Chothia & Lesk (1987) J. Mol. Biol. 196:901-917; Chothia Et al. (1989) Nature 342: 878-883).
IMGT A numbering system based on The international ImMuno GeneTics information system (IMGT), initiated by Lefranc et al., see Lefranc et al., Dev. Comparat. Immunol. 27: 55-77, 2003.
mAb Monoclonal antibody
EC50 A concentration at which 50% efficacy or binding is produced
IC50 A concentration at which 50% inhibition is produced
ELISA Enzyme linked immunosorbent assay
PCR Polymerase chain reaction
HRP Horseradish peroxidase
IL-2 Interleukin-2
IFN Interferon
$K_D$ Equilibrium dissociation constant
kon Binding rate constant
kdis Dissociation rate constant In the present disclosure, the scientific and technical terms used herein have the meanings commonly understood by those skilled in the art, unless otherwise stated. Moreover, the steps of cell culture, biochemistry, nucleic acid chemistry, immunology laboratories and the like used herein are routine steps widely used in the corresponding fields. Also, for a better understanding of the present disclosure, definitions and explanations of related terms are provided below.

As used herein, the term "antibody" refers to an immunoglobulin molecule that is typically composed of two pairs of polypeptide chains, each pair having one light chain (LC) and one heavy chain (HC). Antibody light chains can be classified as κ (kappa) and λ (lambda) light chains. Heavy chains can be classified as δ, γ, α, or ε, and the isotypes of antibodies are defined as IgM, IgD, IgG, IgA, and IgE, respectively. Within the light and heavy chains, the variable and constant regions are joined by a "J" region of about 12 or more amino acids, and the heavy chain further comprises a "D" region of about 3 or more amino acids. Each heavy chain consists of a heavy chain variable region (VH) and a heavy chain constant region (CH). The heavy chain constant region consists of three domains (CH1, CH2 and CH3). Each light chain consists of a light chain variable region (VL) and a light chain constant region (CL). The light chain constant region consists of one domain CL. The constant domain is not directly involved in the binding of the antibody to the antigen, but exhibits multiple effector functions, such as mediating binding of immunoglobulins with host tissues or factors, including various immune cells (e.g., effector cells) and classical complement system's first component (C1q). The VH and VL regions can further be subdivided into regions with high variability (referred to as complementarity determining regions (CDRs)) interspersed within more conserved regions called framework regions (FR). Each of VH and VL is composed of three CDRs and four FRs arranged in the following order: FR1, CDR1, FR2, CDR2, FR3, CDR3, FR4 from the amino terminus to the carboxy terminus. The variable regions (VH and VL) of each heavy/light chain pair form an antigen binding site, respectively. The assignment of amino acids in each region or domain may be in accordance with Kabat, Sequences of Proteins of Immunological Interest (National Institutes of Health, Bethesda, Md. (1987 and 1991)), or Chothia & Lesk (1987) J. Mol. Biol.: 901-917; Chothia et al. (1989) Nature 342: 878-883.

As used herein, the term "complementarity determining region" or "CDR" refers to the amino acid residues in the variable region of an antibody that is responsible for antigen binding. The precise boundaries of these amino acid residues can be defined according to various numbering systems known in the art, for example, according to the Kabat numbering system (Kabat et al., Sequences of Proteins of Immunological Interest, 5th Ed. Public Health Service, National Institutes of Health, Bethesda, Md., 1991), Chothia numbering system (Chothia & Lesk (1987) J. Mol. Biol. 196:901-917; Chothia et al. (1989) Nature 342:878-883) or IMGT numbering system (Definitions in Lefranc et al., Dev. Comparat. Immunol. 27:55-77, 2003). Those skilled in the art will readily identify the CDRs defined by each numbering system for a given antibody. Moreover, the correspondence between different numbering systems is well known to those skilled in the art (see, for example, Lefranc et al., Dev. Comparat. Immunol. 27: 55-77, 2003).

In the present disclosure, the CDRs of the antibody or antigen-binding fragment thereof of the present disclosure can be determined according to various numbering systems known in the art. In certain embodiments, the CDRs of the antibodies or antigen-binding fragments thereof of the present disclosure are preferably determined by the Kabat, Chothia or IMGT numbering system.

As used herein, the term "framework region" or "FR" residue refers to those amino acid residues in the variable regions of an antibody other than the CDR residues as defined above.

As used herein, the term "germline antibody gene" is an immunoglobulin sequence encoded by a non-lymphocyte that has not undergone a maturation process leading to the genetic rearrangement and maturation for expression of a specific immunoglobulin. One advantage provided by various embodiments of the present disclosure stems from the recognition that the germline antibody gene retains more of the characteristic important amino acid sequence structure of an individual of an animal species than a mature antibody gene. Therefore, when therapeutically applied to the species, it is less likely to be recognized by the species as a foreign substance.

The term "antibody" is not limited by any particular method of producing antibodies. For example, it includes recombinant antibodies, monoclonal antibodies, and polyclonal antibodies. The antibodies may be antibodies of different isotypes, for example, IgG (e.g., IgG1, IgG2, IgG3 or IgG4 subtype), IgA1, IgA2, IgD, IgE or IgM antibodies.

As used herein, the term "antigen-binding fragment" of an antibody refers to a polypeptide fragment of an antibody, such as a polypeptide fragment of a full length antibody that retains the ability to specifically bind to the same antigen to which the full length antibody binds, and/or competes with the full length antibody to specifically bind to the antigen, which is also referred to as an "antigen binding portion." See generally, Fundamental Immunology, Ch. 7 (Paul, W., ed., 2nd ed., Raven Press, NY (1989), which is incorporated herein by reference in its entirety for all purposes. An antigen-binding fragment of an antibody may be produced by recombinant DNA technology or by enzymatic or chemical cleavage of an intact antibody. Non-limiting examples of antigen-binding fragments include Fab, Fab', F(ab')2, Fd, Fv, dAb and complementarity determining regions (CDRs) fragments, single-chain antibodies (eg, scFv), chimeric antibodies, diabody, linear antibodies, nanobodies (such as from Ablynx), domain antibodies (such as from Domantis), and a polypeptide comprising at least a portion of an antibody sufficient to confer specific antigen binding ability to the polypeptide. Engineered antibody variants are reviewed in Holliger et al, 2005; Nat Biotechnol, 23: 1126-1136.

As used herein, the term "full length antibody" means an antibody consisting of two "full length heavy chains" and two "full length light chains". Wherein "full-length heavy chain" refers to a polypeptide chain which is composed of a heavy chain variable region (VH), a heavy chain constant region CH1 domain, a hinge region (HR), a heavy chain constant region CH2 domain and a heavy chain constant region CH3 domain, in the N-terminal to C-terminal direction. And when the full length antibody is of the IgE isotype, it optionally further comprises a heavy chain constant region CH4 domain. Preferably, the "full length heavy chain" is a polypeptide chain consisting of VH, CH1, HR, CH2 and CH3 in the N-terminal to C-terminal direction. A "full length light chain" is a polypeptide chain consisting of a light chain variable region (VL) and a light chain constant region (CL) in the N-terminal to C-terminal direction. Two pairs of full length antibody chains are joined by a disulfide bond between CL and CH1 and a disulfide bond between the HRs of the two full length heavy chains. The full length antibodies of the present disclosure may be from a single species, such as a human; or may be chimeric or humanized antibodies. The full-length antibody of the present disclosure comprises two antigen-binding sites formed by a pair of VH and VL, respectively, which specifically recognize/bind the same antigen.

As used herein, the term "Fd fragment" means an antibody fragment consisting of a VH domain and a CH1 domain; the term "dAb fragment" means an antibody fragment consisting of a VH domain (Ward et al, Nature 341:544 546 (1989)); the term "Fab fragment" means an antibody fragment consisting of VL, VH, CL and CH1 domains; the term "F(ab')$_2$ fragment" means an antibody fragment comprising two Fab fragments linked by a disulfide bridge in the hinge regions; the term "Fab' fragment" means a fragment obtained by reducing the disulfide bond of two heavy chain fragments in a F(ab')2 fragment, consisting of a complete light and the Fd fragment of a heavy chain (consisting of VH and CH1 domains).

As used herein, the term "Fv fragment" means an antibody fragment consisting of the VL and VH domains of a single arm of an antibody. An Fv fragment is generally considered to be the smallest antibody fragment that forms a complete antigen binding site. It is believed that the six CDRs confer antigen binding specificity to the antibody. However, even a variable region (e.g., an Fd fragment that contains only three CDRs specific for an antigen) recognizes and binds to the antigen, although its affinity may be lower than the intact binding site.

As used herein, the term "Fc fragment" refers an antibody fragment that is formed by linking the second, third constant region of a first heavy chain of an antibody and the second, third constant region of a second heavy chain via disulfide bonding The Fc fragment of an antibody has many different functions but does not participate in antigen binding.

As used herein, the term "scFv" refers to a single polypeptide chain comprising VL and VH domains, wherein the VL and VH are linked by a linker (see, e.g., Bird et al, Science 242: 423-426 (1988); Huston et al, Proc. Natl. Acad. Sci. USA 85:5879-5883 (1988); and Pluckthun, The Pharmacology of Monoclonal Antibodies, Vol. 113, edited by Roseburg and Moore, Springer-Verlag, New York, pp. 269-315 (1994)). Such scFv molecules can have the general structure: $NH_2$-VL-linker-VH—COOH or $NH_2$-VH-linker-VL-COOH. Suitable linkers in prior art consist of a repeating amino acid sequence of GGGGS or variants thereof. For example, a linker having the amino acid sequence (GGGGS) 4 can be used, and variants thereof can also be used (Holliger et al. (1993), Proc. Natl. Acad. Sci. USA 90: 6444-6448). Other linkers useful in the present disclosure are described by Alfthan et al. (1995), Protein Eng. 8: 725-731, Choi et al. (2001), Eur. J. Immunol. 31: 94-106, Hu et al. (1996), Cancer Res. 56: 3055-3061, Kipriyanov et al. (1999), J. Mol. Biol. 293: 41-56 and Roovers et al. (2001), Cancer Immunol. In some cases, a disulfide bond may also be present between the VH and VL of the scFv. As used herein, the term "di-scFv" refers to an antibody fragment formed by the joining of two scFvs.

As used herein, the term "diabody" means that its VH and VL domains are expressed on a single polypeptide chain, but using a linker that is too short to allow pairing between two domains of the same chain, thereby forcing the domain to pair with the complementary domain of another strand and creating two antigen binding sites (see, for example, Holiger P. et al, Proc. Natl. Acad. Sci. USA 90:6444-6448 (1993), and Poljak R J et al., Structure 2: 1121-1123 (1994)).

Each of the above antibody fragments retains the ability to specifically bind to the same antigen to which the full length antibody binds, and/or competes with the full length antibody for specific binding to the antigen.

An antigen-binding fragment of an antibody (e.g., an antibody fragment as described above) can be obtained from a given antibody (e.g., an antibody provided herein) using conventional techniques known to those skilled in the art (e.g., recombinant DNA techniques or enzymatic or chemical cleavage methods), and can be screened for specificity using the same manner by which intact antibodies are screened.

In the present disclosure, unless specified definitely, when referring to the term "antibody", it includes not only intact antibodies, but also antigen-binding fragments of antibodies.

As used herein, the terms "monoclonal antibody", "mAb" have the same meaning and are used interchangeably, which refers to one antibody or a fragment thereof of a population of highly homologous antibody molecules, that is, a population of identical antibody molecules, except for natural mutations that may occur spontaneously. Monoclonal antibodies are highly specific for a single epitope on the antigen. Polyclonal antibodies are relative to monoclonal antibodies, which typically comprise at least two or more different antibodies which typically recognize different epitopes on the antigen. Furthermore, the modifier "monoclonal" merely indicates the character of the antibody as being obtained from a highly homogeneous population of antibodies, and is not to be construed as requiring production of the antibody by any particular method.

The monoclonal antibodies of the present disclosure can be prepared by a variety of techniques, such as hybridoma technology (see, e.g., Kohler et al. Nature, 256:495, 1975), recombinant DNA techniques (see, e.g., U.S. Pat. No. 4,816, 567), or phage antibody library technology (see, for example, Clackson et al. Nature 352:624-628, 1991, or Marks et al. J. Mol. Biol. 222:581-597, 1991).

For example, monoclonal antibodies can be prepared as follows. The mice or other suitable host animals are first immunized with immunogen (with addition of an adjuvant if necessary). The method of injection of immunogen or adjuvant is usually multi-point subcutaneous injection or intraperitoneal injection. Immunogen can be pre-coupled to certain known proteins, such as serum albumin or soybean trypsin inhibitors, to enhance the immunogenicity of the antigen in the host. The adjuvant may be Freund's adjuvant or MPL-TDM or the like. After the animal is immunized, the body will produce lymphocytes that secrete antibodies that specifically bind to the immunogen. In addition, lymphocytes can also be obtained by in vitro immunization. The lymphocytes of interest are collected and fused with myeloma cells using a suitable fusing agent, such as PEG, to obtain hybridoma cells (Goding, Monoclonal Antibodies: Principles and Practice, pp. 59-103, Academic Press, 1996). The hybridoma cells prepared above may be inoculated into a suitable culture medium which preferably contains one or more substances capable of inhibiting the growth of unfused, parental myeloma cells. For example, for parental myeloma cells lacking hypoxanthine guanine phosphotransferase (HGPRT or HPRT), the addition of hypoxanthine, aminopterin, and thymine (HAT medium) to the culture medium will inhibit growth of HGPRT-defective cells. Preferred myeloma cells should have a high fusion rate, stable antibody secretion capacity, and sensitivity to HAT culture medium. Among them, murine myeloma is preferred for myeloma cells, such as MOP-21 or MC-11 mouse tumor-derived strains (THE Salk Institute Cell Distribution Center, San Diego, Calif. USA), and SP-2/0 or X63-Ag8-653 cell line (American Type Culture Collection, Rockville, Md. USA). In addition, studies have also reported the use of human myeloma and human-murine heterologous myeloma cell lines to prepare human monoclonal antibodies (Kozbor, J. Immunol., 133: 3001 (1984); Brodeur et al., Monoclonal Antibody Production Techniques and Applications, pp 51-63, Marcel Dekker, Inc., New York, 1987). The culture medium for growing hybridoma cells is used to detect the production of monoclonal antibodies against specific antigens. Methods for determining the binding specificity of monoclonal antibodies produced by hybridoma cells include, for example, immunoprecipitation or in vitro binding assays such as radioimmunoassay (RIA), enzyme-linked immunosorbent assay (ELISA). For example, the affinity of the monoclonal antibody can be determined using the Scatchard assay described by Munson et al., Anal. Biochem. 107: 220 (1980). After determining the specificity, affinity, and reactivity of the antibody produced by the hybridoma, the cell strain of interest can be subcloned by the standard limiting dilution method described in Goding, Monoclonal Antibodies: Principles and Practice, pp. 59-103, Academic Press, 1996. A suitable culture medium may be DMEM or RPMI-1640 or the like. In addition, hybridoma cells can also be grown in animals in the form of ascites tumors. Utilizing traditional immunoglobulin purification methods, such as protein A agarose gel, hydroxyapatite chromatography, gel electrophoresis, dialysis or affinity chromatography, the monoclonal antibodies secreted by the subcloned cells can be isolated from the cell culture medium, ascites or serum.

Monoclonal antibodies can also be obtained by genetic engineering recombinant techniques. A DNA molecule encoding the heavy chain and light chain genes of a monoclonal antibody can be isolated from a hybridoma cell by PCR amplification using a nucleic acid primer that specifically binds to the monoclonal antibody heavy chain and light chain genes. The obtained DNA molecule is inserted into an expression vector, and then transfected into a host cell (such as E. coli cells, COS cells, CHO cells, or other myeloma cells that do not produce immunoglobulin), and cultured under appropriate conditions, thereby obtaining the desired recombinant antibody.

The antibody can be purified by well-known techniques, for example, affinity chromatography using Protein A or Protein G. Subsequently or alternatively, the specific antigen (the target molecule recognized by the antibody) or its antigenic epitope can be immobilized on a column and the immunospecific antibody can be purified by immunoaffinity chromatography. Purification of immunoglobulins can be found, for example, in D. Wilkinson (The Scientist, published by The Scientist, Inc., Philadelphia Pa., Vol. 14, No. 8 (Apr. 17, 2000), pp. 25-28).

As used herein, the term "Chimeric antibody" refers to an antibody in which a portion of the light or/and heavy chain thereof is derived from one antibody (which may be derived from a specific species or belong to a certain specific antibody class or subclass), and another portion of the light chain or/and heavy chain is derived from another antibody (which may be derived from the same or different species or belong to the same or different antibody class or subclass), nonetheless, it still retains binding activity to the antigen of interest (U.S. Pat. No. 4,816,567 to Cabilly et al.; Morrison et al., Proc. Natl. Acad. Sci. USA, 81:6851 6855 (1984)). For example, the term "chimeric antibody" can include an antibody (e.g., a human-murine chimeric antibody) wherein the heavy and light chain variable regions of the antibody are derived from a first antibody (e.g., a murine antibody), while the heavy chain and light chain variable regions of the antibody are derived from a second antibody (e.g., a human antibody).

As used herein, the term "humanized antibody" refers to a genetically engineered non-human antibody whose amino acid sequence has been modified to increase homology to the sequence of a human antibody. Generally, all or part of the CDR regions of a humanized antibody are derived from a non-human antibody (donor antibody), and all or part of the non-CDR regions (e.g., variable region FRs and/or constant region) are derived from a human immunoglobulin (receptor antibody). Humanized antibodies typically retain the desired properties of the donor antibody, including, but not limited to, antigen specificity, affinity, reactivity, ability to increase immune cell activity, ability to enhance an immune response, and the like. A donor antibody can be an antibody from mouse, rat, rabbit, or non-human primate (e.g., cynomolgus) having desirable properties (e.g., antigen specificity, affinity, reactivity, ability to increase immune cell activity and/or enhance immune response).

A humanized antibody is capable of retaining both the expected properties of a non-human donor antibody (e.g., a murine antibody) and is effective in reducing the immunogenicity of a non-human donor antibody (e.g., a murine antibody) in a human subject. Therefore, it is particularly advantageous. However, due to the problem of matching between the CDRs of the donor antibody and the FR of the acceptor antibody, the expected properties of the humanized antibody (e.g., antigen specificity, affinity, reactivity, ability to increase immune cell activity, and/or the ability to enhance an immune response) is generally lower than the non-human donor antibody (e.g., a murine antibody).

Therefore, although researchers in the field have conducted in-depth research on the humanization of antibodies and made some progress (see, for example, Jones et al., Nature, 321:522 525 (1986); Reichmann et al., Nature, 332:323 329 (1988); Presta, Curr. Op. Struct. Biol., 2:593 596 (1992); and Clark, Immunol. Today 21: 397 402 (2000)), the current art does not provide detailed information on how to sufficiently humanize a donor antibody such that the humanized antibody produced can have a humanization degree as high as possible and retain the expected properties of the donor antibody as much as possible. The skilled person needs to research, explore and modify specific donor antibodies, and spend a large amount of creative work to obtain a humanized antibody which has a high degree of humanization (for example, a humanization degree of at least 75%, at least 80%, at least 85%, at least 90%, at least 91%, at least 92%, at least 93%, at least 94%, at least 95%, at least 96%, at least 97%, at least 98%, or at least 99%), while retaining the expected properties of the specific donor antibody.

In the present disclosure, in order for the humanized antibody to retain properties of the donor antibody (including, for example, antigen specificity, affinity, reactivity, ability to enhance immune cell activity and/or enhance immune response) as much as possible, the framework region (FR) of the humanized antibody of the present disclosure may comprise both an amino acid residue of a human receptor antibody and a corresponding amino acid residue of a non-human donor antibody.

In the present disclosure, the expected properties of the antibodies of the present disclosure include: (1) the ability to specifically recognize/bind to LAG-3 (particularly human LAG-3); (2) the ability to inhibit and/or block LAG-3 binding to MHC II; (3) the ability to inhibit and/or block intracellular signaling mediated by the binding of LAG-3 to MHC II; (4) inhibit and/or block LAG-3 binding to Fibrinogen-like protein 1 (FGL1); (5) inhibit and/or block intracellular signaling mediated by LAG-3 binding to FGL1; (6) the ability to enhance immune cell activities; (7) the ability to enhance immune response; (8) reduce or eliminate the ability to induce antibody-dependent cell-mediated cytotoxicity (ADCC) and/or complement-dependent cytotoxicity (CDC); (9) the ability to induce antibody-dependent cell-mediated cytotoxicity (ADCC) and/or complement dependent cytotoxicity (CDC). The humanized antibody of the present disclosure retains one or more of the above-mentioned expected properties of the parent antibody (murine antibody or murine-human chimeric antibody).

The chimeric or humanized antibody of the present disclosure can be produced based on the sequence of the murine monoclonal antibody prepared above. DNA encoding heavy and light chains can be obtained from a murine hybridoma of interest and engineered using standard molecular biology techniques to include non-murine (e.g., human) immunoglobulin sequences.

To prepare a chimeric antibody, the murine immunoglobulin variable region can be ligated to a human immunoglobulin constant region using methods known in the art (see, e.g., U.S. Pat. No. 4,816,567, Cabilly et al.). For example, a DNA encoding VH is operably linked to another DNA molecule encoding a heavy chain constant region to obtain a full length heavy chain gene. The sequence of the human heavy chain constant region gene is known in the art (see, for example, Kabat, E A et al. (1991) Sequences of Proteins of Immunological Interest, Fifth Edition, US Department of Health and Human Services, NIH Publication No. 91-3242), DNA fragments containing these regions can be obtained by standard PCR amplification. The heavy chain constant region can be an IgG1, IgG2, IgG3, IgG4, IgA, IgE, IgM or IgD constant region, but is generally preferred to be an IgG1 or IgG4 constant region. For example, a DNA encoding VL is operably linked to another DNA molecule encoding a light chain constant region CL to obtain a full length light chain gene (as well as a Fab light chain gene). The sequence of the human light chain constant region gene is known in the art (see, for example, Kabat, E A et al. (1991) Sequences of Proteins of Immunological Interest, Fifth Edition, US Department of Health and Human Services, NIH Publication No. 91-3242), DNA fragments containing these regions can be obtained by standard PCR amplification. The light chain constant region can be a kappa or lambda constant region, but is generally preferred to be a kappa constant region.

For the preparation of a humanized antibody, the murine CDR regions can be inserted into a human framework sequence using methods known in the art (see U.S. Pat. No. 5,225,539 to Winter; U.S. Pat. Nos. 5,530,101; 5,585,089; 5,693,762 and 6,180,370 to Queen et al.; and Lo, Benny, K C, editor, in Antibody Engineering: Methods and Protocols, volume 248, Humana Press, New Jersey, 2004). Alternatively, immunization of transgenic animals can be utilized to produce a complete human antibody repertoire but not producing endogenous immunoglobulins. For example, it has been reported that homozygous deletion of the antibody heavy chain joining region (JH) gene in chimeric and germline mutant mice can completely inhibit endogenous antibody production, and then transferring the human germline immunoglobulin gene array to the germline mutant mouse will result in the mouse producing human antibodies upon antigen stimulation (see, for example, Jakobovits et al, 1993, Proc. Natl. Acad. Sci. USA 90:2551; Jakobovits et al, 1993, Nature 362:255-258; Bruggermann et al, 1993, Year in Immunology 7:33; and Duchosal et al, 1992, Nature 355:258). Non-limiting examples of such transgenic animals include HuMAb mice (Medarex, Inc.), which contains human immunoglobulin gene miniloci that encode unrearranged human heavy chain (μ and γ) and kappa light chain immunoglobulin sequences, together with targeted mutation that inactivates the endogenous μ and kappa chain loci (see, e.g., Lonberg et al. (1994) Nature 368 (6474): 856-859); or "KM Mouse™" carrying a human heavy chain transgene and human light chain chromosome (see patent application WO 02/43478). Other methods of humanizing antibodies also include phage display technology (Hoogenboom et al, 1991, J. Mol. Biol. 227: 381; Marks et al, J. Mol. Biol. 1991, 222: 581-597; Vaughan et al, 1996, Nature Biotech 14: 309).

As used herein, the term "degree of humanization" is an indicator used to assess the amount of non-human amino acid residues in a humanized antibody. The degree of humanization of the humanized antibody can be assessed, for example, by predicting the homology of the variable region sequence to the human V domain with the IMGT website DomainGapAlign.

As used herein, the term "specifically binds" or "specific binding" refers to a non-random binding reaction between two molecules, such as a reaction between an antibody and the antigen to which it is directed. The strength or affinity of a specific binding interaction can be expressed as the equilibrium dissociation constant ($K_D$) of the interaction. In the present disclosure, the term "$K_D$" refers to the dissociation equilibrium constant of a particular antibody-antigen interaction, which is used to describe the binding affinity between an antibody and an antigen. The lower equilibrium dissociation constant, the tighter antibody-antigen binding and the higher affinity between the antibody and the antigen. In certain embodiments, an antibody that specifically binds to an antigen (or an antibody that is specific for an antigen) means that the antibody binds to the antigen with an affinity ($K_D$) of less than about $10^{-9}$ M, such as less than about $10^{-9}$ M, $10^{-10}$M, $10^{-11}$M or $10^{-12}$ M or less. In certain embodiments, an antibody or an antigen-binding fragment thereof of the present disclosure, is considered to specifically bind to LAG-3 when $K_D$ is less or equal to $1 \times 10^{-9}$ M (preferably, less or equal to $5 \times 10^{-10}$ M).

The specific binding properties between the two molecules can be determined using methods well known in the art. One method involves measuring the rate of formation and dissociation of the antigen binding site/antigen complex. Both the "binding rate constant" (ka or kon) and the "dissociation rate constant" (kdis or koff) can be calculated from the concentration and the actual rate of association and dissociation (see Malmqvist M, Nature, 1993, 361: 186-187). The ratio of kdis/kon is equal to the dissociation constant $K_D$ (see Davies et al, Annual Rev Biochem, 1990; 59: 439-473). The $K_D$, kon and kdis values can be measured in any effective way. In certain embodiments, the dissociation constant can be measured using bioluminescence interferometry (e.g., the ForteBio Octet method described in Example 3). In addition, the dissociation constant can be measured by surface plasmon resonance techniques (for example, Biacore) or Kinexa.

As used herein, the term "vector" refers to a nucleic acid vehicle into which a polynucleotide can be inserted. A vector is referred to as an expression vector when the vector enables expression of the protein encoded by the inserted polynucleotide. The vector can be introduced into the host cell by transformation, transduction or transfection, and the genetic material element carried thereby can be expressed in the host cell. Vectors are well known to those skilled in the art and include, but are not limited to, plasmids; phagemids; cosmids; artificial chromosomes, such as yeast artificial chromosomes (YAC), bacterial artificial chromosomes (BAC), or P1 derived artificial chromosomes (PAC). phage such as lambda phage or M13 phage and animal virus. Animal viruses that can be used as vectors include, but are not limited to, retroviruses (including lentiviruses), adenoviruses, adeno-associated viruses, herpes viruses (such as herpes simplex virus), poxviruses, baculoviruses, papillomaviruses, papovavirus (such as SV40). A vector may contain a variety of elements that control expression, including, but not limited to, promoter sequences, transcription initiation sequences, enhancer sequences, selection elements, and reporter genes. In addition, the vector may also contain an origin of replication.

As used herein, the term "host cell" refers to a cell that can be used to introduce a vector, including, but not limited to, a prokaryotic cell such as *Escherichia coli* or *Bacillus subtilis*, a fungal cell such as a yeast cell or an *Aspergillus*. For example, S2 *Drosophila* cells or insect cells such as Sf9, or animal cells such as fibroblasts, CHO cells, COS cells, NSO cells, HeLa cells, BHK cells, HEK 293 cells or human cells.

As used herein, the term "identity" is used to refer to the matching degree of sequences between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The "percent identity" between two sequences is a function of the number of identical sites shared by the two sequences over the total number of sites for comparison× 100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" means an amino acid substitution that does not adversely affect or alter the expected properties of a protein/polypeptide comprising an amino acid sequence. For example, conservative substitutions can be introduced by standard techniques known in the art, such as site-directed mutagenesis and PCR-mediated mutagenesis. Conservative amino acid substitutions include substitutions wherein an amino acid residue is substituted with another amino acid residue having a similar side chain, for example, a residue physically or functionally similar (e.g., having similar size, shape, charge, chemical properties, including ability of forming a covalent bond or a hydrogen bond, etc.) to the corresponding amino acid residue. A family of amino acid residues having similar side chains has been defined in the art. These families include amino acids having basic side chains (e.g., lysine, arginine, and histidine), acidic side chains (e.g., aspartic acid, glutamic acid), uncharged polar side chains (e.g., glycine, asparagine, glutamine, serine, threonine, tyrosine, cysteine, tryptophan), non-polar side chains (e.g. alanine, valine, leucine, isoleucine, valine, phenylalanine, methionine), beta branch side chains (e.g., threonine, valine, isoleucine) and aromatic side chains (e.g., tyrosine, phenylalanine, tryptophan, histidine). Therefore, it is preferred to replace the corresponding amino acid residue with another amino acid residue from the same side chain family. Methods for identifying conservative substitutions of amino acids are well known in the art (see, for example, Brummell et al, Biochem. 32: 1180-1187 (1993); Kobayashi et al., Protein Eng. 12(10): 879-884 (1999); and Burks et al. Proc. Natl Acad. Set USA 94: 412-417 (1997), which is incorporated herein by reference).

The twenty conventional amino acids involved herein are expressed in routine manners. See, for example, Immunology-A Synthesis (2nd Edition, E. S. Golub and D. R. Gren, Eds., Sinauer Associates, Sunderland, Mass. (1991)), which is incorporated herein by reference. In the present disclosure, the terms "polypeptide" and "protein" have the same meaning and are used interchangeably. Also in the present disclosure, amino acids are generally represented by single letter and three letter abbreviations as known in the art. For example, alanine can be represented by A or Ala.

The term "pharmaceutically acceptable carrier and/or excipient" as used herein refers to a carrier and/or excipient that is pharmacologically and/or physiologically compatible with the subject and the active ingredient, which is well known in the art (see, for example, Remington's Pharmaceutical Sciences. Edited by Gennaro A R, 19th ed. Pennsylvania: Mack Publishing Company, 1995) and includes, but is not limited to, pH adjusting agents, surfactants, adjuvants, ionic strength enhancers, diluents, agents that maintain osmotic pressure, agents that delay absorption, preservatives. For example, pH adjusting agents include, but are not limited to, phosphate buffers. Surfactants include, but are not limited to, cationic, anionic or nonionic surfactants such as Tween-80. Ionic strength enhancers include, but are not limited to, sodium chloride. Preservatives include, but are not limited to, various antibacterial and antifungal agents, such as parabens, chlorobutanol, phenol, sorbic acid, and the like. Agents that maintain osmotic pressure include, but are not limited to, sugars, NaCl, and the like. Agents that delay absorption include, but are not limited to, monostearate and gelatin. Diluents include, but are not limited to, water, aqueous buffers (such as buffered saline), alcohols and polyols (such as glycerin), and the like. Preservatives include, but are not limited to, various antibacterial and antifungal agents, such as thimerosal, 2-phenoxyethanol, parabens, chlorobutanol, phenol, sorbic acid, and the like. Stabilizers have the meaning commonly understood by those skilled in the art which can stabilize the desired activity of the active ingredient in the drug, including but not limited to sodium glutamate, gelatin, SPGA, sugars (e.g., sorbitol, mannitol, starch, sucrose, lactose, dextran, or glucose), amino acids (such as glutamic acid, glycine), proteins (such as dried whey, albumin or casein) or degradation products thereof (such as lactalbumin hydrolysate).

As used herein, the term "prevention" refers to a method performed to prevent or delay the onset of a disease or condition or symptom (e.g., a tumor, infection, or autoimmune disease) in a subject. As used herein, the term "treatment" refers to a method performed to obtain a beneficial or desired clinical result. For the purposes of the present disclosure, the beneficial or desired clinical results include, but are not limited to, alleviating symptoms, narrowing the extent of the disease, stabilizing (i.e., not worsening) the state of the disease, delaying or slowing the progression of the disease, improving or alleviating the status of disease, and alleviating a symptom (either in part or in whole), either detectable or undetectable. Further, "treating" can also mean prolonging the survival period as compared to the desired survival period (if not receiving treatment).

As used herein, the term "subject" refers to a mammal, such as a primate mammal, such as a human. In certain embodiments, the subject (e.g., a human) has a tumor, an infection, or an autoimmune disease, or has a risk of having the above-described disease.

As used herein, the term "effective amount" refers to an amount sufficient to achieve, or at least partially achieve, a desired effect. For example, an effective amount to prevent a disease (e.g., a tumor, an infection, or an autoimmune disease) refers to an amount sufficient to prevent, stop or delay the onset of a disease (e.g., a tumor, an infection, or an autoimmune disease); an effective amount to treat a disease refers to an amount sufficient to cure or at least partially arrest the disease and its complications in a patient suffering from the disease. Determination of such an effective amount is well within the capabilities of those skilled in the art. For example, the amount effective for therapeutic use will depend on the severity of the condition to be treated, the overall condition of the patient's own immune system, the general condition of the patient such as age, weight and sex, the administration route of the drug, and other treatments administrated simultaneously, etc.

As used herein, the term "immune cells" includes cells that have a hematopoietic origin and play a role in an immune response, such as lymphocytes, such as B cells and T cells; natural killer cells; myeloid cells, such as monocytes, macrophages, eosinophils, mast cells, basophils, and granulocytes.

As used herein, the term "immune response" refers to effect of immune cells (e.g., lymphocytes, antigen presenting cells, phagocytic cells, or granulocytes) and the soluble macromolecules (including antibodies, cytokines, and complements) produced by immune cells or liver, the effect results in selective damage or destruction of invasive pathogens, cells or tissues infected with pathogens, cancer cells, or normal human cells or tissues in the context of autoimmune or pathological inflammation, or removal of them from a subject. In the present disclosure, the term "antigen-specific T cell response" refers to an immune response produced by a T cell which is generated when the T cell-specific antigen stimulates T cells. Non-limiting examples of responses produced by T cells upon antigen-specific stimulation include proliferation of T cells and production of cytokines (e.g., IL-2).

As used herein, the term "effector function" refers to those biological activities attributable to the Fc region of an antibody (Fc region of a natural sequence or an amino acid sequence variant), which varies as the isotype of an antibody. Examples of antibody effector functions include, but are not limited to, Fc receptor binding affinity, antibody-dependent cell-mediated cytotoxicity (ADCC), complement dependent cytotoxicity (CDC), antibody-dependent cellular phagocytosis (ADCP), downregulation of cell surface receptors (e.g., B cell receptors), B cell activation, cytokine secretion, half-life/clearance of antibodies and antigen-antibody complexes, and the like. Methods for altering the effector function of an antibody are known in the art, for example by introducing a mutation in the Fc region.

As used herein, the term "antibody-dependent cell-mediated cytotoxicity (ADCC)" refers to a form of cytotoxicity, in which cytotoxic effector cells specifically bind to the target cells to which the antigen is attached, through the binding of Ig to an Fc receptor (FcR) presented on cytotoxic cells (e.g., natural killer (NK) cells, neutrophils or macrophages), and then kills the target cells by secreting cytotoxins. Methods for detecting ADCC activity of an antibody are known in the art and can be evaluated, for example, by measuring the binding activity between an antibody to be tested and an Fc receptor (e.g., CD16a).

As used herein, the term "complement dependent cytotoxicity (CDC)" refers to a form of cytotoxicity in which the complement cascade is activated by the binding of complement component Cq to Fc of an antibody. Methods for detecting the CDC activity of an antibody are known in the art and can be evaluated, for example, by measuring the binding activity between an antibody to be tested and an Fc receptor (e.g., C1q).

The terms "cancer" and "tumor" are used interchangeably and refer to a broad class of diseases characterized by uncontrolled growth of abnormal cells in the body. Uncontrolled cell division can result in the formation of malignant tumors or cells that invade adjacent tissues and may be transferred to the distal part of the body through the lymphatic system or blood flow. Cancer includes benign and malignant cancers as well as dormant tumors or micrometastases. Cancer also includes hematological malignancies.

Examples of tumors include, but are not limited to, solid tumors, hematological tumors (e.g., leukemias, lymphomas, myeloma, e.g., multiple myeloma), and metastatic, refractory or recurrent lesions of cancer; for example, including not limited to esophageal cancer, gastrointestinal cancer, pancreatic cancer, thyroid cancer, colorectal cancer, kidney cancer, lung cancer (such as non-small cell lung cancer), liver cancer, stomach cancer, head and neck cancer, bladder cancer, breast cancer, uterine cancer, cervical cancer, ovarian cancer, prostate cancer, testicular cancer, germ cell cancer, bone cancer, skin cancer, thymus cancer, cholangiocarcinoma, gallbladder cancer, melanoma, mesothelioma, lymphoma, myeloma (e.g. multiple myeloma), sarcoma, glioblastoma, glioblastoma multiforme, leukemia.

The term "hematological malignancy" includes lymphoma, leukemia, myeloma or lymphoid malignancies, as well as spleen cancer and lymph node tumors. Exemplary lymphomas include B cell lymphoma and T cell lymphoma. B cell lymphomas include, for example, Hodgkin's lymphoma. T cell lymphomas include, for example, cutaneous T-cell lymphoma. Hematological malignancies also include leukemia, such as secondary leukemia or acute lymphocytic leukemia. Hematological malignancies also include myeloma (e.g., multiple myeloma) and other hematological and/or B cell- or T cell-related cancers.

The term "pharmaceutically acceptable" means that when a molecular itself, molecular fragment or composition is suitably administered to an animal or a human, it does not produce an adverse, allergic or other untoward reaction. Specific examples of some substances which can be used as a pharmaceutically acceptable carrier or a component thereof include sugars such as lactose, starch, cellulose and derivatives thereof, vegetable oils, gelatin, polyols such as propylene glycol, alginic acid and the like.

Advantageous Effects of the Present Disclosure

Compared with the prior art, the technical solutions of the present disclosure have the following beneficial effects:

(1) The antibody of the present disclosure can not only specifically recognize/bind to LAG-3, block the binding of LAG-3 to MHC II or FGL1, but also enhance immune cell activities and stimulate immune responses in vitro/in vivo. Thus, the antibodies of the present disclosure have the potential to prevent and/or treat tumors, infections or autoimmune diseases.

(2) The antibodies (especially the humanized antibody) of the present disclosure not only retain the function and properties of the parent mouse antibody, thus having the potential for preventing and treating tumors, infections or autoimmune diseases; but have a very high degree of humanization, and thus can be safely administered to a human subject without eliciting an immunogenic response. Therefore, the antibodies (especially humanized antibodies) of the present disclosure have great clinical value.

The embodiments of the present disclosure will be described in detail below with reference to the accompanying drawings and embodiments. Various objects and advantages of the present disclosure will become apparent to those skilled in the art.

DESCRIPTION OF THE DEPOSIT OF BIOLOGICAL MATERIALS

Figure 1:
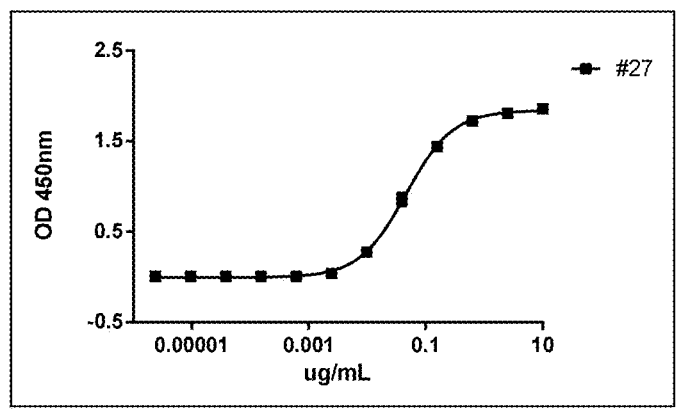
FIG. 1 shows the ELISA results of binding activity of murine monoclonal antibody #27 to human LAG-3 of Example 2.

The present disclosure relates to the following biological materials that have been deposited at the China Center for Type Culture Collection (CCTCC, Wuhan University, Wuhan, China):

Hybridoma cell line #27, which has accession number CCTCC NO. C2017183, and was deposited on Oct. 25, 2017.

EXAMPLES

The following examples are put forth so as to illustrate the present disclosure, and are not intended to limit the scope of the present disclosure.

Unless otherwise indicated, the molecular biological experimental methods and immunodetection methods used in the present disclosure basically referred to J Sambrook et al., Molecular Cloning: a laboratory manual, second edition, Cold Spring Harbor Laboratory Press, 1989, and F/M Ausubel et al., Short Protocols in Molecular Biology, 3rd edition, John Wiley and Sons, Inc., 1995. The use of the restriction endonuclease is in accordance with the conditions recommended by the product manufacturer. Those skilled in the art would know that the embodiments describe the present disclosure by way of examples, and are not intended to limit the scope of the present disclosure as claimed.

Example 1: Production of Anti-Human LAG-3 Murine Monoclonal Antibody

After emulsification of human LAG-3 (Uniport entry No. P18627) (50 μg per mouse) in complete Freund's adjuvant, male Balb/C mice were immunized by multi-point immunization once every three weeks. On the 10th day after the third immunization, blood was taken through retro-orbital bleeding, and the titer of anti-human LAG-3 antibody in mouse plasma was measured by indirect ELISA to monitor the degree of immune response in mice, and methods are described in Example 2. The mice that produced the highest titer of anti-human LAG-3 antibody were boosted once 3 days before the fusion. The mice were sacrificed 3 days later, and the spleens of the mice were taken out to make a single cell suspension, then the suspension was fused with mouse myeloma cell line Sp2/0 at a ratio of 1:1 in a solution containing 50% polyethylene glycol (molecular weight: 1450) and 5% dimethyl sulfoxide (DMSO). The number of spleen cells was adjusted to about $5 \times 10^5$/mL by using Iscove medium (containing 10% fetal bovine serum, 100 units/mL penicillin, 100 μg/mL streptomycin, 0.1 mM hypoxanthine, 0.4 μM aminopterin and 16 μM thymidine), and was added to the wells of a 96-well culture plate at 0.3 mL per well, followed by incubation at 37° C., 5% $CO_2$. After 10 days of culture, the culture supernatant was collected and serially diluted with a ratio of 1:10, and was subjected to indirect ELISA to select a cell strain having binding activity to human LAG-3. Subsequently, the identified 8 positive cell strains were subcloned separately. The LAG-3/MHC II kit (CISBIO, product number ADK000CLAPEF) was used to detect the blocking effect of the 8 positive cell strains on the binding of LAG-3/MHC II, thereby assessing the blocking biological activity of the antibody. Monoclonal cell strain #27 was finally obtained, of which the blocking effect was significantly better than that of other strains. Then, murine monoclonal antibody #27 was isolated and purified from the culture supernatant of hybridoma cell strain #27.

Example 2: Evaluation of LAG-3 Binding Activity of the Anti-Human LAG-3 Murine Antibody The titer of the murine monoclonal antibody #27 isolated and purified from the culture supernatant of the hybridoma cell strain #27 was measured by ELISA. LAG-3 (Uniport entry No. P18627) was diluted to 0.1 μg/ml with PBS buffer, and was added to a 96-well plate at 100 μl per well, and placed at 4° C. for 16-20 h. The PBS buffer in the 96-well plate was aspirated, and the plate was washed once with PBST (pH 7.4, PBS containing 0.05% Tween 20) buffer, and then 200 μl/well of PBST containing 1% skim milk powder (blocking solution) was added, followed by incubation for 1 h at room temperature. After removing the blocking solution and washing the plate with PBST buffer for 3 times, the anti-LAG-3 murine antibody to be tested was diluted with PBST containing 1% skim milk powder to a suitable concentration, then added at 100 μl/well and incubated at room temperature for 1.5 h. After removing the reaction system, the plate was washed three times with PBST, and added with 50 μl/well of HRP-labeled goat anti-mouse IgG secondary antibody diluted with PBST containing 1% skim milk powder (diluted 1:5000) (purchased from The Jackson Laboratory), followed by incubation for 1 h at room temperature. After washing the plate 3 times with PBST, 100 μl/well of TMB was added and incubated for 10-30 min at room temperature to develop color. Color development was stopped by adding 50 μl/well of 0.2 M sulfuric acid. The absorbance (O.D.) was detected at a dual wavelength of 450/620 nm by using a microplate reader.

The fitted curve of the resulting values is shown in FIG. 1. The results show that murine monoclonal antibody #27 expressed by hybridoma clone #27 can efficiently bind to LAG-3.

Example 3: Affinity Detection of Anti-Human LAG-3 Murine Antibody

The binding affinity constant of the purified murine monoclonal antibody #27 to the antigen was determined by Bio-Layer Interferometry (BLI) using the instrument of a PALL company's ForteBio Octet RED & QK system. The concentration gradients for parallel quantitative analysis on multi-channel were set to: 3.125, 6.25, 12.5, 25, 50, and 100 nM, and human LAG-3 (His tag) was coupled with a Ni-NTA sensor. The results of the affinity assay are shown in Table 1. The results show that the murine monoclonal antibody #27 has a very high binding affinity to human LAG-3 and can reach the order of $10^{-10}$ M.

TABLE 1

| Affinity determination results of murine monoclonal antibody | | | |
|---|---|---|---|
| Antibody | $K_D$ (M) | kon (1/Ms) | kdis (1/s) |
| #27 | 3.19E−10 | 1.21E+05 | 3.86E−05 |

Example 4: Humanization and Antibody Subtype Identification of Anti-Human LAG-3 Murine Antibody Hybridoma cell culture supernatants were taken and subjected to antibody subtype identification by using the IsoStrip™ Mouse Monoclonal Subtype Identification Kit (Santa Cruz Biotechnology). The subtype of murine antibody #27 was identified as IgG4 (Kappa).

Antibody variable region amplification: The candidate hybridoma cell strain #27 was cultured to a total of $10^7$ cells, and then centrifuged at 1000 rpm for 10 min. Total RNA was extracted with Trizol kit (Invitrogen), and a reverse transcription kit SMARTer RACE was used to synthesize the first strand cDNA, which was subsequently used as a template for amplification of the antibody variable region DNA sequences corresponding to the hybridoma cells. According to the subtype identification result, the heavy chain and light chain constant region sequences of the antibody subtype were obtained, and specific nested PCR primers were designed, and the primer sequences used in the amplification reaction were complementary to the first frame region of the variable region and the constant region of the antibody. The target gene was amplified by a conventional PCR method, and the amplified products were sequenced. The heavy chain variable region and light chain variable region sequences of antibody #27 secreted by hybridoma cell line #27 are identified as SEQ ID NO: 1 and SEQ ID NO: 2, respectively. The amino acid sequences of the heavy chain CDRs (CDR-H1, CDR-H2 and CDR-H3) of the antibody are as follows:

TABLE 2-1

| Heavy chain CDRs of murine antibody #27 | | | |
|---|---|---|---|
| | Chothia | Kabat | IMGT |
| CDR-H1 | GYSITSFY (SEQ ID NO: 9) | SFYSWH (SEQ ID NO: 14) | GYSITSFYS (SEQ ID NO: 3) |
| CDR-H2 | QYSGD (SEQ ID NO: 10) | CIQYSGDTDSNPS LKS (SEQ ID NO: 15) | IQYSGDT (SEQ ID NO: 4) |
| CDR-H3 | SPYDSDPYYVMDY (SEQ ID NO: 11) | SPYDSDPYYVMDY (SEQ ID NO: 11) | ARSPYDSDP YYVMDY (SEQ ID NO: 5) |

The amino acid sequences of the light chain CDRs (CDR-L1, CDR-L2 and CDR-L3) are as follows:

TABLE 2-2

| Light chain CDRs of murine antibody #27 | | | |
|---|---|---|---|
| | Chothia | Kabat | IMGT |
| CDR-L1 | KSSQSLLYS GNQKNYLA (SEQ ID NO: 12) | KSSQSLLYS GNQKNYLA (SEQ ID NO: 12) | QSLLYSGNQKNY (SEQ ID NO: 6) |
| CDR-L2 | WASTRDS (SEQ ID NO: 13) | WASTRDS (SEQ ID NO: 13) | WAS (SEQ ID NO: 7) |
| CDR-L3 | QQYYAYPYT (SEQ ID NO: 8) | QQYYAYPYT (SEQ ID NO: 8) | QQYYAYPYT (SEQ ID NO: 8) |

The above CDR region sequences are defined by the Chothia, Kabat and IMGT methods, respectively, and any other method for determining CDR region sequences known in the art can be used to identify the amino acid residues of the CDR regions in the variable region.

The murine antibody was humanized by CDR grafting antibody humanization method. Briefly, the humanization process involves the following steps: aligning the amino acid sequences of murine monoclonal antibody #27 with the amino acid sequences of human germline antibody to find sequences with high homology; analyzing the HLA-DR affinity, and selecting the human germline framework sequences with low affinity; grafting the six CDRs of the murine antibody into the selected heavy and light chain framework sequences, respectively.

Specifically, based on extensive analysis and experiments, the inventors unexpectedly discovered that the human germline gene sequence IGHV4-31*02 (see IMGT accession number M99683) and IGKV4-1*01 (see IMGT accession number Z00023) is particularly advantageous as the human antibody template for receiving CDRs of murine antibody #27. The heavy and light chain CDR regions of the murine antibody #27 were then grafted onto the corresponding FR framework of the humanized template described above.

Further, using computer simulation technology, molecular docking analysis of the variable region and its surrounding framework amino acid sequences was applied to investigate the spatial stereoscopic binding mode. By calculating electrostatic force, van der Waals force, hydrophilicity and entropy, the key amino acids for interaction with LAG-3 and maintenance of the spatial structure in the amino acid sequence of the murine antibody was analyzed, and these murine amino acids were retained in the grafted antibody. That is, a series of back mutations were made to the FR region amino acid residues of the above humanized template, so that the humanized antibody could retain the antigen binding ability of the murine antibody as much as possible.

According to the above method, four humanized antibodies were constructed based on the CDRs of murine antibody #27, which were named AB12T3, AB12T5, AB12T6 and AB12T7. The heavy chain constant region of each antibody was human IgG4 heavy chains (SEQ ID NO: 28). A human-mouse chimeric antibody (AB12T2) was also constructed by fusing the heavy chain variable region sequence of the murine antibody onto the human IgG4 (S228P) heavy chain constant region (SEQ ID NO: 29), and fusing the light chain variable region sequence of the murine antibody onto the human Kappa light chain constant region (SEQ ID NO: 33).

Further, the variable region sequence of the antibody secreted by the hybridoma cells obtained above was humanized by a surface remodeling method. The method of surface remodeling refers to the humanization of amino acid residues on the surface of heterologous antibodies. This method only involves replacement of the regions where amino acids were significantly different from those on the surface of human antibodies, and selection of amino acids which are similar to human antibody surface residues for replacement, while maintaining antibody activity and reducing heterogeneity. Specifically, the surface remodeling humanization process involves the following steps: first, the amino acid sequences of the antibody secreted by each hybridoma cell was aligned with the amino acid sequences of the human germline antibody to find sequences with high homology; then the exposed surface amino acids were replaced with adult germline antibody amino acids by using computer simulation technique and setting the solvent accessibility to greater than 30%. Residues which affects side chain size, charge, hydrophobicity, or may form hydrogen bonds and thus affect the conformation of the antibody complementarity determining regions, were retained as much as possible.

According to the above method, humanized antibodies AB12T4, AB12T8 and AB12T9 were constructed based on the CDRs of murine antibody #27 and by using the human IGHV4-31*02 heavy chain variable region and human IGKV4-1*01 light chain variable region as template sequences. The heavy chain constant region of AB12T4 is a human IgG4 heavy chain constant region (IgG4 V1) (SEQ ID NO: 29), and the heavy chain constant region of AB12T8 is human IgG1 heavy chain constant region variant 1 (IgG1 V1; SEQ ID NO: 31) which is a human IgG1 heavy chain constant region containing Leu234Ala, Leu235Ala and Gly237Ala mutations with reduced ADCC and CDC effects; the heavy chain constant region of AB12T9 is human IgG1 heavy chain constant region variant 2 (IgG1 V2; SEQ ID NO: 32) which is a human IgG1 heavy chain constant region containing the Asn297Ala, Asp356Glu and Leu358Met mutations, eliminating the ADCC effect.

The variable region and constant region amino acid sequences of the above humanized antibodies and human-mouse chimeric antibody are shown in Table 3.

TABLE 3

Humanized antibody variable and constant region amino acid sequences

| Antibody | Heavy chain variable region (SEQ ID NO:) | Light chain variable region (SEQ ID NO:) | Heavy chain constant region (SEQ ID NO:) | Light chain constant region (SEQ ID NO:) |
| --- | --- | --- | --- | --- |
| AB12T2 | 1 | 2 | 29 | 33 |
| AB12T3 | 16 | 17 | 28 | |
| AB12T4 | 18 | 19 | 29 | |
| AB12T5 | 20 | 21 | 28 | |
| AB12T6 | 22 | 23 | 28 | |
| AB12T7 | 24 | 25 | 28 | |
| AB12T8 | 26 | 27 | 31 | |
| AB12T9 | 26 | 27 | 32 | |

Example 5: Construction of Expression Vector for Anti-Human LAG-3 Antibody, and Expression, Preparation, and Affinity Determination of the Antibody According to the heavy and light chain sequences obtained in the above example, the coding cDNA was designed to be inserted into the pCMAB2M eukaryotic expression vector to construct a humanized expression vector. The expression vector plasmid contains the cytomegalovirus early gene promoter-enhancer required for high level expression in mammalian cells. And, the vector plasmid contains a selectable marker gene to confer ampicillin resistance in the bacteria while giving G418 resistance in the mammalian cells. In addition, the vector plasmid contains a dihydrofolate reductase (DHFR) gene, and the antibody gene and the DHFR gene can be co-amplified with methotrexate (MTX) in a suitable host cell.

The constructed recombinant expression plasmid described above is transfected into a mammalian host cell line to express a humanized antibody. In order to stabilize high levels of expression, the preferred host cell line was a DHFR deficient Chinese hamster ovary (CHO) cell (see U.S. Pat. No. 4,818,679). The preferred method of transfection was electroporation, and other methods may be used, including calcium phosphate co-precipitation, lipofection, protoplast fusion and the like. In electroporation, GenePulser (Bio-Rad Laboratories) was used with an electric field of 300 V and a capacitance of 1050 µFd, and $2 \times 10^7$ cells were suspended in 0.8 ml of PBS with 20 µg of expression vector in a cuvette. Two days after transfection, 0.2 mg/ml G418 and 200 nM MTX (Sigma) were added. To achieve higher levels of expression, the transfected antibody gene was co-amplified with the DHFR gene inhibited by the MTX drug. The secretion rate of each cell line was determined by limiting dilution subcloning of transfectants and ELISA method, and cell lines expressing antibodies at high levels were selected. The conditioned medium from which the antibody was collected was used to determine its biological activity in vitro and in vivo.

Then, the affinity of the humanized antibodies and the chimeric antibodies to human LAG-3 was measured by the method described in Example 3, and the results are shown in Table 4 below. The results showed that all the 7 humanized antibodies and chimeric antibodies had an affinity of the order of $10^{-10}$ M, and maintained the excellent affinity of murine antibody #27 for LAG-3 overall. In particular, AB12T4, AB12T8, and AB12T9 have slightly increased affinity for human LAG-3 compared to murine antibodies.

TABLE 4

Affinity of humanized antibodies and chimeric antibodies

| Antibody | $K_D$ (M) | kon (1/Ms) | kdis (1/s) |
| --- | --- | --- | --- |
| #27 | 3.19E−10 | 1.21E+05 | 3.19E−05 |
| AB12T2 | 5.74E−10 | 1.00E+05 | 4.97E−05 |
| AB12T3 | 5.46E−10 | 9.47E+04 | 5.17E−05 |
| AB12T4 | 2.58E−10 | 1.20E+05 | 3.09E−05 |
| AB12T5 | 3.65E−10 | 9.24E+04 | 2.28E−05 |
| AB12T6 | 3.78E−10 | 2.41E+05 | 2.41E−05 |
| AB12T7 | 3.59E−10 | 6.58E+04 | 2.36E−05 |
| AB12T8 | 1.20E−10 | 1.08E+05 | 1.30E−05 |
| AB12T9 | 2.98E−10 | 1.81E+05 | 5.40E−05 |

Example 6: Detection of the Activity of Anti-Human LAG-3 Antibodies to Block the Binding of Human LAG-3 to MHC II The ligand for LAG-3 is MHC class II (MHC II), so the LAG-3/MHC II kit (CISBIO, Cat. No. ADK000CLAPEF) was used to detect the activity of AB12T3 and AB12T4 antibodies of blocking LAG-3/MHC II which can be used to assess the biological activity of the relevant antibody.

The principle of this experiment is that LAG-3 and MHC II are labeled (LAG-3-Tag1, MHC II-Tag2), respectively, and then antibodies against these two tags (anti-Tag1-Eu$^{3+}$, anti-Tag2-XL665) are added. Anti-Tag1-Eu$^{3+}$ is a donor of HTRF (Homogeneous Time-Resolved Fluorescence), and anti-Tag2-XL665 acts as a receptor for HTRF. When the two molecules are close to each other, the fluorescence energy is transferred from the donor to the acceptor, accompanied by appearance of a fluorescent signal at 650 nm. By measurement of the signals, the binding effect of LAG-3 and MHC II can be evaluated.

Figure 2:
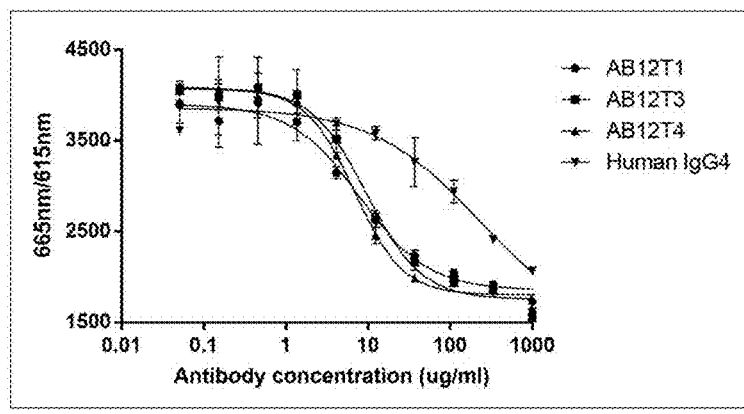
FIG. 2 shows the results of the in vitro blocking assay of the binding of LAG-3 to MHC II with humanized antibodies AB12T1, AB12T3 and AB12T4 of Example 6.

The specific procedure is as follows: according to the reaction system of 20 μl, 4 μl of LAG-3, 4 μl of MHC II protein, and 2 μl of the reference antibody AB12T1 (i.e., BMS 986016, the heavy chain thereof as shown in SEQ ID NO: 36, light chain as shown in SEQ ID NO: 37), AB12T3 and AB12T4 antibodies (antibody concentration was 3-fold diluted starting from 1 μg/ul) were added, mixed and incubated for 15 min at room temperature. After mixing the anti-Tag1-Eu$^{3+}$ and anti-Tag2-XL665 in equal volumes, each well was added with 10 μl, mixed well, sealed with a film, and incubated for 1 hour at room temperature. The fluorescent signal at 650 nm was detected by a pherastar microplate reader (BMG, Germany), and the IC$_{50}$ value of LAG-3 antibody blocking the binding of LAG-3 and MHC II was calculated. The results were shown in Table 5. According to the results, the fitting curves were shown in FIG. 2. The reference antibody AB12T1 and the humanized antibodies AB12T3 and AB12T4 can effectively block the binding of LAG-3 and MHC II. Among them, AB12T4 has the strongest blocking effect and is superior to the reference antibody AB12T1.

TABLE 5

IC$_{50}$ values of AB12T3 and AB12T4 blocking LAG-3/MHC II in vitro

| | Antibody to be tested | | |
|---|---|---|---|
| | AB12T1 | AB12T3 | AB12T4 |
| IC$_{50}$ (μg/ml) | 7.617 | 9.451 | 6.695 |

Example 7: Evaluation of Biological Activity of Anti-Human LAG-3 Antibody Blocking the Binding of LAG-3 to MHC II on Cancer Cell Surface Human epidermal cancer cell line A431 (purchased from Nanjing Cobioer Company) is an MHC II positive expression cell line. LAG-3-His was used to bind to A431 cells, PE anti-His (purchased from Biolegend) was used to detect signals, and FACS was used to detect the blocking effect of the reference antibody AB12T1 and AB12T4 on LAG-3/A431. The method was also used to evaluate the biological activity of relevant antibodies.

The specific process is as follows:
A431 cells were trypsinized, resuspended in PBS, and the cell density was adjusted to 5×10$^6$ cells/mL, 100 μL/well. Serial dilutions of AB12T1, AB12T3, and AB12T4 antibody diluted with 12 μg/mL of LAG-3-His antigen was added to 100μl of the cell suspension, mixed well, and the mixture was incubated at 4° C. for 1 hour. The cells were washed twice with pre-cooled PBS, resuspended in 100μl of solution containing 5μl of PE anti-His, and incubated at 4° C. for 0.5 hours, washed twice with pre-cooled PBS, and resuspended in PBS. The fluorescence signal of PE was detected by flow cytometry (purchased from Beckman, model CytoFLEX), and GraphPad Prism6 was used to calculate the IC50 value of LAG-3 antibody blocking the binding of LAG-3-His and A431. The results were shown in Table 6.

Figure 3:
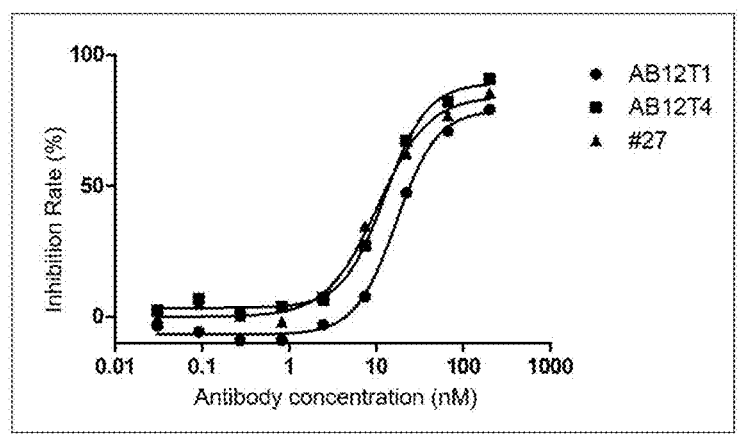
FIG. 3 shows the results of the blocking assay of the binding of LAG-3 to MHC II on the surface of cancer cells with humanized antibody AB12T1, AB12T4 and murine antibody #27 of Example 7.

According to the results, the fitting curves were shown in FIG. 3. The positive control antibody AB and the humanized antibody AB12T4 and the murine antibody #27 can effectively block the binding of LAG-3 to A431, wherein the blocking effect of AB12T4 is stronger than that of AB12T1, and the maximum inhibition rate thereof is the highest.

TABLE 6

IC$_{50}$ values of AB12T1 and AB12T4 blocking the binding of LAG-3 to A431 cells in vitro

| Antibody to be tested | AB12T1 | AB12T4 | #27 |
|---|---|---|---|
| IC$_{50}$ (nM) | 16.99 | 12.66 | 10.37 |
| Maximum inhibition % | 78.91 | 89.32 | 84.25 |

Example 8: Affinity Detection of Anti-Human LAG-3 Antibody to Human/Monkey LAG-3

Binding affinity of AB12T1, AB12T4, AB12T8 to CHO-hLAG-3 (CHO cells expressing human LAG-3, prepared by Kelun Biotech Co., Ltd.) and CHO-cynoLAG-3 cells (expressing cynomolgus monkey LAG-3, prepared by Kelun Biotech Co., Ltd.) were detected by FACS. The AB12T1, AB12T4 and AB12T8 antibodies were labeled with NHS-Fluorescein (Thermo, Cat. No. 46410) with FITC labeling efficiencies of 3.7, 3.8 and 3.6, respectively. 5×10$^5$ cells per tube of CHO-cynoLAG-3 and CHO-hLAG-3 cells were taken respectively. FITC-AB12T1 and FITC-AB12T4 antibodies were 3-fold diluted in PBS (1% BSA), starting from 1 μM, with a total of 11 concentration points. The dilutions were mixed with cells at a ratio of 1:1, and incubated for 30 minutes at room temperature, followed by washing 3 times with pre-cooled PBS and detection by flow cytometry (Benckman, model CytoFlex). The signal values were input into GraphPad Prism to calculate the EC$_{50}$ values. The results were shown in Table 7.

Figure 4:
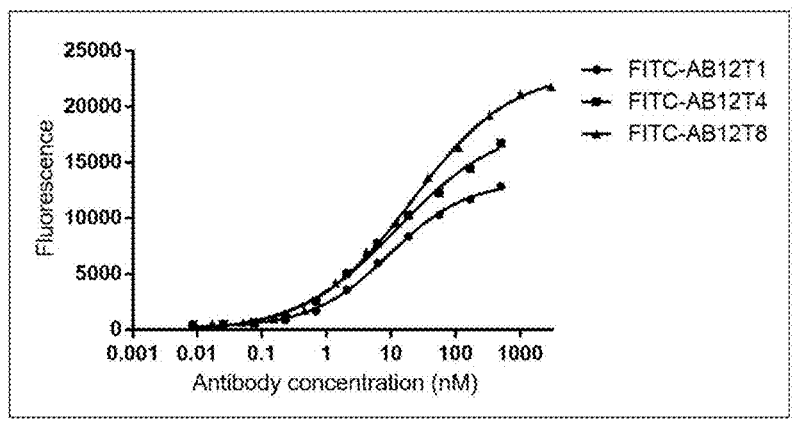
FIG. 4 shows the results of FACS detection of the affinity of humanized antibodies AB12T1, AB12T4, AB12T8 to human LAG-3 of Example 8.
Figure 5:
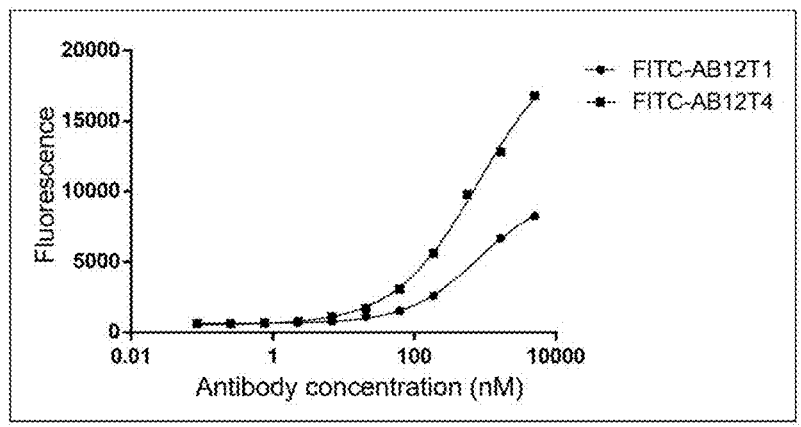
FIG. 5 shows the results of FACS detection of the affinity of humanized antibody AB12T1, AB12T4 to monkey LAG-3 of Example 8.

The fitting curves based on to the results were shown in FIG. 4. The results show that AB12T4 and AB12T8 have the same affinity to CHO-hLAG-3 cells as AB12T1, but the maximum signal values of AB12T4 and AB12T8 are higher. According to FIG. 5 showing the fitting curves based on to the results, there is no significant difference in the affinity between AB12T1 and AB12T4 to CHO-cynoLAG-3 cells, but the maximum signal value of AB12T4 is higher. According to the results of FIG. 4 and FIG. 5, although the EC$_{50}$ of AB12T4 and the reference antibody AB are close, the maximum signal value of AB12T4 is much higher than that of AB12T1, thus, at the same concentration, the amount of LAG-3 proteins bound by AB12T4 is higher than the amount of LAG-3 proteins bound by AB12T1, resulting in a higher target occupancy rate for AB12T4.

TABLE 7

| | CHO-hLAG-3 | CHO-cynoLAG-3 |
|---|---|---|
| Antibody to be tested | $EC_{50}$ (nM) | $EC_{50}$ (nM) |
| AB12T1 | 9.41 | 793.0 |
| AB12T4 | 12.79 | 803.1 |
| AB12T8 | 13.29 | Not done |

$EC_{50}$ values for binding of AB12T1, AB12T4 and AB12T8 to CHO-hLAG-3 and CHO-cynoLAG-3.

Example 9: Determination of Tm Value of Anti-Human LAG-3 Antibodies

The Tm value of the anti-LAG-3 antibodies ware determined by DSF (Differential Fluorescence Scanning) method. The specific experimental procedure was as follows. AB12T1, AB12T3, AB12T4, and AB12T8 were diluted to 1 mg/ml with PBS, 12.5 μL of which were added with 5 μL of 40×SYPRO Orange dye (purchased from Life Technologies, Cat. No. 4306737) and 7.5 μL of ddH$_2$O. Reactions were performed using a Q-PCR instrument (AB Applied Biosystems, 7500), Q-PCR parameter settings: Target (ROX), program (25° C., 3 min; 1% rate, 95° C.; 95° C., 2 min).

The results are shown in Table 8. The results show that the Tm value of AB12T4 is 1.2° C. higher than that of the reference antibody AB12T1, and the Tm value of AB12T8 is 4.9° C. higher than that of AB12T1. Overall, the anti-human LAG-3 antibodies have good thermal stability.

TABLE 8

Tm values for AB12T1, AB12T3 and AB12T4

| Antibody to be tested | Tm (° C.) |
|---|---|
| AB12T1 | 70.06 |
| AB12T3 | 69.48 |
| AB12T4 | 71.23 |
| AB12T8 | 74.95 |

Example 10: Detection of Biological Activity of Anti-LAG-3 Antibody in Enhancing T Cell Response In this experiment, the level of IL-2 cytokine secretion by CD8$^+$ T cells stimulated by AB12T1, AB12T3 and AB12T4 antibodies was determined by ELISA to evaluate the biological activity of the antibody.

PBMC cells were prepared from fresh human blood by density gradient centrifugation, and CD8$^+$ T cells were obtained using a human CD8$^+$ T cell sorting kit (STEMCELL, #19053). The obtained CD8$^+$ T cells were resuspended in a medium containing 1 ng/ml of SEB, adjusted to a cell density of 5.6×10$^5$/ml, and evenly distributed to a 96-well plate at 180 μl per well (10$^5$ cells/well). The antibody was 10-fold diluted, and 20 μl of which was added to each well. Each kind of antibody has 3 replicates for each concentration. After 48 hours, the cell supernatant was collected by centrifugation, and the amount of IL-2 secreted in the supernatant was measured using an IL-2 ELISA kit (BD, #555190).

Figure 6:
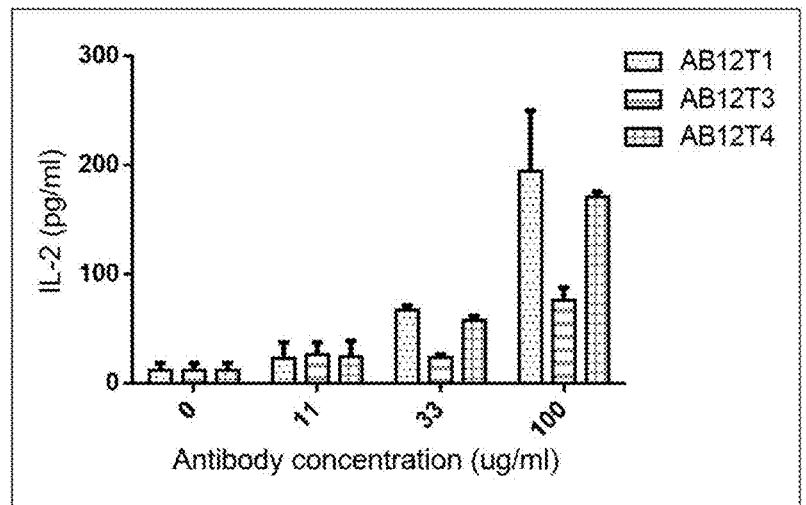
FIG. 6 shows the results of detection of the effects of the humanized antibodies AB12T1, AB12T3 and AB12T4 on T cell activity of Example 10.

Results are shown in FIG. 6, as the concentrations of the antibodies AB12T1, AB12T3 and AB12T4 increased, the amount of IL-2 produced by the CD8$^+$ T cells also increased, indicating the ability to enhance the CD8$^+$ T cell response.

The above results indicate that both AB12T4 and AB12T3 have the ability to enhance T cell activity, and AB12T4 has a stronger promoting effect.

Example 11: Evaluation of Anti-Tumor Activity of Anti-LAG-3 Humanized Antibody in Human Breast Cancer Model of Human Immune Reconstituted Mice (NPG Mice)

Female NPG mice (purchased from Beijing Vital River Laboratory Animal Technology Co., Ltd.) were pretreated with butanediol mesylate (SIGMA, Cat: B2635-10G); fresh PBMC cells were taken and resuspended in PBS; 4×10$^6$ (0.2 mL) PBMC were injected intraperitoneally into each mouse. On Day 3 after PBMC injection, human breast cancer cells HCC1954 (purchased from the Chinese Academy of Sciences cell bank) were inoculated to establish a breast cancer model. Specifically, HCC1954 cells were cultured in RPMI-1640 medium containing 10% FBS at the conditions of 5% CO$_2$, 37° C.; HCC1954 cells in logarithmic growth phase were collected, resuspended at 5×10$^7$/mL in RPMI-1640 serum-free medium, and then mixed with matrigel (Corning, Cat: 354234) in a volume ratio of 1:1. Then, the cells were inoculated subcutaneously in NPG mice, with 0.2 mL per mouse, that is, 5×10$^6$ cells per mouse.

Figure 7:
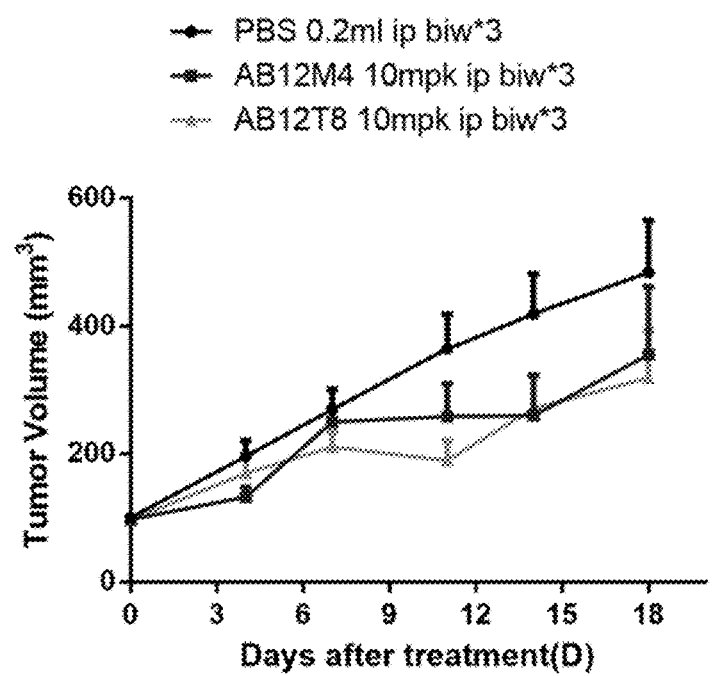
FIG. 7 shows the results of the tumor suppressive activity of the humanized antibody AB12T8 in the human breast cancer model of human immune-reconstituted mice (NPG mice) of Example 11.

On the 12th day after PBMC injection, mice were randomly grouped according to tumor volume and body weight into PBS (negative control) group, AB12T8 single drug group, and anti-PD-1 antibody AB12M4 single drug group (AB12M4, see Chinese patent application CN106519034A), and administered with the drugs on the same day. The drugs were administered by intraperitoneal injection, twice a week for a total of 3 weeks. The dose for PBS is 0.2 ml, the doses for AB12T8 and AB12M4 are 10 mpk respectively. The tumor volume of the mice was observed and periodically measured after administration, and results were shown in FIG. 7.

It can be seen from the results that the AB12T8 single drug group had a significant inhibitory effect on the tumor growth of the HCC1954 breast cancer model, and had a stronger inhibitory effect than the AB12M4 single drug group. All treatment groups had mouse death during the observation period, but all were caused by graft-versus-host disease (GVHD). This result indicates that the antibodies of the present disclosure do not exhibit significant drug toxicity and have good safety.

Figure 8:
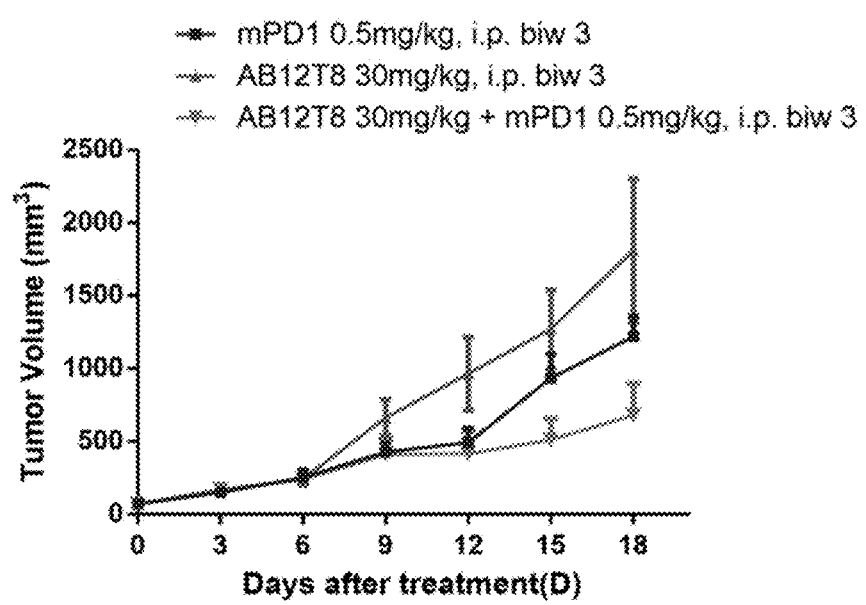
FIG. 8 shows the results of tumor suppressive activity of the humanized antibody AB12T8 alone or in the combination with PD-1 antibody in the colon cancer model of hLAG-3 transgenic mice of Example 12.

Example 12: Evaluation of Anti-Tumor Activity of Anti-LAG-3 Humanized Antibody in Colon Cancer Model of hLAG-3 Transgenic Mice MC38 cells (mouse colon cancer cells, purchased from Nanjing Cobioer Biotechnology Co., Ltd.) were cultured in RPMI1640 medium containing 10% fetal bovine serum at 37° C. under 5% CO$_2$. The MC38 cells in the exponential growth phase were collected, resuspended in PBS to a suitable concentration, and inoculated subcutaneously into female B-hLAG-3 mice (purchased from the Southern Model Animal Center) to establish a colon cancer model. When the average tumor volume was about 91.56 mm$^3$, the mice were randomly grouped according to tumor size into AB12T8 single drug group, anti-mouse PD-1 antibody (abbreviated as mPD1, purchased from BioxCell, article number: BE0146) single drug group and AB12T8 and anti-mouse PD-1 (mPD1) antibody combination group. The drugs were administrated by intraperitoneal injection, twice a week for a total of 3 weeks, wherein the dose for AB12T8 is 30 mg/kg, the dose for mPD1 is 0.5 mg/kg, the dose for combination group is 30 mg/kg of AB12T8 and 0.5 mg/kg of mPD1. The tumor volume of the mice was observed and periodically measured after administration, and results are shown in FIG. 8.

It can be seen from the results that the AB12T8 single drug group has a certain inhibitory effect on the tumor growth of the MC38 colon cancer xenograft model, and the AB12T8 and anti-mouse PD-1 combination group has obvious synergistic effects with respect to each of the antibody single drug groups. All the treatment groups showed no animal death and significant animal weight loss during the observation period, and showed no obvious drug toxicity. This result indicates that the mice are well tolerated the antibody during the treatment, and the antibody of the present disclosure has good safety.

While specific embodiments of the present disclosure have been described in detail, those skilled in the art will understand that according to all the teachings that have been disclosed, various modifications and substitutions can be made to these details, which are still within the protection scope of the present disclosure. The full scope of the invention is given by the appended claims and any equivalents thereof.

What is claimed:

1. An antibody or antigen-binding fragment thereof which is capable of specifically binding to LAG-3, comprising:
   (1) three CDRs of the heavy chain variable region (VH) as shown in SEQ ID NO: 1; and three CDRs of the light chain variable region (VL) as shown in SEQ ID NO: 2;
   (2) three CDRs of the heavy chain variable region (VH) as shown in SEQ ID NO: 16; and three CDRs of the light chain variable region (VL) as shown in SEQ ID NO: 17;
   (3) three CDRs of the heavy chain variable region (VH) as shown in SEQ ID NO: 18; and three CDRs of the light chain variable region (VL) as shown in SEQ ID NO: 19;
   (4) three CDRs of the heavy chain variable region (VH) as shown in SEQ ID NO: 20; and three CDRs of the light chain variable region (VL) as shown in SEQ ID NO: 21;
   (5) three CDRs of the heavy chain variable region (VH) as shown in SEQ ID NO: 22; and three CDRs of the light chain variable region (VL) as shown in SEQ ID NO: 23;
   (6) three CDRs of the heavy chain variable region (VH) as shown in SEQ ID NO: 24; and three CDRs of the light chain variable region (VL) as shown in SEQ ID NO: 25; or
   (7) three CDRs of the heavy chain variable region (VH) as shown in SEQ ID NO: 26; and three CDRs of the light chain variable region (VL) as shown in SEQ ID NO: 27;

wherein, the three CDRs of the heavy chain variable region (VH) and the three CDRs of the light chain variable region (VL) are defined by the Kabat, Chothia or IMGT numbering system.

2. The antibody or an antigen-binding fragment thereof according to claim 1, wherein:
   (1) the antibody or an antigen-binding fragment comprises the following six CDRs defined in accordance with the IMGT numbering system: VH CDR1 as set forth in SEQ ID NO: 3; VH CDR2 as set forth in SEQ ID NO: 4; VH CDR3 as set forth in SEQ ID NO: 5; VLCDR1 as set forth in SEQ ID NO: 6; VL CDR2 as set forth in SEQ ID NO: 7; and VL CDR3 as set forth in SEQ ID NO: 8;
   or
   (2) the antibody or an antigen-binding fragment comprises the following six CDRs defined in accordance with the Chothia numbering system:
   (2a) VH CDR1 as set forth in SEQ ID NO: 9; VH CDR2 as set forth in SEQ ID NO: 10; VH CDR3 as set forth in SEQ ID NO: 11; VL CDR1 as set forth in SEQ ID NO: 12; VL CDR2 as set forth in SEQ ID NO: 13; and VL CDR3 as set forth in SEQ ID NO: 8; or,
   (2b) VH CDR1 as set forth in SEQ ID NO: 9; VH CDR2 as set forth in SEQ ID NO: 10; VHCDR3 as set forth in SEQ ID NO: 11; VL CDR1 as set forth in SEQ ID NO: 12; VL CDR2 as set forth in SEQ ID NO: 54; and VL CDR3 as set forth in SEQ ID NO: 8;
   or
   (3) the antibody or an antigen-binding fragment comprises the following six CDRs defined in accordance with the Kabat numbering system:

(3a) VH CDR1 as set forth in SEQ ID NO: 14; VH CDR2 as set forth in SEQ ID NO: 15; VH CDR3 as set forth in SEQ ID NO: 11; VLCDR1 as set forth in SEQ ID NO: 12; VL CDR2 as set forth in SEQ ID NO: 13; and VL CDR3 as set forth in SEQ ID NO: 8; or, (3b) VH CDR1 as set forth in SEQ ID NO: 14; VH CDR2 as set forth in SEQ ID NO: 55; VH CDR3 as set forth in SEQ ID NO: 11; VLCDR1 as set forth in SEQ ID NO: 12; VL CDR2 as set forth in SEQ ID NO: 13; and VL CDR3 as set forth in SEQ ID NO: 8; or, (3c) VH CDR1 as set forth in SEQ ID NO: 56; VH CDR2 as set forth in SEQ ID NO: 57; VH CDR3 as set forth in SEQ ID NO: 11; VLCDR1 as set forth in SEQ ID NO: 12; VL CDR2 as set forth in SEQ ID NO: 54; and VL CDR3 as set forth in SEQ ID NO: 8; or, (3d) VH CDR1 as set forth in SEQ ID NO: 14; VH CDR2 as set forth in SEQ ID NO: 58; VH CDR3 as set forth in SEQ ID NO: 11; VL CDR1 as set forth in SEQ ID NO: 12; VL CDR2 as set forth in SEQ ID NO: 13; and VL CDR3 as set forth in SEQ ID NO: 8.

3. The antibody or an antigen-binding fragment thereof according to claim 1, wherein, the antibody or an antigen-binding fragment thereof comprises:
(1) VH as set forth in SEQ ID NO: 1, and VL as set forth in SEQ ID NO: 2;
(2) VH as set forth in SEQ ID NO: 16, and VL as set forth in SEQ ID NO: 17;
(3) VH as set forth in SEQ ID NO: 18, and VL as set forth in SEQ ID NO: 19;
(4) VH as set forth in SEQ ID NO: 20, and VL as set forth in SEQ ID NO: 21;
(5) VH as set forth in SEQ ID NO: 22, and VL as set forth in SEQ ID NO: 23;
(6) VH as set forth in SEQ ID NO: 24, and VL as set forth in SEQ ID NO: 25; or
(7) VH as set forth in SEQ ID NO: 26, and VL as set forth in SEQ ID NO: 27.

4. The antibody or an antigen-binding fragment thereof according to claim 1, wherein,
the antibody or an antigen-binding fragment further comprises: (a) a heavy chain constant region (CH) of a human immunoglobulin or a variant thereof, wherein the variant is described below, and (b) a light chain constant region (CL) of a human immunoglobulin;
wherein the variant of heavy chain constant region (CH) is selected from the following:
(1) a variant of human IgG1 heavy chain constant region, wherein the variant comprises the following substitutions: Leu234Ala, Leu235Ala and Gly237Ala, compared to the wild-type sequence from which it is derived;
(2) a variant of human IgG1 heavy chain constant region, wherein the variant comprises the following substitutions: Asn297Ala, Asp356Glu and Leu358Met, compared to the wild-type sequence from which it is derived;
(3) a variant of human IgG4 heavy chain constant region, wherein the variant comprises the following substitution: Ser228Pro, compared to the wild-type sequence from which it is derived;
wherein the amino acid positions mentioned above are based on EU numbering system.

5. The antibody or an antigen-binding fragment thereof according to claim 1, wherein, the antibody or an antigen-binding fragment thereof is a chimeric antibody or a humanized antibody.

6. The antibody or an antigen-binding fragment thereof according to claim 1, wherein, the antibody or an antigen-binding fragment thereof comprises:
(1) a heavy chain having a sequence as set forth in SEQ ID NO: 38, and a light chain having a sequence as set forth in SEQ ID NO: 39;
(2) a heavy chain having a sequence as set forth in SEQ ID NO: 40, and a light chain having a sequence as set forth in SEQ ID NO: 41;
(3) a heavy chain having a sequence as set forth in SEQ ID NO: 42, and a light chain having a sequence as set forth in SEQ ID NO: 43;
(4) a heavy chain having a sequence as set forth in SEQ ID NO: 44, and a light chain having a sequence as set forth in SEQ ID NO: 45;
(5) a heavy chain having a sequence as set forth in SEQ ID NO: 46, and a light chain having a sequence as set forth in SEQ ID NO: 47;
(6) a heavy chain having a sequence as set forth in SEQ ID NO: 48, and a light chain having a sequence as set forth in SEQ ID NO: 49;
(7) a heavy chain having a sequence as set forth in SEQ ID NO: 50, and a light chain having a sequence as set forth in SEQ ID NO: 51; or
(8) a heavy chain having a sequence as set forth in SEQ ID NO: 52, and a light chain having a sequence as set forth in SEQ ID NO: 53.

7. The antibody or an antigen-binding fragment thereof according to claim 1, wherein, the antibody or an antigen-binding fragment thereof is selected from scFv, Fab, Fab', F(ab')$_2$, Fv fragment, disulfide bond ligated Fv (dsFv), diabody, bispecific antibody and multi-specific antibody.

8. An isolated nucleic acid molecule, encoding an antibody or antigen-binding fragment thereof according to claim 1, or a heavy chain variable region and a light chain variable region thereof.

9. The isolated nucleic acid molecule of claim 8, comprising a nucleic acid molecule encoding an antibody heavy chain variable region, and a nucleic acid molecule encoding an antibody light chain variable region, wherein,
the nucleic acid molecule encoding an antibody heavy chain variable region has a sequence selected from:
(a) a nucleic acid sequence as shown in SEQ ID NO:34, or
(b) a sequence which is essentially the same as the sequence described in (a),
the nucleic acid molecule encoding an antibody light chain variable region has a sequence selected from:
(d) a nucleic acid sequence as shown in SEQ ID NO:35, or
(e) a sequence which is essentially the same as the sequence described in (d).

10. A method of producing the antibody or antigen-binding fragment thereof according to claim 1, which comprises culturing a host cell comprising an isolated nucleic acid molecule encoding the antibody or antigen-binding fragment thereof under conditions permitting expression of the antibody or antigen-binding fragment thereof, and recovering the antibody or antigen-binding fragment thereof from the host cell culture.

11. A hybridoma cell line, wherein:
hybridoma cell line #27, deposited in China Center for Type Culture Collection (CCTCC), with an accession number of CCTCC NO. C2017183.

12. A pharmaceutical composition, comprising the antibody or an antigen-binding fragment thereof according to claim 1 or a prodrug thereof, and a pharmaceutically acceptable carrier and/or excipient.

13. The pharmaceutical composition according to claim 12, further comprising a second antibody specifically binding to a ligand or receptor or a nucleic acid encoding the second antibody, wherein the ligand or receptor is selected from: PD-1, PD-L1, PD-L2, TIM-3, TIGIT, VISTA, CTLA-4, OX40, BTLA, 4-IBB, CD96, CD27, CD28, CD40, LAIR1, CD160, 2B4, TGF-R, KIR, ICOS, GITR, CD3, CD30, BAFFR, HVEM, CD7, LIGHT, SLAMF7, NKp80, B7-H3, and any combination thereof.

14. An immunogenic composition, comprising the antibody or an antigen-binding fragment thereof of claim 1 and an immunogen.

15. A method of increasing immune cell activity and/or enhancing an immune response in a subject, the method comprising administering to a subject in need thereof an effective amount of the antibody or an antigen-binding fragment thereof of claim 1, or a pharmaceutical composition or immunogenic composition comprising the antibody or an antigen-binding fragment thereof.

16. A method for treating a tumor, an infection or an auto-immune disease in a subject, the method comprising administering to a subject in need thereof an effective amount of the antibody or an antigen binding fragment thereof of claim 1, or a pharmaceutical composition or immunogenic composition comprising the antibody or an antigen-binding fragment thereof.

17. The antibody or an antigen-binding fragment thereof of claim 4, wherein, the heavy chain constant region is selected from the following:
(1) human IgG1 heavy chain constant region;
(2) human IgG4 heavy chain constant region.

18. The antibody or an antigen-binding fragment thereof of claim 4, wherein, the antibody or antigen-binding fragment thereof comprises the heavy chain constant region (CH) as set forth in any one of SEQ ID NOs: 28-32; and/or, the antibody or antigen-binding fragment thereof comprises the light chain constant region (CL) as set forth in SEQ ID NO: 33.

19. The pharmaceutical composition of claim 12, further comprising an additional active pharmaceutical agent which is selected from a drug having anti-cancer activity, a drug for treating infection and a drug for treating autoimmune disease.

20. The pharmaceutical composition of claim 13, wherein, the antibody or an antigen-binding fragment thereof that binds to human PD-1 is selected from AB12M4 or antigen-binding fragment thereof, Nivolumab or antigen-binding fragment thereof, or Pembrolizumab or antigen-binding fragment thereof.

21. The immunogenic composition of claim 14, wherein, the immunogen is selected from a tumor-associated antigen, a tumor cell, a dendritic cell sensitized by the antigen, and any combination thereof; or, the immunogen is selected from a pathogen-related antigen, an inactivated or attenuated pathogen, a dendritic cell sensitized by the antigen, and any combination thereof.

22. The method of claim 15, wherein the method further comprises administering to the subject a second antibody, the second antibody specifically binds to a ligand or receptor selected from a group consisting of: PD-1, PD-L1, PD-L2, TIM-3, TIGIT, VISTA, CTLA-4, OX40, BTLA, 4-1BB, CD96, CD27, CD28, CD40, LAIR1, CD160, 2B4, TGF-R, KIR, ICOS, GITR, CD3, CD30, BAFFR, HVEM, CD7, LIGHT, SLAMF7, NKp80, B7-H3, and any combination thereof.

23. The method of claim 22, wherein the antibody or antigen-binding fragment thereof that binds to human PD-1 is selected from AB12M4 or antigen-binding fragment thereof, Nivolumab or antigen-binding fragment thereof, and Pembrolizumab or antigen-binding fragment thereof.

24. The method of claim 16, wherein the method further comprises administering to the subject a second antibody, the second antibody specifically binds to a receptor or ligand selected from a group consisting of: PD-1, PD-L1, PD-L2, TIM-3, TIGIT, VISTA, CTLA-4, OX40, BTLA, 4-1BB, CD96, CD27, CD28, CD40, LAIR1, CD160, 2B4, TGF-R, KIR, ICOS, GITR, CD3, CD30, BAFFR, HVEM, CD7, LIGHT, SLAMF7, NKp80, B7-H3, and any combination thereof.

25. The method of claim 24, wherein the antibody or antigen-binding fragment thereof that binds to human PD-1 is selected from a group consisting of: AB12M4 or antigen-binding fragment thereof, Nivolumab or antigen-binding fragment thereof, and Pembrolizumab or antigen-binding fragment thereof.

26. The method of claim 16, when the method is for treating a tumor, the method further comprises administering to the subject an additional anti-tumor therapy, selected from surgery, chemotherapy, radiation therapy, targeted therapy, immunotherapy, hormone therapy, gene therapy, palliative care, and any combination thereof.

27. The method of claim 16, characterized by one or more of the following:
(1) the tumor is selected from the group consisting of ovarian cancer, melanoma, prostate cancer, intestinal cancer, gastric cancer, esophageal cancer, breast cancer, lung cancer, kidney cancer, pancreatic cancer, uterine cancer, liver cancer, bladder cancer, cervical cancer, oral cancer, brain cancer, testicular cancer, skin cancer, thyroid cancer, and hematological malignancy;
(2) the infection is selected from the group consisting of a viral infection, a bacterial infection, a fungal infection, and a parasitic infection;
(3) the autoimmune disease is selected from the group consisting of rheumatoid arthritis, psoriasis, systemic lupus erythematosus, primary biliary cirrhosis, autoimmune hemolytic anemia, autoimmune thrombocytopenic purpura, insulin-dependent diabetes, Graves' disease, myasthenia gravis, autoimmune hepatitis and multiple sclerosis.

28. The method of claim 27, wherein:
the melanoma comprises metastatic malignant melanoma;
the intestinal cancer comprises colorectal cancer or small intestine cancer;
the kidney cancer comprises clear cell carcinoma;
the hematological malignancy comprises myeloma, or chronic or acute leukemia.

\* \* \* \* \*

SEQUENCE LISTING

<160> NUMBER OF SEQ ID NOS: 58

<210> SEQ ID NO 1
<211> LENGTH: 122
<212> TYPE: PRT
<213> ORGANISM: Artificial sequence
<220> FEATURE:
<223> OTHER INFORMATION: #27 VH

<400> SEQUENCE: 1

Asp Val His Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Phe
            20                  25                  30

Tyr Ser Trp His Trp Ile Arg Gln Phe Pro Gly Asn Lys Leu Glu Trp
        35                  40                  45

Met Gly Cys Ile Gln Tyr Ser Gly Asp Thr Asp Ser Asn Pro Ser Leu
    50                  55                  60

Lys Ser Arg Ile Ser Ile Thr Arg Asp Thr Ser Glu Asn Gln Leu Phe
65                  70                  75                  80

Leu His Leu Asn Ser Val Thr Thr Glu Asp Thr Ala Thr Tyr Tyr Cys
                85                  90                  95

Ala Arg Ser Pro Tyr Asp Ser Asp Pro Tyr Tyr Val Met Asp Tyr Trp
            100                 105                 110

Gly Gln Gly Thr Ser Val Thr Val Ser Ser
        115                 120

<210> SEQ ID NO 2
<211> LENGTH: 113
<212> TYPE: PRT
<213> ORGANISM: Artificial sequence
<220> FEATURE:
<223> OTHER INFORMATION: #27 VL

<400> SEQUENCE: 2

Asp Ile Val Met Ser Gln Ser Pro Ser Ser Leu Ala Val Ser Val Gly
1               5                   10                  15

Glu Lys Ile Thr Met Thr Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Thr Leu Leu Ile Tyr Trp Ala Ser Thr Arg Asp Ser Gly Val
    50                  55                  60

Pro Asp Arg Leu Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

```
Tyr Tyr Ala Tyr Pro Tyr Thr Phe Gly Gly Gly Thr Lys Leu Glu Thr
                100                 105                 110
Lys

<210> SEQ ID NO 3
<211> LENGTH: 9
<212> TYPE: PRT
<213> ORGANISM: Artificial sequence
<220> FEATURE:
<223> OTHER INFORMATION: IMGT #27 CDR-H1

<400> SEQUENCE: 3

Gly Tyr Ser Ile Thr Ser Phe Tyr Ser
1               5

<210> SEQ ID NO 4
<211> LENGTH: 7
<212> TYPE: PRT
<213> ORGANISM: Artificial sequence
<220> FEATURE:
<223> OTHER INFORMATION: IMGT #27 CDR-H2

<400> SEQUENCE: 4

Ile Gln Tyr Ser Gly Asp Thr
1               5

<210> SEQ ID NO 5
<211> LENGTH: 15
<212> TYPE: PRT
<213> ORGANISM: Artificial sequence
<220> FEATURE:
<223> OTHER INFORMATION: IMGT #27 CDR-H3

<400> SEQUENCE: 5

Ala Arg Ser Pro Tyr Asp Ser Asp Pro Tyr Tyr Val Met Asp Tyr
1               5                   10                  15

<210> SEQ ID NO 6
<211> LENGTH: 12
<212> TYPE: PRT
<213> ORGANISM: Artificial sequence
<220> FEATURE:
<223> OTHER INFORMATION: IMGT #27 CDR-L1

<400> SEQUENCE: 6

Gln Ser Leu Leu Tyr Ser Gly Asn Gln Lys Asn Tyr
1               5                   10

<210> SEQ ID NO 7

<400> SEQUENCE: 7

000

<210> SEQ ID NO 8
<211> LENGTH: 9
<212> TYPE: PRT
<213> ORGANISM: Artificial sequence
<220> FEATURE:
<223> OTHER INFORMATION: IMGT/Chothia/Kabat #27 CDR-L3

<400> SEQUENCE: 8

Gln Gln Tyr Tyr Ala Tyr Pro Tyr Thr
1               5
```

```
<210> SEQ ID NO 9
<211> LENGTH: 8
<212> TYPE: PRT
<213> ORGANISM: Artificial sequence
<220> FEATURE:
<223> OTHER INFORMATION: Chothia #27 CDR-H1

<400> SEQUENCE: 9

Gly Tyr Ser Ile Thr Ser Phe Tyr
1               5

<210> SEQ ID NO 10
<211> LENGTH: 5
<212> TYPE: PRT
<213> ORGANISM: Artificial sequence
<220> FEATURE:
<223> OTHER INFORMATION: Chothia #27 CDR-H2

<400> SEQUENCE: 10

Gln Tyr Ser Gly Asp
1               5

<210> SEQ ID NO 11
<211> LENGTH: 13
<212> TYPE: PRT
<213> ORGANISM: Artificial sequence
<220> FEATURE:
<223> OTHER INFORMATION: Chothia/Kabat #27 CDR-H3

<400> SEQUENCE: 11

Ser Pro Tyr Asp Ser Asp Pro Tyr Tyr Val Met Asp Tyr
1               5                   10

<210> SEQ ID NO 12
<211> LENGTH: 17
<212> TYPE: PRT
<213> ORGANISM: Artificial sequence
<220> FEATURE:
<223> OTHER INFORMATION: Chothia/Kabat #27 CDR-L1

<400> SEQUENCE: 12

Lys Ser Ser Gln Ser Leu Leu Tyr Ser Gly Asn Gln Lys Asn Tyr Leu
1               5                   10                  15

Ala

<210> SEQ ID NO 13
<211> LENGTH: 7
<212> TYPE: PRT
<213> ORGANISM: Artificial sequence
<220> FEATURE:
<223> OTHER INFORMATION: Chothia/Kabat #27 CDR-L2

<400> SEQUENCE: 13

Trp Ala Ser Thr Arg Asp Ser
1               5

<210> SEQ ID NO 14
<211> LENGTH: 6
<212> TYPE: PRT
<213> ORGANISM: Artificial sequence
<220> FEATURE:
<223> OTHER INFORMATION: Kabat #27 CDR-H1

<400> SEQUENCE: 14

Ser Phe Tyr Ser Trp His
1               5
```

```
<210> SEQ ID NO 15
<211> LENGTH: 16
<212> TYPE: PRT
<213> ORGANISM: Artificial sequence
<220> FEATURE:
<223> OTHER INFORMATION: Kabat #27 CDR-H2

<400> SEQUENCE: 15

Cys Ile Gln Tyr Ser Gly Asp Thr Asp Ser Asn Pro Ser Leu Lys Ser
1               5                   10                  15

<210> SEQ ID NO 16
<211> LENGTH: 122
<212> TYPE: PRT
<213> ORGANISM: Artificial sequence
<220> FEATURE:
<223> OTHER INFORMATION: AB12T3 VH

<400> SEQUENCE: 16

Asp Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Phe
            20                  25                  30

Tyr Ser Trp His Trp Ile Arg Gln His Pro Gly Lys Gly Leu Glu Trp
        35                  40                  45

Met Gly Cys Ile Gln Tyr Ser Gly Asp Thr Asp Ser Asn Pro Ser Leu
    50                  55                  60

Lys Ser Arg Ile Thr Ile Thr Arg Asp Thr Ser Glu Asn Gln Leu Ser
65                  70                  75                  80

Leu Lys Leu Ser Ser Val Thr Ala Ala Asp Thr Ala Val Tyr Tyr Cys
                85                  90                  95

Ala Arg Ser Pro Tyr Asp Ser Asp Pro Tyr Tyr Val Met Asp Tyr Trp
            100                 105                 110

Gly Gln Gly Thr Leu Val Thr Val Ser Ser
        115                 120

<210> SEQ ID NO 17
<211> LENGTH: 113
<212> TYPE: PRT
<213> ORGANISM: Artificial sequence
<220> FEATURE:
<223> OTHER INFORMATION: AB12T3 VL

<400> SEQUENCE: 17

Asp Ile Val Met Ser Gln Ser Pro Asp Ser Leu Ala Val Ser Leu Gly
1               5                   10                  15

Glu Arg Ala Thr Ile Thr Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Pro Pro Thr Leu Leu Ile Tyr Trp Ala Ser Thr Arg Asp Ser Gly Val
    50                  55                  60

Pro Asp Arg Leu Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ala Tyr Pro Tyr Thr Phe Gly Gln Gly Thr Lys Leu Glu Ile
            100                 105                 110

Lys
```

```
<210> SEQ ID NO 18
<211> LENGTH: 122
<212> TYPE: PRT
<213> ORGANISM: Artificial sequence
<220> FEATURE:
<223> OTHER INFORMATION: AB12T4 VH

<400> SEQUENCE: 18

Asp Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Phe
            20                  25                  30

Tyr Ser Trp His Trp Ile Arg Gln Phe Pro Gly Lys Gly Leu Glu Trp
        35                  40                  45

Met Gly Cys Ile Gln Tyr Ser Gly Asp Thr Asp Ser Asn Pro Ser Leu
    50                  55                  60

Lys Ser Arg Ile Thr Ile Thr Arg Asp Thr Ser Glu Asn Gln Leu Phe
65                  70                  75                  80

Leu Lys Leu Ser Ser Val Thr Ala Ala Asp Thr Ala Thr Tyr Tyr Cys
                85                  90                  95

Ala Arg Ser Pro Tyr Asp Ser Asp Pro Tyr Tyr Val Met Asp Tyr Trp
            100                 105                 110

Gly Gln Gly Thr Leu Val Thr Val Ser Ser
        115                 120

<210> SEQ ID NO 19
<211> LENGTH: 113
<212> TYPE: PRT
<213> ORGANISM: Artificial sequence
<220> FEATURE:
<223> OTHER INFORMATION: AB12T4 VL

<400> SEQUENCE: 19

Asp Ile Val Met Ser Gln Ser Pro Asp Ser Leu Ala Val Ser Leu Gly
1               5                   10                  15

Glu Arg Ile Thr Met Thr Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Thr Leu Leu Ile Tyr Trp Ala Ser Thr Arg Asp Ser Gly Val
    50                  55                  60

Pro Asp Arg Leu Thr Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ala Tyr Pro Tyr Thr Phe Gly Gln Gly Thr Lys Leu Glu Ile
            100                 105                 110

Lys

<210> SEQ ID NO 20
<211> LENGTH: 122
<212> TYPE: PRT
<213> ORGANISM: Artificial sequence
<220> FEATURE:
<223> OTHER INFORMATION: AB12T5 VH

<400> SEQUENCE: 20

Gln Val Gln Leu Gln Glu Ser Gly Pro Gly Leu Val Lys Pro Ser Gln
```

-continued

```
1               5                   10                  15
Thr Leu Ser Leu Thr Cys Thr Val Ser Gly Tyr Ser Ile Thr Ser Phe
            20                  25                  30

Tyr Ser Trp His Trp Ile Arg Gln His Pro Gly Lys Gly Leu Glu Trp
            35                  40                  45

Ile Gly Cys Ile Gln Tyr Ser Gly Asp Thr Asp Ser Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Pro Tyr Asp Ser Asp Pro Tyr Tyr Val Met Asp Tyr Trp
                100                 105                 110

Gly Gln Gly Thr Ser Val Thr Val Ser Ser
            115                 120
```

<210> SEQ ID NO 21
<211> LENGTH: 113
<212> TYPE: PRT
<213> ORGANISM: Artificial sequence
<220> FEATURE:
<223> OTHER INFORMATION: AB12T5 VL

<400> SEQUENCE: 21

```
Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ala Tyr Pro Tyr Thr Phe Gly Gly Gly Thr Lys Leu Glu Ile
                100                 105                 110

Lys
```

<210> SEQ ID NO 22
<211> LENGTH: 122
<212> TYPE: PRT
<213> ORGANISM: Artificial sequence
<220> FEATURE:
<223> OTHER INFORMATION: AB12T6 VH

<400> SEQUENCE: 22

```
Asp Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Phe
            20                  25                  30

Tyr Ser Trp His Trp Ile Arg Gln His Pro Gly Lys Gly Leu Glu Trp
            35                  40                  45

Met Gly Cys Ile Gln Tyr Ser Gly Asp Thr Tyr Tyr Asn Pro Ser Leu
    50                  55                  60

Lys Ser Arg Val Thr Ile Ser Val Asp Thr Ser Lys Asn Gln Phe Ser
```

```
                    65                  70                  75                  80
Leu Lys Leu Ser Ser Val Thr Ala Ala Asp Thr Ala Val Tyr Tyr Cys
                85                  90                  95

Ala Arg Ser Pro Tyr Asp Ser Asp Pro Tyr Tyr Val Met Asp Tyr Trp
            100                 105                 110

Gly Gln Gly Thr Leu Val Thr Val Ser Ser
        115                 120

<210> SEQ ID NO 23
<211> LENGTH: 113
<212> TYPE: PRT
<213> ORGANISM: Artificial sequence
<220> FEATURE:
<223> OTHER INFORMATION: AB12T6 VL

<400> SEQUENCE: 23

Asp Ile Val Met Ser Gln Ser Pro Asp Ser Leu Ala Val Ser Leu Gly
1               5                  10                  15

Glu Arg Ala Thr Ile Thr Cys Lys Ser Ser Gln Ser Leu Leu Tyr Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ala Tyr Pro Tyr Thr Phe Gly Gly Gly Thr Lys Leu Glu Thr
            100                 105                 110

Lys

<210> SEQ ID NO 24
<211> LENGTH: 122
<212> TYPE: PRT
<213> ORGANISM: Artificial sequence
<220> FEATURE:
<223> OTHER INFORMATION: AB12T7 VH

<400> SEQUENCE: 24

Gln Val Gln Leu Gln Glu Ser Gly Pro Gly Leu Val Lys Pro Ser Gln
1               5                  10                  15

Thr Leu Ser Leu Thr Cys Thr Val Ser Gly Tyr Ser Ile Thr Ser Phe
                20                  25                  30

Tyr Ser Trp Ser Trp Ile Arg Gln His Pro Gly Lys Gly Leu Glu Trp
            35                  40                  45

Ile Gly Tyr Ile Gln Tyr Ser Gly Asp Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Pro Tyr Asp Ser Asp Pro Tyr Tyr Val Met Asp Tyr Trp
            100                 105                 110

Gly Gln Gly Thr Leu Val Thr Val Ser Ser
        115                 120
```

<210> SEQ ID NO 25
<211> LENGTH: 113
<212> TYPE: PRT
<213> ORGANISM: Artificial sequence
<220> FEATURE:
<223> OTHER INFORMATION: AB12T7 VL

<400> SEQUENCE: 25

```
Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ala Tyr Pro Tyr Thr Phe Gly Gln Gly Thr Lys Leu Glu Ile
            100                 105                 110

Lys
```

<210> SEQ ID NO 26
<211> LENGTH: 122
<212> TYPE: PRT
<213> ORGANISM: Artificial sequence
<220> FEATURE:
<223> OTHER INFORMATION: AB12T8/AB12T9 VH

<400> SEQUENCE: 26

```
Asp Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Phe
            20                  25                  30

Tyr Ser Trp His Trp Ile Arg Gln Phe Pro Gly Lys Gly Leu Glu Trp
        35                  40                  45

Met Gly Ala Ile Gln Tyr Ser Gly Asp Thr Asp Ser Asn Pro Ser Leu
    50                  55                  60

Lys Ser Arg Ile Thr Ile Thr Arg Asp Thr Ser Glu Asn Gln Leu Phe
65                  70                  75                  80

Leu Lys Leu Ser Ser Val Thr Ala Ala Asp Thr Ala Thr Tyr Tyr Cys
                85                  90                  95

Ala Arg Ser Pro Tyr Asp Ser Asp Pro Tyr Tyr Val Met Asp Tyr Trp
            100                 105                 110

Gly Gln Gly Thr Leu Val Thr Val Ser Ser
        115                 120
```

<210> SEQ ID NO 27
<211> LENGTH: 113
<212> TYPE: PRT
<213> ORGANISM: Artificial sequence
<220> FEATURE:
<223> OTHER INFORMATION: AB12T8/AB12T9 VL

<400> SEQUENCE: 27

```
Asp Ile Val Met Ser Gln Ser Pro Asp Ser Leu Ala Val Ser Leu Gly
1               5                   10                  15
```

```
Glu Arg Ile Thr Met Thr Cys Lys Ser Ser Gln Ser Leu Leu Tyr Ser
                20                  25                  30

Gly Asn Gln Lys Asn Tyr Leu Ala Trp Tyr Gln Lys Pro Gly Gln
        35                  40                  45

Ser Pro Thr Leu Leu Ile Tyr Trp Ala Ser Thr Arg Asp Ser Gly Val
 50                  55                  60

Pro Asp Arg Leu Thr Gly Ser Gly Ser Gly Thr Asp Phe Thr Leu Thr
65                   70                  75                  80

Ile Ser Ser Val Gln Ala Glu Asp Val Ala Val Tyr Tyr Cys Gln Gln
                85                  90                  95

Tyr Tyr Ala Tyr Pro Tyr Thr Phe Gly Gln Gly Thr Lys Leu Glu Ile
            100                 105                 110

Lys

<210> SEQ ID NO 28
<211> LENGTH: 327
<212> TYPE: PRT
<213> ORGANISM: Homo sapiens

<400> SEQUENCE: 28

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
65                   70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 29
<211> LENGTH: 327
<212> TYPE: PRT
<213> ORGANISM: Artificial sequence
<220> FEATURE:
<223> OTHER INFORMATION: Variant of Human IgG4 heavy chain constant
      region??IgG4 V1??

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

-continued

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 30
<211> LENGTH: 330
<212> TYPE: PRT
<213> ORGANISM: Homo sapiens

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 31
<211> LENGTH: 330
<212> TYPE: PRT
<213> ORGANISM: Artificial sequence
<220> FEATURE:
<223> OTHER INFORMATION: Variant of Human IgG1 heavy chain constant region??IgG1 V1??

<400> SEQUENCE: 31

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 32
<211> LENGTH: 330
<212> TYPE: PRT
<213> ORGANISM: Artificial sequence
<220> FEATURE:

<223> OTHER INFORMATION: Variant of Human IgG1 heavy chain constant
      region??IgG1 V2??

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 33
<211> LENGTH: 107
<212> TYPE: PRT
<213> ORGANISM: Homo sapiens

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 34
<211> LENGTH: 366
<212> TYPE: DNA
<213> ORGANISM: Artificial sequence
<220> FEATURE:
<223> OTHER INFORMATION: The nucleotide sequence of AB12T8 VH

<400> SEQUENCE: 34

```
gatgtgcagc tgcaggagag cggaccagga ctggtgaagc cttcccagac actgagcctg      60
acctgcacag tgaccggcta tagcatcacc tcttttttact cctggcactg gatcagacag     120
ttcccaggca agggcctgga gtggatgggc gctatccagt actctggcga tacagacagc     180
aacccctctc tgaagtccag gatcacaatc acccgggata cctctgagaa tcagctgttc     240
ctgaagctgt ccagcgtgac agccgctgac accgccacct actattgcgc taggtctcca     300
tatgattccg acccctacta tgtgatggac tactggggcc agggcacact ggtgaccgtg     360
tcttcc                                                                366
```

<210> SEQ ID NO 35
<211> LENGTH: 339
<212> TYPE: DNA
<213> ORGANISM: Artificial sequence
<220> FEATURE:
<223> OTHER INFORMATION: The nucleotide sequence of AB12T8 VL

<400> SEQUENCE: 35

```
gacatcgtga tgagccagtc tccagacagc ctggccgtgt ctctgggaga gaggatcaca      60
atgacctgta agagctctca gtccctgctg tatagcggca ccagaagaa ttatctggct      120 tggtaccagc agaagccagg acagtcccct acactgctga tctactgggc ttctaccagg     180
gattccggag tgcctgacag gctgacaggc tccggaagcg gaaccgactt cacccctgacc    240 atctccagcg tgcaggctga ggacgtggcc gtgtactatt gccagcagta ctatgcctac     300
ccttatacat tcggccaggg caccaagctg gagatcaag                            339
```

<210> SEQ ID NO 36
<211> LENGTH: 447
<212> TYPE: PRT
<213> ORGANISM: Artificial sequence
<220> FEATURE:
<223> OTHER INFORMATION: AB12T1 heavy chain

<400> SEQUENCE: 36

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

```
Tyr Trp Asn Trp Ile Arg Gln Pro Pro Gly Lys Gly Leu Glu Trp Ile
             35                  40                  45

Gly Glu Ile Asn His Arg Gly Ser Thr Asn Ser Asn Pro Ser Leu Lys
 50                  55                  60

Ser Arg Val Thr Leu Ser Leu Asp Thr Ser Lys Asn Gln Phe Ser Leu
 65                  70                  75                  80

Lys Leu Arg Ser Val Thr Ala Ala Asp Thr Ala Val Tyr Tyr Cys Ala
                 85                  90                  95

Phe Gly Tyr Ser Asp Tyr Glu Tyr Asn Trp Phe Asp Pro Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445
```

```
<210> SEQ ID NO 37
<211> LENGTH: 214
<212> TYPE: PRT
<213> ORGANISM: Artificial sequence
<220> FEATURE:
<223> OTHER INFORMATION: AB12T1 light chain

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 38
<211> LENGTH: 449
<212> TYPE: PRT
<213> ORGANISM: Artificial sequence
<220> FEATURE:
<223> OTHER INFORMATION: AB12T2 heavy chain

<400> SEQUENCE: 38

Asp Val His Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Phe
            20                  25                  30

Tyr Ser Trp His Trp Ile Arg Gln Phe Pro Gly Asn Lys Leu Glu Trp
        35                  40                  45

Met Gly Cys Ile Gln Tyr Ser Gly Asp Thr Ser Asn Pro Ser Leu
    50                  55                  60

Lys Ser Arg Ile Ser Ile Thr Arg Asp Thr Ser Glu Asn Gln Leu Phe
65                  70                  75                  80

Leu His Leu Asn Ser Val Thr Thr Glu Asp Thr Ala Thr Tyr Tyr Cys
                85                  90                  95
```

Ala Arg Ser Pro Tyr Asp Ser Asp Pro Tyr Tyr Val Met Asp Tyr Trp
            100                 105                 110

Gly Gln Gly Thr Ser Val Thr Val Ser Ser Ala Ser Thr Lys Gly Pro
            115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
            210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 39
<211> LENGTH: 220
<212> TYPE: PRT
<213> ORGANISM: Artificial sequence
<220> FEATURE:
<223> OTHER INFORMATION: AB12T2 light chain

<400> SEQUENCE: 39

Asp Ile Val Met Ser Gln Ser Pro Ser Ser Leu Ala Val Ser Val Gly
1               5                   10                  15

Glu Lys Ile Thr Met Thr Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Thr Leu Leu Ile Tyr Trp Ala Ser Thr Arg Asp Ser Gly Val
    50                  55                  60

Pro Asp Arg Leu Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ala Tyr Pro Tyr Thr Phe Gly Gly Gly Thr Lys Leu Glu Thr
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 40
<211> LENGTH: 449
<212> TYPE: PRT
<213> ORGANISM: Artificial sequence
<220> FEATURE:
<223> OTHER INFORMATION: AB12T3 heavy chain

<400> SEQUENCE: 40

Asp Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Phe
            20                  25                  30

Tyr Ser Trp His Trp Ile Arg Gln His Pro Gly Lys Gly Leu Glu Trp
        35                  40                  45

Met Gly Cys Ile Gln Tyr Ser Gly Asp Thr Asp Ser Asn Pro Ser Leu
    50                  55                  60

Lys Ser Arg Ile Thr Ile Thr Arg Asp Thr Ser Glu Asn Gln Leu Ser
65                  70                  75                  80

Leu Lys Leu Ser Ser Val Thr Ala Ala Asp Thr Ala Val Tyr Tyr Cys
                85                  90                  95

Ala Arg Ser Pro Tyr Asp Ser Asp Pro Tyr Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
            210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 41
<211> LENGTH: 220
<212> TYPE: PRT
<213> ORGANISM: Artificial sequence
<220> FEATURE:
<223> OTHER INFORMATION: AB12T3 light chain

<400> SEQUENCE: 41

Asp Ile Val Met Ser Gln Ser Pro Asp Ser Leu Ala Val Ser Leu Gly
1               5                   10                  15

Glu Arg Ala Thr Ile Thr Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
            35                  40                  45

Pro Pro Thr Leu Leu Ile Tyr Trp Ala Ser Thr Arg Asp Ser Gly Val

Pro Asp Arg Leu Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ala Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 42
<211> LENGTH: 449
<212> TYPE: PRT
<213> ORGANISM: Artificial sequence
<220> FEATURE:
<223> OTHER INFORMATION: AB12T4 heavy chain

<400> SEQUENCE: 42

Asp Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Phe
            20                  25                  30

Tyr Ser Trp His Trp Ile Arg Gln Phe Pro Gly Lys Gly Leu Glu Trp
        35                  40                  45

Met Gly Cys Ile Gln Tyr Ser Gly Asp Thr Asp Ser Asn Pro Ser Leu
    50                  55                  60

Lys Ser Arg Ile Thr Ile Thr Arg Asp Thr Ser Glu Asn Gln Leu Phe
65                  70                  75                  80

Leu Lys Leu Ser Ser Val Thr Ala Ala Asp Thr Ala Thr Tyr Tyr Cys
                85                  90                  95

Ala Arg Ser Pro Tyr Asp Ser Asp Pro Tyr Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp

```
                195                 200                 205
His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 43
<211> LENGTH: 220
<212> TYPE: PRT
<213> ORGANISM: Artificial sequence
<220> FEATURE:
<223> OTHER INFORMATION: AB12T4 light chain

<400> SEQUENCE: 43

Asp Ile Val Met Ser Gln Ser Pro Asp Ser Leu Ala Val Ser Leu Gly
1               5                   10                  15

Glu Arg Ile Thr Met Thr Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Thr Leu Leu Ile Tyr Trp Ala Ser Thr Arg Asp Ser Gly Val
    50                  55                  60

Pro Asp Arg Leu Thr Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ala Tyr Pro Tyr Thr Phe Gly Gln Gly Thr Lys Leu Glu Ile
            100                 105                 110
```

```
Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
            210                 215                 220

<210> SEQ ID NO 44
<211> LENGTH: 449
<212> TYPE: PRT
<213> ORGANISM: Artificial sequence
<220> FEATURE:
<223> OTHER INFORMATION: AB12T5 heavy chain

<400> SEQUENCE: 44

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Phe
            20                  25                  30

Tyr Ser Trp His Trp Ile Arg Gln His Pro Gly Lys Gly Leu Glu Trp
        35                  40                  45

Ile Gly Cys Ile Gln Tyr Ser Gly Asp Thr Asp Ser Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Pro Tyr Asp Ser Asp Pro Tyr Tyr Val Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 45
<211> LENGTH: 220
<212> TYPE: PRT
<213> ORGANISM: Artificial sequence
<220> FEATURE:
<223> OTHER INFORMATION: AB12T5 light chain

<400> SEQUENCE: 45

Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ala Tyr Pro Tyr Thr Phe Gly Gly Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160
```

```
Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 46
<211> LENGTH: 449
<212> TYPE: PRT
<213> ORGANISM: Artificial sequence
<220> FEATURE:
<223> OTHER INFORMATION: AB12T6 heavy chain

<400> SEQUENCE: 46

Asp Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Phe
            20                  25                  30

Tyr Ser Trp His Trp Ile Arg Gln His Pro Gly Lys Gly Leu Glu Trp
            35                  40                  45

Met Gly Cys Ile Gln Tyr Ser Gly Asp Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Pro Tyr Asp Ser Asp Pro Tyr Tyr Val Met Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
            210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
            290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 47
<211> LENGTH: 220
<212> TYPE: PRT
<213> ORGANISM: Artificial sequence
<220> FEATURE:
<223> OTHER INFORMATION: AB12T6 light chain

<400> SEQUENCE: 47

Asp Ile Val Met Ser Gln Ser Pro Asp Ser Leu Ala Val Ser Leu Gly
1               5                   10                  15

Glu Arg Ala Thr Ile Thr Cys Lys Ser Ser Gln Ser Leu Leu Tyr Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Asp Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ala Tyr Pro Tyr Thr Phe Gly Gly Gly Thr Lys Leu Glu Thr
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
```

<210> SEQ ID NO 48
<211> LENGTH: 449
<212> TYPE: PRT
<213> ORGANISM: Artificial sequence
<220> FEATURE:
<223> OTHER INFORMATION: AB12T7 heavy chain

<400> SEQUENCE: 48

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Phe
            20                  25                  30

Tyr Ser Trp Ser Trp Ile Arg Gln His Pro Gly Lys Gly Leu Glu Trp
        35                  40                  45

Ile Gly Tyr Ile Gln Tyr Ser Gly Asp Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Pro Tyr Asp Ser Asp Pro Tyr Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
```

```
                355                 360                 365
Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
                435                 440                 445

Lys

<210> SEQ ID NO 49
<211> LENGTH: 220
<212> TYPE: PRT
<213> ORGANISM: Artificial sequence
<220> FEATURE:
<223> OTHER INFORMATION: AB12T7 light chain

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ala Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 50
<211> LENGTH: 452
<212> TYPE: PRT
<213> ORGANISM: Artificial sequence
<220> FEATURE:
<223> OTHER INFORMATION: AB12T8 heavy chain
```

```
<400> SEQUENCE: 50

Asp Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Phe
            20                  25                  30

Tyr Ser Trp His Trp Ile Arg Gln Phe Pro Gly Lys Gly Leu Glu Trp
        35                  40                  45

Met Gly Ala Ile Gln Tyr Ser Gly Asp Thr Asp Ser Asn Pro Ser Leu
    50                  55                  60

Lys Ser Arg Ile Thr Ile Thr Arg Asp Thr Ser Glu Asn Gln Leu Phe
65                  70                  75                  80

Leu Lys Leu Ser Ser Val Thr Ala Ala Asp Thr Ala Thr Tyr Tyr Cys
                85                  90                  95

Ala Arg Ser Pro Tyr Asp Ser Asp Pro Tyr Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
        450

<210> SEQ ID NO 51
<211> LENGTH: 220
<212> TYPE: PRT
<213> ORGANISM: Artificial sequence
<220> FEATURE:
<223> OTHER INFORMATION: AB12T8 light chain

<400> SEQUENCE: 51

Asp Ile Val Met Ser Gln Ser Pro Asp Ser Leu Ala Val Ser Leu Gly
1               5                   10                  15

Glu Arg Ile Thr Met Thr Cys Lys Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Thr Leu Leu Ile Tyr Trp Ala Ser Thr Arg Asp Ser Gly Val
    50                  55                  60

Pro Asp Arg Leu Thr Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ala Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 52
<211> LENGTH: 452
<212> TYPE: PRT
<213> ORGANISM: Artificial sequence
<220> FEATURE:
<223> OTHER INFORMATION: AB12T9 heavy chain

<400> SEQUENCE: 52

Asp Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Phe
            20                  25                  30

Tyr Ser Trp His Trp Ile Arg Gln Phe Pro Gly Lys Gly Leu Glu Trp

-continued

```
            35                  40                  45
Met Gly Ala Ile Gln Tyr Ser Gly Asp Thr Asp Ser Asn Pro Ser Leu
 50                  55                  60

Lys Ser Arg Ile Thr Ile Thr Arg Asp Thr Ser Glu Asn Gln Leu Phe
 65                  70                  75                  80

Leu Lys Leu Ser Ser Val Thr Ala Ala Asp Thr Ala Thr Tyr Tyr Cys
                 85                  90                  95

Ala Arg Ser Pro Tyr Asp Ser Asp Pro Tyr Tyr Val Met Asp Tyr Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Ala Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
            450
```

<210> SEQ ID NO 53
<211> LENGTH: 220
<212> TYPE: PRT
<213> ORGANISM: Artificial sequence
<220> FEATURE:
<223> OTHER INFORMATION: AB12T9 light chain

<400> SEQUENCE: 53

```
Asp Ile Val Met Ser Gln Ser Pro Asp Ser Leu Ala Val Ser Leu Gly
1               5                   10                  15

Glu Arg Ile Thr Met Thr Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Thr Leu Leu Ile Tyr Trp Ala Ser Thr Arg Asp Ser Gly Val
    50                  55                  60

Pro Asp Arg Leu Thr Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ala Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 54
<211> LENGTH: 7
<212> TYPE: PRT
<213> ORGANISM: Artificial sequence
<220> FEATURE:
<223> OTHER INFORMATION: Chothia/ Kabat AB12T7 LCDR2

<400> SEQUENCE: 54

```
Trp Ala Ser Thr Arg Glu Ser
1               5
```

<210> SEQ ID NO 55
<211> LENGTH: 16
<212> TYPE: PRT
<213> ORGANISM: Artificial sequence
<220> FEATURE:
<223> OTHER INFORMATION: Kabat AB12T6 HCDR2

<400> SEQUENCE: 55

```
Cys Ile Gln Tyr Ser Gly Asp Thr Tyr Tyr Asn Pro Ser Leu Lys Ser
1               5                   10                  15
```

```
<210> SEQ ID NO 56
<211> LENGTH: 6
<212> TYPE: PRT
<213> ORGANISM: Artificial sequence
<220> FEATURE:
<223> OTHER INFORMATION: Kabat AB12T7 HCDR1

<400> SEQUENCE: 56

Ser Phe Tyr Ser Trp Ser
1               5

<210> SEQ ID NO 57
<211> LENGTH: 16
<212> TYPE: PRT
<213> ORGANISM: Artificial sequence
<220> FEATURE:
<223> OTHER INFORMATION: Kabat AB12T7 HCDR2

<400> SEQUENCE: 57

Tyr Ile Gln Tyr Ser Gly Asp Thr Tyr Tyr Asn Pro Ser Leu Lys Ser
1               5                   10                  15

<210> SEQ ID NO 58
<211> LENGTH: 16
<212> TYPE: PRT
<213> ORGANISM: Artificial sequence
<220> FEATURE:
<223> OTHER INFORMATION: Kabat AB12T8 HCDR2

<400> SEQUENCE: 58

Ala Ile Gln Tyr Ser Gly Asp Thr Asp Ser Asn Pro Ser Leu Lys Ser
1               5                   10                  15
```